(12) United States Patent
Thomason et al.

(10) Patent No.: US 7,727,742 B2
(45) Date of Patent: *Jun. 1, 2010

(54) NUCLEIC ACID MOLECULES ENCODING FIBROBLAST GROWTH FACTOR-LIKE POLYPEPTIDES

(75) Inventors: Arlen Thomason, Walterville, OR (US); Benxian Liu, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/163,755

(22) Filed: Jun. 27, 2008

(65) Prior Publication Data

US 2009/0017498 A1 Jan. 15, 2009

Related U.S. Application Data

(63) Continuation of application No. 09/391,861, filed on Sep. 7, 1999, now Pat. No. 7,408,047.

(51) Int. Cl.
- *C07H 21/00* (2006.01)
- *C12P 21/02* (2006.01)
- *C12N 15/00* (2006.01)
- *C12N 15/06* (2006.01)
- *C12N 15/09* (2006.01)
- *C12N 15/18* (2006.01)

(52) U.S. Cl. .......... 435/69.4; 435/69.1; 435/70.1; 435/320.1; 435/325; 536/23.51

(58) Field of Classification Search .............. None
See application file for complete search history.

(56) References Cited

U.S. PATENT DOCUMENTS

| | | | |
|---|---|---|---|
| 3,773,919 A | 11/1973 | Boswell et al. |
| 4,179,337 A | 12/1979 | Davis et al. |
| 4,376,110 A | 3/1983 | David et al. |
| 4,816,567 A | 3/1989 | Cabilly et al. |
| 4,892,538 A | 1/1990 | Aebischer et al. |
| 4,945,050 A | 7/1990 | Sanford et al. |
| 4,970,154 A | 11/1990 | Chang |
| 5,011,472 A | 4/1991 | Aebischer et al. |
| 5,106,627 A | 4/1992 | Aebischer et al. |
| 5,217,889 A | 6/1993 | Roninson et al. |
| 5,234,784 A | 8/1993 | Aslam et al. |
| 5,252,714 A | 10/1993 | Harris et al. |
| 5,272,071 A | 12/1993 | Chappel |
| 5,364,791 A | 11/1994 | Vegeto et al. |
| 5,489,743 A | 2/1996 | Robinson et al. |
| 5,557,032 A | 9/1996 | Mak |
| 5,589,362 A | 12/1996 | Bujard et al. |
| 5,593,875 A | 1/1997 | Wurm et al. |
| 5,635,399 A | 6/1997 | Kriegler et al. |
| 5,650,298 A | 7/1997 | Bujard et al. |
| 5,654,168 A | 8/1997 | Bujard et al. |
| 5,672,510 A | 9/1997 | Eglitis et al. |
| 5,676,954 A | 10/1997 | Brigham |
| 5,679,559 A | 10/1997 | Kim et al. |
| 5,811,234 A | 9/1998 | Roninson et al. |
| 6,150,098 A | 11/2000 | Zhang |
| 6,639,063 B1 | 10/2003 | Edwards |
| 6,716,626 B1 | 4/2004 | Itoh |
| 7,259,248 B2 | 8/2007 | Itoh |
| 7,408,047 B1 | 8/2008 | Thomason et al. |
| 2001/0012628 A1 | 8/2001 | Agarwal et al. |
| 2007/0128619 A1 | 6/2007 | Itoh |
| 2007/0238657 A1 | 10/2007 | Itoh |

FOREIGN PATENT DOCUMENTS

| | | |
|---|---|---|
| EP | 0036676 | 9/1981 |
| EP | 0058481 | 8/1982 |
| EP | 0088046 | 9/1983 |
| EP | 0133988 | 3/1985 |
| EP | 0143949 | 6/1985 |
| EP | 0154316 | 9/1985 |
| EP | 0401384 | 12/1990 |
| EP | 0505500 | 9/1992 |
| WO | WO 91/09955 | 7/1991 |
| WO | WO 91/10425 | 7/1991 |
| WO | WO 91/10470 | 7/1991 |
| WO | WO 93/15722 | 8/1993 |
| WO | WO 94/20069 | 9/1994 |
| WO | WO 94/28122 | 12/1994 |
| WO | WO 95/05452 | 2/1995 |
| WO | WO 95/34670 | 12/1995 |
| WO | WO 96/37609 | 11/1996 |
| WO | WO 96/40958 | 12/1996 |

(Continued)

OTHER PUBLICATIONS

Galzie et al. (Biochem. Cell Biol. 75: 669-685, 1997).*
Brenner (1999,Trends in Genetics 15:132-133).*
Bork et al. (1996, Trends in Genetics 12;425-427).*
Ngo et al., 1994, The protein Folding problem and -tertiary Structure prediction, pp. 492-495.*

(Continued)

*Primary Examiner*—Christine J Saoud
(74) *Attorney, Agent, or Firm*—McDonnell Bozhnen Hulbert & Berghoff LLP

(57) ABSTRACT

The present invention provides nucleic acid molecules encoding Fibroblast Growth Factor-like (FGF-like) polypeptides. The invention also provides vectors, host cells, and methods for producing FGF-like polypeptides.

10 Claims, 10 Drawing Sheets

FOREIGN PATENT DOCUMENTS

| | | |
|---|---|---|
| WO | WO 96/41865 | 12/1996 |
| WO | WO 97/31899 | 9/1997 |
| WO | WO 00/54813 | 9/2000 |
| WO | WO 01/18209 | 3/2001 |
| WO | WO 01/32678 | 5/2001 |
| WO | WO 01/36640 | 5/2001 |
| WO | WO 01/38357 | 5/2001 |
| WO | WO 01/49849 | 7/2001 |

OTHER PUBLICATIONS

Wang et al. (Nuc. Acids Res. 27: 4609-4618, 1999).*
Phillips, A., J Pharm Pharmacology 53: 1169-1174, 2001.*
Kaufman et al (Blood 94: 3178-3184, 1999.*
Mahairas et al. (PNAS 96(17): 9739-9744, 1999.*
The ADHR consortium (2000), "Autosomal dominant hypophosphataemic rickets is associated with mutations in FGF23." Nature Genetics 26: 345-348.
Artuc et al. (1999), "Mast cells and their mediators in cutaneous wound healing—active participants or innocent bystanders?" Exp. Dermatol. 8: 1-16.
Beck and Podolsky (1999), "Growth factors in inflammatory bowel disease." Inflamm. Bowel Dis. 5: 44-60.
Bishop (1996), "Chromosomal insertion of foreign DNA," Reprod. Nutr. Dev. 36(6): 607-18.
Bork et al. (1996), "Go hunting in sequence databases but watch out for the traps," Trends Genet. 12(10): 425-27.
Bork et al. (1998), "Predicting functions from protein sequences—where are the bottlenecks?" Nature Genetics 18(4):313-18.
Bork (2000), "Powers and pitfalls in sequence analysis: the 70% hurdle," Genome Res. 10(4): 398-400.
Branch (1998), "A good antisense molecule is hard to find." Trends Biochem Sci. 23(2): 45-50.
Brenner (1999), "Errors in genome annotation," Trends Genet. 15(4): 132-33.
Cunha et al. (1996), "Keratinocyte growth factor as mediator of mesenchymal-epithelial interactions in the development of androgen target organs." Semin Cell Dev Biol 7: 203-210.
Doerks et al. (1998), "Protein annotation: detective work for function prediction," Trends Genet. 14(6): 248-50.
Ebadi et al. (1997), "Neurotrophins and their receptors in nerve injury and repair." Neurochem. Int. 30: 347-74.
Econs and McEnery. "Autosomal dominant hypophosphatemic rickets/osteomalacia: clinical characterization of a novel renal phosphate-wasting disorder." J Clin Endocrinol Metab 82:674-681 (1997).
Faham et al. (1998), "Diversity does make a difference: fibroblast growth factor-heparin interactions," Curr. Opin. Struct. Biol. 8(5): 578-86.
Galzie Z. et al. (1997), "Fibroblast Growth Factors and their Receptors", Biochemistry and Cell Biology 75(6):669-685.
GenBank Acc. No. AB006136, Aug. 27, 1997.
GenBank Acc. No. AQ175436, Sep. 21, 1998, accessed Nov. 18, 2005.
GenBank Acc. No. AV050323, Jun. 16, 1999, accessed Nov. 18, 2005.
GenBank Acc. No. BAA99415, Aug. 3, 2000.
GenBank Acc. No. BAA99416, Jul. 11, 2000.
GenBank Acc. No. NP_061986, Apr. 6, 2003.
GenBank Acc. No. Q9NSA1, Oct. 1, 2000.
Ghielli et al. (1998), "Regeneration processes in the kidney after acute injury: role of infiltrating cells." Exp. Nephrol. 6: 502-507.
Goldfarb (1996), "Functions of fibroblast growth factors in vertebrate development," Cytokine Growth Factor Rev. 7(4): 311-325.
Hoppenreijs et al. (1996), "Corneal endothelium and growth factors." Surv. Opthalmol. 41: 155-64.
Hull et al (1997), "Healing with basic fibroblast growth factor is associated with reduced indomethacin induced relapse in a human model of gastric ulceration," Gut 40: 204-10.
Hsu et al. (1999), "Heparin Is Essential for a Single Keratinocyte Growth Factor Molecule To Bind and Form a Complex with Two Molecules of the Extracellular Domain of Its Receptor," Biochemistry 38: 2523-34.
Hu et al., (1998), "FGF-18, a novel member of the fibroblast growth factor family, stimulates hepatic and intestinal proliferation," Mol. Cell. Biol. 18(10): 6063-6074.
Kennell (1971), "Principles and practices of nucleic acid hybridization," Progr. Nucl. Acid Res. Mol. Biol. 11: 259-301.
Kornmann et al. (1998), "Role of fibroblast growth factors and their receptors in pancreatic cancer and chronic pancreatitis." Pancreas 17: 169-75.
Ledley (1996), "Pharmaceutical Approach to Somatic Gene Therapy." Pharm. Res. 13(11): 1595-1614.
Lewis el al. (1997), "Angiogenesis by gene therapy: a new horizon for myocardial revascularization?" Cardiovasc. Res. 135: 490-497.
Mikkelsen (1993), "Interpreting sequence motifs: a cautionary note," Trends Genet. 9(5): 15.
Nakamura et al. (1995), "The murine lymphotoxin-beta receptor cDNA: isolation by the signal sequence trap and chromosomal mapping," Genomics 30(2): 312-19.
Ngo et al. (1994), "Computational complexity, protein structure prediction, and the Levinthal paradox," in The Protein Folding Problem and Tertiary Structure Prediction, Merz & Le Grand ed., Birkhauser: Boston, pp. 491-495.
Nishimura et al. (2000), "Identification of a novel FGF, FGF-21, preferentially expressed in the liver(I)." Biochim Biophys Acta 21: 203-6.
Niyogi (1969), "The influence of chain length and base composition on the specific association of oligoribonucleotides with denatured deoxyribonucleic acid," J. Biol. Chem. 244(6): 1576-81.
Peus and Pittelkow (1996), "Growth factors in hair organ development and the hair growth cycle." Dermatol. Clin. 14:559-72.
Podolsky (1997), "Healing the epithelium: solving the problem from two sides." J. Gastroenterol. 32: 122-6.
Polejaeva et al. (2000), "New advances in somatic cell nuclear transfer: application in transgenesis," Theriogenology 53(1): 117-26.
Plotnikov et al. (2000), "Crystal Structures of Two FGF-FGFR Complexes Reveal the Determinants of Ligand-Receptor Specificity," Cell 101: 413-24.
Ratajczak (1997), "Fibroblast growth factors and early hemopoietic cell development." Leuk. Lymphoma 27: 221-9.
Rulicke et al. (2000), "Germ line transformation of mammals by pronuclear microinjection," Exp. Physiol. 85(6): 589-601.
Skolnick et al. (2000), "From genes to protein structure and function: novel applications of computational approaches in the genomic era," Trends Biotechnol. 18(1): 34-39.
Smallwood et al. (1996), "Fibroblast Growth Factor (FGF) homologous factors: new members of the FGF family implicated in nervous system development", PNAS 93: 9850-9857.
Smith et al. (1997), "The challenges of genome sequence annotation or 'the devil is in the details,'" Nat. Biotechnol. 15(12): 1222-23.
Webster (1997), "Growth factors and myelin regeneration in multiple sclerosis." Mult. Scler. 3:113-20.
Verma et al. (1997), "Gene therapy—promises, problems and prospects." Nature 389: 239-242.
Yamaoka and Itakura (1999), "Development of pancreatic islets (review)." Int. J. Mol. Med. 3: 247-61.
Itoh and Ornitz (2004), "Evolution of the FGF and FGFR gene families." Trends in Genetics 20(11): 563-569.
Kharitonenkov et al. (2005), "FGF-21 as a novel metabolic regulator." J. Clin. Invest. 115: 1627-1635.
Kurosu et al. (2007), "Tissue-specific Expression of Klotho and Fibroblast Growth Factor (FGF) Receptor Isoforms Determines Metabolic Activity of FGF19 and FGF21." J. Biol. Chem. 282(37): 26687-26695.
Liu et al. (2007), "FGF18 is required for early chondrocyte proliferation, hypertrophy and vascular invasion of the growth plate." Dev. Biol. 302: 80-91.

* cited by examiner

Fig. 1

| | |
|---|---|
| atg gaa tgg atg aga tct aga gtt ggg acc ctg gga ctg tgg gtc cga<br>Met Glu Trp Met Arg Ser Arg Val Gly Thr Leu Gly Leu Trp Val Arg<br>1               5                           10                          15 | 48 |
| ctg ctg ctg gct gtc ttc ctg ctg ggg gtc tac caa gca tac ccc atc<br>Leu Leu Leu Ala Val Phe Leu Leu Gly Val Tyr Gln Ala Tyr Pro Ile<br>                20                          25                          30 | 96 |
| cct gac tcc agc ccc ctc ctc cag ttt ggg ggt caa gtc cgg cag agg<br>Pro Asp Ser Ser Pro Leu Leu Gln Phe Gly Gly Gln Val Arg Gln Arg<br>                   35                          40                       45 | 144 |
| tac ctc tac aca gat gac gac caa gac act gaa gcc cac ctg gag atc<br>Tyr Leu Tyr Thr Asp Asp Asp Gln Asp Thr Glu Ala His Leu Glu Ile<br>            50                          55                          60 | 192 |
| agg gag gat gga aca gtg gta ggc gca gca cac cgc agt cca gaa agt<br>Arg Glu Asp Gly Thr Val Val Gly Ala Ala His Arg Ser Pro Glu Ser<br>65                          70                          75                       80 | 240 |
| ctc ctg gag ctc aaa gcc ttg aag cca ggg gtc att caa atc ctg ggt<br>Leu Leu Glu Leu Lys Ala Leu Lys Pro Gly Val Ile Gln Ile Leu Gly<br>                        85                          90                       95 | 288 |
| gtc aaa gcc tct agg ttt ctt tgc caa cag cca gat gga gct ctc tat<br>Val Lys Ala Ser Arg Phe Leu Cys Gln Gln Pro Asp Gly Ala Leu Tyr<br>                   100                         105                      110 | 336 |
| gga tcg cct cac ttt gat cct gag gcc tgc agc ttc aga gaa ctg ctg<br>Gly Ser Pro His Phe Asp Pro Glu Ala Cys Ser Phe Arg Glu Leu Leu<br>              115                         120                      125 | 384 |
| ctg gag gac ggt tac aat gtg tac cag tct gaa gcc cat ggc ctg ccc<br>Leu Glu Asp Gly Tyr Asn Val Tyr Gln Ser Glu Ala His Gly Leu Pro<br>       130                         135                      140 | 432 |
| ctg cgt ctg cct cag aag gac tcc cca aac cag gat gca aca tcc tgg<br>Leu Arg Leu Pro Gln Lys Asp Ser Pro Asn Gln Asp Ala Thr Ser Trp<br>145                         150                      155                      160 | 480 |
| gga cct gtg cgc ttc ctg ccc atg cca ggc ctg ctc cac gag ccc caa<br>Gly Pro Val Arg Phe Leu Pro Met Pro Gly Leu Leu His Glu Pro Gln<br>                   165                         170                      175 | 528 |
| gac caa gca gga ttc ctg ccc cca gag ccc cca gat gtg ggc tcc tct<br>Asp Gln Ala Gly Phe Leu Pro Pro Glu Pro Pro Asp Val Gly Ser Ser<br>              180                         185                      190 | 576 |
| gac ccc ctg agc atg gta gag cct tta cag ggc cga agc ccc agc tat<br>Asp Pro Leu Ser Met Val Glu Pro Leu Gln Gly Arg Ser Pro Ser Tyr<br>              195                         200                      205 | 624 |
| gcg tcc tgactctttc ctgaatcta<br>Ala Ser 1 | 649 |

Fig. 2A

```
gaggatccag ccgaaagagg agccaggcac tcaggccacc tgagtctact cacctggaca    60
actggaatct ggcaccaatt ctaaaccact cagcttctcc gagctcacac cccggagatc   120
acctgaggac ccgagccatt g atg gac tcg gac gag acc ggg ttc gag cac    171
                        Met Asp Ser Asp Glu Thr Gly Phe Glu His
                         1               5                    10 tca gga ctg tgg gtt tct gtg ctg gct ggt ctt ctg ctg gga gcc tgc    219
Ser Gly Leu Trp Val Ser Val Leu Ala Gly Leu Leu Leu Gly Ala Cys
            15                  20                  25 cag gca cac ccc atc cct gac tcc agt cct ctc ctg caa ttc ggg ggc    267
Gln Ala His Pro Ile Pro Asp Ser Ser Pro Leu Leu Gln Phe Gly Gly
                30                  35                  40 caa gtc cgg cag cgg tac ctc tac aca gat gat gcc cag cag aca gaa    315
Gln Val Arg Gln Arg Tyr Leu Tyr Thr Asp Asp Ala Gln Gln Thr Glu
            45                  50                  55 gcc cac ctg gag atc agg gag gat ggg acg gtg ggg ggc gct gct gac    363
Ala His Leu Glu Ile Arg Glu Asp Gly Thr Val Gly Gly Ala Ala Asp
    60                  65                  70 cag agc ccc gaa agt ctc ctg cag ctg aaa gcc ttg aag ccg gga gtt    411
Gln Ser Pro Glu Ser Leu Leu Gln Leu Lys Ala Leu Lys Pro Gly Val
75                  80                  85                  90 att caa atc ttg gga gtc aag aca tcc agg ttc ctg tgc cag cgg cca    459
Ile Gln Ile Leu Gly Val Lys Thr Ser Arg Phe Leu Cys Gln Arg Pro
                95                  100                 105 gat ggg gcc ctg tat gga tcg ctc cac ttt gac cct gag gcc tgc agc    507
Asp Gly Ala Leu Tyr Gly Ser Leu His Phe Asp Pro Glu Ala Cys Ser
            110                 115                 120 ttc cgg gag ctg ctt ctt gag gac gga tac aat gtt tac cag tcc gaa    555
Phe Arg Glu Leu Leu Leu Glu Asp Gly Tyr Asn Val Tyr Gln Ser Glu
        125                 130                 135 gcc cac ggc ctc ccg ctg cac ctg cca ggg aac aag tcc cca cac cgg    603
Ala His Gly Leu Pro Leu His Leu Pro Gly Asn Lys Ser Pro His Arg
    140                 145                 150 gac cct gca ccc cga gga cca gct cgc ttc ctg cca cta cca ggc ctg    651
Asp Pro Ala Pro Arg Gly Pro Ala Arg Phe Leu Pro Leu Pro Gly Leu
155                 160                 165                 170 ccc ccc gca ccc ccg gag cca ccc gga atc ctg gcc ccc cag ccc ccc    699
Pro Pro Ala Pro Pro Glu Pro Pro Gly Ile Leu Ala Pro Gln Pro Pro
                175                 180                 185
```

Fig. 2B

```
gat gtg ggc tcc tcg gac cct ctg agc atg gtg gga cct tcc cag ggc   747
Asp Val Gly Ser Ser Asp Pro Leu Ser Met Val Gly Pro Ser Gln Gly
            190                 195                 200 cga agc ccc agc tac gct tcc tga agccagaggc tgtttactat gacatctcct   801
Arg Ser Pro Ser Tyr Ala Ser
            205             210 ctttatttat taggttattt atcttattta ttttttttatt tttcttactt gagataataa   861
agagttccag aggaggataa gaatgagcat gtgtgagtgt ctgagggaag acatggcagc   921
tgttttgtct cccttggccc ggacaatccc ctctacacct cccctcacgt ggtccgaggg   981
tcctggcttc ccactgggcc tcactttttt cttttctttt cttttctttt ttttgagacg   1041
gagtctcgct ctgcactcca gcccaggcca cagagcgaga ttccatctca aaaaaataaa   1101
taaataaata aataaataaa tataaaata aaaaaaaaa aaaaaaaaa aaaaaaaaa     1161 aaaaaaaaaa aaaaaaaaaa aaaaaaaa                                     1190
```

Fig. 3A

```
            1                                                         50
hAgp-26257  ~~~~~~~~~~ ~~~~~~~~~~ ~~~~~~~~~~ ~~~~~~~~~~ ~~~~~~~~~M
mAgp-26257  ~~~~~~~~~~ ~~~~~~~~~~ ~~~~~~~~~~ ~~~~~~~~~~ ~~~~~~~~~M
     Hfgf14 ~~~~~~~~~~ ~~~~~~~~~~ ~~MAAAIASG LIRQKRQARE QHWDRPSASR
     Mfgf14 ~~~~~~~~~~ ~~~~~~~~~~ ~~MAAAIASG LIRQKRQARE QHWDRPSASR
     Hfgf12 ~~~~~~~~~~ ~~~~~~~~~~ ~~MAAAIASS LIRQKRQARE SNSDRVSASK
     Mfgf13 ~~~~~~~~~~ ~~~~~~~~~~ ~~MTAAIASS LIRQKRQARE R..EKSNACK
      Hfgf5 ~~~~~~~~MS LSFLLLLFFS HLILSAWAHG EKRLAPKGQP GPAATDRNPI
      Mfgf5 ~~~~~~~~MS LSLLFLIFCS HLIHSAWAHG EKRLTPEGQP APPRNPGDSS
      Hfgf6 MALGQKLFIT MSRGAGRLQG TLWALVFLGI LVGMVVPSPA GTRA..NNTL
      Mfgf6 MALGQRLFIT MSRGAGRVQG TLQALVFLGV LVGMVVPSPA GARA..NGTL
      Hfgf4 ~~~~~~~~~~ ~MSGPGTAAV ALLPAVLLAL LAPWAGRGGA AAPTAPNGTL
      Mfgf4 ~~~~~~~~~~ ~MAKRGPTTG TLLPRVLLAL VVALADRGTA ....APNGTR
      Hfgf3 ~~~~~~~~~~ ~~~~~~~~~~ ~~~~~~~~~~ ~~~~~~~~~~ ~~~~~~~~~~
      Mfgf3 ~~~~~~~~~~ ~~~~~~~~~~ ~~~~~~~~~~ ~~~~~~~~~~ ~~~~~~~~~~
      Hfgf7 ~~~~~~~~~~ ~~~~~~~~~~ ~~~~~~~~~~ MHKWILTWIL PTLLYRSCFH
      Mfgf7 ~~~~~~~~~~ ~~~~~~~~~~ ~~~~~~~~~~ MRKWILTRIL PTLLYRSCFH
      Hfgf9 ~~~~~~~~~~ ~~~~~~~~~~ ~~~~~~~~~~ MAPLGEVGNY FGVQDAVPFG
      Mfgf9 ~~~~~~~~~~ ~~~~~~~~~~ ~~~~~~~~~~ MAPLGEVGSY FGVQDAVPFG
      Hfgf1 ~~~~~~~~~~ ~~~~~~~~~~ ~~~~~~~~~~ ~~~~~~~~~~ ~~~~~~~~~~
      Mfgf1 ~~~~~~~~~~ ~~~~~~~~~~ ~~~~~~~~~~ ~~~~~~~~~~ ~~~~~~~~~~
      Hfgf2 ~~~~~~~~~~ ~~~~~~~~~~ ~~~~~~~~~~ ~~~~~~~~~~ ~~~~~~~~~~
      Mfgf2 ~~~~~~~~~~ ~~~~~~~~~~ ~~~~~~~~~~ ~~~~~~~~~~ ~~~~~~~~~~
       cons ~~~~~~~~~~ ~~~~~~~~~~ ~~~~~~~~~~ ~~~~~~~~~~ ~~~~~~~~~~

51                                                       100
hAgp-26257  DSDETGFEHS GLWVS.VLAG LLLGACQAHP IPDSSPLLQF GGQVRQRYLY
mAgp-26257  EWMRSRVGTL GLWVRLLLAV FLLGVYQAYP IPDSSPLLQF GGQVRQRYLY
     Hfgf14 RRSSPSKN.R GLCNGNLVDI FSKVRIFGLK KRRLRRQ.DP QLKGIVTRLY
     Mfgf14 RRSSPSKN.R GLFNGNLVDI FSKVRIFGLK KRRLRRQ.DP QLKGIVTRLY
     Hfgf12 RRSSPSKDGR SLCERHVLGV FSKVRFCSGR KRPVRRRPEP QLKGIVTRLF
     Mfgf13 CVSSPSK.GK TSCDKNKLNV FSRVKLFGSK KRR.RRRPEP QLKGIVTKLY
      Hfgf5 GSSSRQSSSS AMSSSSASSS PAASLGSQGS GLEQSSFQWS PSGRRTGSLY
      Mfgf5 GSRGR..SSA TFSSSSASSP VAASPGSQGS GSEHSSFQWS PSGRRTGSLY
      Hfgf6 LD..SRGWGT LLSRSRAGL. .AGEI..AGV NWESG...YL VGIKRQRRLY
      Mfgf6 LD..SRGWGT LLSRSRAGL. .AGEI..SGV NWESG...YL VGIKRQRRLY
      Hfgf4 EAELERRWES LVALSLARLP VAAQP..KEA AVQSGAGDYL LGIKRLRRLY
      Mfgf4 HAELGHGWDG LVARSLARLP VAAQP..PQA AVRSGAGDYL LGLKRLRRLY
      Hfgf3 ~MGLIWLLLL SLLEPGWPAA GPGARLRRDA GGRGGVYEHL GGAPRRRKLY
      Mfgf3 ~MGLIWLLLL SLLEPSWPTT GPGTRLRRDA GGRGGVYEHL GGAPRRRKLY
      Hfgf7 IICLVGTISL ACNDMTPEQM ATNVCSSPE RHTRSYDYME GGDIRVRRLF
      Mfgf7 LVCLVGTISL ACNDMSPEQT ATSVNCSSPE RHTRSYDYME GGDIRVRRLF
      Hfgf9 NVPVLPVDSP VLLSDHLGQS EAGGLPRGPA .VTDLDHLK. .GILRRRQLY
      Mfgf9 NVPVLPVDSP VLLNDHLGQS EAGGLPRGPA .VTDLDHLK. .GILRRRQLY
      Hfgf1 ~~~~~~~~~~ ~~~~~~MAEG EITTFTALTE ....KFNLPP GNYKKPKLLY
      Mfgf1 ~~~~~~~~~~ ~~~~~~MAEG EITTFAALTE ....RFNLPL GNYKKPKLLY
      Hfgf2 ~~~~~~~~~~ ~~~~~~MAAG SITTLPALPE .DGGSAFPP GHFKDPKRLY
      Mfgf2 ~~~~~~~~~~ ~~~~~~MAAS GITSLPALPE .DGGA.AFPP GHFKDPKRLY
       cons .sl....sl .l..s.a.a. fagv...gp. ...rssr.l.. ggikrvrrLy
```

Fig. 3B

```
              101                                                           150
hAgp-26257    TDDAQQTEAH LEIREDGTVG GAADQ.SPES LLQLKALKPG VIQILGVKTS
mAgp-26257    TDDDQDTEAH LEIREDGTVV GAAHR.SPES LLELKALKPG VIQILGVKAS
      Hfgf14  CR..QGY..Y LQMHPDGALD GTKDDSTNST LFNLIPVGLR VVAIQGVKTG
      Mfgf14  CR..QGY..Y LQMHPDGALD GTKDDSTNST LFNLIPVGLR VVAIQGVKTG
      Hfgf12  SQ..QGY..F LQMHPDGTID GTKDENSDYT LFNLIPVGLR VVAIQGVKAS
      Mfgf13  SR..QGY..H LQLQADGTID GTKDEDSTYT LFNLIPVGLR VVAIQGVQTK
       Hfgf5  CRVGIGF..H LQIYPDGKVN GSHE.ANMLS VLEIFAVSQG IVGIRGVFSN
       Mfgf5  CRVGIGF..H LQIYPDGKVN GSHE.ASVLS ILEIFAVSQG IVGIRGVFSN
       Hfgf6  CNVGIGF..H LQVLPDGRIS GTHE.ENPYS LLEISTVERG VVSLFGVRSA
       Mfgf6  CNVGIGF..H LQVPPDGRIS GTHE.ENPYS LLEISTVERG VVSLFGVKSA
       Hfgf4  CNVGIGF..H LQALPDGRIG GAHA.DTRDS LLELSPVERG VVSIFGVASR
       Mfgf4  CNVGIGF..H LQVLPDGRIG GVHA.DTRDS LLELSPVQRG VVSIFGVASR
       Hfgf3  CATK..Y..H LQLHPSGRVN GSLE.NSAYS ILEITAVEVG IVAIRGLFSG
       Mfgf3  CATK..Y..H LQLHPSGRVN GSLE.NSAYS ILEITAVEVG VVAIKGLFSG
       Hfgf7  CRTQ..W..Y LRIDKRGKVK GTQEMKNNYN IMEIRTVAVG IVAIKGVESE
       Mfgf7  CRTQ..W..Y LRIDKRGKVK GTQEMKNSYN IMEIRTVAVG IVAIKGVESE
       Hfgf9  CRT..GF..H LEIFPNGTIQ GTRKDHSRFG ILEFISIAVG LVSIRGVDSG
       Mfgf9  CRT..GF..H LEIFPNGTIQ GTRKDHSRFG ILEFISIAVG LVSIRGVDSG
       Hfgf1  CSNG.GH..F LRILPDGTVD GTRDRSDQHI QLQLSAESVG EVYIKSTETG
       Mfgf1  CSNG.GH..F LRILPDGTVD GTRDRSDQHI QLQLSAESAG EVYIKGTETG
       Hfgf2  CKNG.GF..F LRIHPDGRVD GVREKSDPHI KLQLQAEERG VVSIKGVCAN
       Mfgf2  CKNG.GF..F LRIHPDGRVD GVREKSDPHV KLQLQAEERG VVSIKGVCAN
        cons  cr.g.gf..h Lqihpdg.vd Gt.e.sspys llel.avevg vv.ikgvksg 151                                                           200
hAgp-26257    RFLCQRPDGA LYGSLHFDPE ACSFRELLLE DGYNVYQSEA HGLPLHLPGN
mAgp-26257    RFLCQQPDGA LYGSPHFDPE ACSFRELLLE DGYNVYQSEA HGLPLRLPQK
      Hfgf14  LYIAMNGEGY LYPSELFTPE .CKFKESVFE NYYVIYSSML YRQQESGRA.
      Mfgf14  LYIAMNGEGY LYPSELFTPE .CKFKESVFE NYYVIYSSML YRQQESGRA.
      Hfgf12  LYVAMNGEGY LYSSDVFTPE .CKFKESVFE NYYVIYSSTL YRQQESGRA.
      Mfgf13  LYLAMNSEGY LYTSEHFTPE .CKFKESVFE NYYVTYSSMI YRQQQSGRG.
       Hfgf5  KFLAMSKKGK LHASAKFTDD .CKFRERFQE NSYNTYASAI HRTEKTGRE.
       Mfgf5  KFLAMSKKGK LHASAKFTDD .CKFRERFQE NSYNTYASAI HRTEKTGRE.
       Hfgf6  LFVAMNSKGR LYATPSFQEE .CKFRETLLP NNYNAYESDL Y......QG.
       Mfgf6  LFIAMNSKGR LYTTPSFHDE .CKFRETLLP NNYNAYESDL Y......RG.
       Hfgf4  FFVAMSSKGK LYGSPFFTDE .CTFKEILLP NNYNAYESYK Y......PG.
       Mfgf4  FFVAMSSRGK LFGVPFFTDE .CKFKEILLP NNYNAYEAYA Y......PG.
       Hfgf3  RYLAMNKRGR LYASEHYSAE .CEFVERIHE LGYNTYASRL YRTVSSTPGA
       Mfgf3  RYLAMNKRGR LYASDHYNAE .CEFVERIHE LGYNTYASRL YRTGSSGPGA
       Hfgf7  FYLAMNKEGK LYAKKECNED .CNFKELILE NHYNTYASAK WTH..NG...
       Mfgf7  YYLAMNKEGK LYAKKECNED .CNFKELILE NHYNTYASAK WTH..SG...
       Hfgf9  LYLGMNEKGE LYGSEKLTQE .CVFREQFEE NWYNTYSSNL YKHVDTG...
       Mfgf9  LYLGMNEKGE LYGSEKLTQE .CVFREQFEE NWYNTYSSNL YKHVDTG...
       Hfgf1  QYLAMDTDGL LYGSQTPNEE .CLFLERLEE NHYNTYISKK H....AE...
       Mfgf1  QYLAMDTEGL LYGSQTPNEE .CLFLERLEE NHYNTYTSKK H....AE...
       Hfgf2  RYLAMKEDGR LLASKCVTDE .CFFFERLES NNYNTYRSRK Y....T....
       Mfgf2  RYLAMKEDGR LLASKCVTEE .CFFFERLES NNYNTYRSRK Y....S....
        cons  lylamnk.G. Lyasehft.e .CkF.Erlle nnYntY.s.l y....sg...
```

Fig. 3C

```
             201                                                              250
hAgp-26257   KSPHRDPAPR GPA...RFLP LPGLPPAPPE PPGILAPQPP DVGSSDPLSM
mAgp-26257   DSPNQDATSW GPV...RFLP MPGLLHEPQD QAGFLPPEPP DVGSSDPLSM
    Hfgf14   .........W FLGLNKEGQA MKG..NRVKK TKPAAHFLPK PLEVAMYREP
    Mfgf14   .........W FLGLNKEGQV MKG..NRVKK TKPAAHFLPK PLEVAMYREP
    Hfgf12   .........W FLGLNKEGQI MKG..NRVKK TKPSSHFVPK PIEVCMYREP
    Mfgf13   .........W YLGLNKEGEI MKG..NHVKK NKPAAHFLPK PLKVAMYKEP
     Hfgf5   .........W YVALNKRGKA KRGCSPRVKP QHISTHFLPR FKQSEQPELS
     Mfgf5   .........W YVALNKRGKA KRGCSPRVKP QHVSTHFLPR FKQSEQPELS
     Hfgf6   .........T YIALSKYGRV KRG..SKVSP IMTVTHFLPR I~~~~~~~~~
     Mfgf6   .........T YIALSKYGRV KRG..SKVSP IMTVTHFLPR I~~~~~~~~~
     Hfgf4   .........M FIALSKNGKT KKG..NRVSP TMKVTHFLPR L~~~~~~~~~
     Mfgf4   .........M FMALSKNGRT KKG..NRVSP TMKVTHFLPR L~~~~~~~~~
     Hfgf3   RRQPSAERLW YVSVNGKGRP RRG..FKTRR TQKSSLFLPR VLDHRDHEMV
     Mfgf3   QRQPGAQRPW YVSVNGKGRP RRG..FKTRR TQKSSLFLPR VLGHKDHEMV
     Hfgf7   .......GEM FVALNQKGIP VRG..KKTKK EQKTAHFLPM AIT~~~~~~~
     Mfgf7   .......GEM FVALNQKGIP VKG..KKTKK EQKTAHFLPM AIT~~~~~~~
     Hfgf9   .......RRY YVALNKDGTP REG..TRTKR HQKFTHFLPR PVDPDKVPEL
     Mfgf9   .......RRY YVALNKDGTP REG..TRTKR HQKFTHFLPR PVDPDKVPEL
     Hfgf1   .......KNW FVGLKKNGSC KRG..PRTHY GQKAILFLPL PVSSD~~~~~
     Mfgf1   .......KNW FVGLKKNGSC KRG..PRTHY GQKAILFLPL PVSSD~~~~~
     Hfgf2   ........SW YVALKRTGQY KLG..SKTGP GQKAILFLPM SAKS~~~~~~
     Mfgf2   ........SW YVALKRTGQY KLG..SKTGP GQKAILFLPM SAKS~~~~~~
      cons   .........w yvalnk.g.p krG..nr.kp tqkathflPr pv~s~~~~~~

251                                                              300
hAgp-26257   VGPSQGRSPS YAS~~~~~~~ ~~~~~~~~~~ ~~~~~~~~~~ ~~~~~~~~~~
mAgp-26257   VEPLQGRSPS YAS~~~~~~~ ~~~~~~~~~~ ~~~~~~~~~~ ~~~~~~~~~~
    Hfgf14   SLHDVGETVP KPGVTPSKST SASAIMNGGK PVNKSKTT~~ ~~~~~~~~~~
    Mfgf14   SLHDVGETVP KAGVTPSKST SASAIMNGGK PVNKCKTT~~ ~~~~~~~~~~
    Hfgf12   SLHEIGEKQG R.....SRKS SGTPTMNGGK VVNQDST~~~ ~~~~~~~~~~
    Mfgf13   SLHDLTEFSR SGSGTPTKSR SVSGVLNGGK SMSHNEST~~ ~~~~~~~~~~
     Hfgf5   FTVTVPEKKN PPSPIKSKIP LSAPRKNTNS VKYRLKFRFG ~~~~~~~~~~
     Mfgf5   FTVTVPEKKK P..PVKPKVP LSQPRRSPSP VKYRLKFRFG ~~~~~~~~~~
     Hfgf6   ~~~~~~~~~~ ~~~~~~~~~~ ~~~~~~~~~~ ~~~~~~~~~~ ~~~~~~~~~~
     Mfgf6   ~~~~~~~~~~ ~~~~~~~~~~ ~~~~~~~~~~ ~~~~~~~~~~ ~~~~~~~~~~
     Hfgf4   ~~~~~~~~~~ ~~~~~~~~~~ ~~~~~~~~~~ ~~~~~~~~~~ ~~~~~~~~~~
     Mfgf4   ~~~~~~~~~~ ~~~~~~~~~~ ~~~~~~~~~~ ~~~~~~~~~~ ~~~~~~~~~~
     Hfgf3   RQLQSGLPRP PGKGVQPRRR RQ.KQSPDNL EPSHVQASRL GSQLEASAH~
     Mfgf3   RLLQSSQPRA PGEGSQPRQR RQKKQSPGDH GKMETLSTRA TPSTQLHTGG
     Hfgf7   ~~~~~~~~~~ ~~~~~~~~~~ ~~~~~~~~~~ ~~~~~~~~~~ ~~~~~~~~~~
     Mfgf7   ~~~~~~~~~~ ~~~~~~~~~~ ~~~~~~~~~~ ~~~~~~~~~~ ~~~~~~~~~~
     Hfgf9   YKDILSQS~~ ~~~~~~~~~~ ~~~~~~~~~~ ~~~~~~~~~~ ~~~~~~~~~~
     Mfgf9   YKDILSQS~~ ~~~~~~~~~~ ~~~~~~~~~~ ~~~~~~~~~~ ~~~~~~~~~~
     Hfgf1   ~~~~~~~~~~ ~~~~~~~~~~ ~~~~~~~~~~ ~~~~~~~~~~ ~~~~~~~~~~
     Mfgf1   ~~~~~~~~~~ ~~~~~~~~~~ ~~~~~~~~~~ ~~~~~~~~~~ ~~~~~~~~~~
     Hfgf2   ~~~~~~~~~~ ~~~~~~~~~~ ~~~~~~~~~~ ~~~~~~~~~~ ~~~~~~~~~~
     Mfgf2   ~~~~~~~~~~ ~~~~~~~~~~ ~~~~~~~~~~ ~~~~~~~~~~ ~~~~~~~~~~
      cons   ~~~~~~~~~~ ~~~~~~~~~~ ~~~~~~~~~~ ~~~~~~~~~~ ~~~~~~~~~~
```

Fig. 3D

```
              301
  hAgp-26257  ~~~~
  mAgp-26257  ~~~~
      Hfgf14  ~~~~
      Mfgf14  ~~~~
      Hfgf12  ~~~~
      Mfgf13  ~~~~
       Hfgf5  ~~~~
       Mfgf5  ~~~~
       Hfgf6  ~~~~
       Mfgf6  ~~~~
       Hfgf4  ~~~~
       Mfgf4  ~~~~
       Hfgf3  ~~~~
       Mfgf3  LAVA
       Hfgf7  ~~~~
       Mfgf7  ~~~~
       Hfgf9  ~~~~
       Mfgf9  ~~~~
       Hfgf1  ~~~~
       Mfgf1  ~~~~
       Hfgf2  ~~~~
       Mfgf2  ~~~~
        cons  ~~~~
```

Fig. 4C

|   | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippo-campus | medulla oblonggata |
| B | occipital lobe | putamen | substantia nigra | temporal lobe | thalamus | nucleus accumbeus | spinal cord | |
| C | heart | aorta | skeletal muscle | colon | bladder | uterus | prostate | stomach |
| D | testis | ovary | pancreas | pituitary gland | adrenal gland | thyroid gland | salivary gland | mammary gland |
| E | kidney | liver | small intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast T-RNA 100 ng | yeast tRNA 100 ng | E. coli rRNA 100 ng | E. coli DNA 100 ng | Poly-(A) 100 ng | human Cot1DNA 100 ng | human DNA 100 ng | human DNA 500 ng |

NUCLEIC ACID MOLECULES ENCODING FIBROBLAST GROWTH FACTOR-LIKE POLYPEPTIDES

This application is a continuation of U.S. application Ser. No. 09/391,861, filed on Sep. 7, 1999, which issued as U.S. Pat. No. 7,408,047 on Aug. 5, 2008, the disclosure of which is explicitly incorporated by reference herein.

FIELD OF THE INVENTION

The present invention relates to novel Fibroblast Growth Factor-like (FGF-like) polypeptides and nucleic acid molecules encoding the same. The invention also relates to vectors, host cells, antibodies and methods for producing FGF-like polypeptides. Also provided for are methods for the diagnosis and treatment of diseases associated with FGF-like polypeptides.

BACKGROUND OF THE INVENTION

Technical advances in the identification, cloning, expression, and manipulation of nucleic acid molecules have greatly accelerated the discovery of novel therapeutics based upon deciphering the human genome. Rapid nucleic acid sequencing techniques can now generate sequence information at unprecedented rates and, coupled with computational analyses, allow the assembly of overlapping sequences into entire genomes and the identification of polypeptide-encoding regions. Comparison of a predicted amino acid sequence against a database compilation of known amino acid sequences can allow one to determine the extent of homology to previously identified sequences and/or structural landmarks. Cloning and expression of a polypeptide-encoding region of a nucleic acid molecule provides a polypeptide product for structural and functional analysis. Manipulation of nucleic acid molecule and encoded polypeptides to give variants and derivatives thereof may confer advantageous properties on a product for use as a therapeutic.

In spite of the significant technical advances in genome research over the past decade, the potential for development of novel therapeutics based on the human genome is still largely unrealized. Genes encoding potentially beneficial protein therapeutics, or those encoding polypeptides that may act as "targets" for therapeutic molecules, have still not been identified. In addition, structural and functional analyses of polypeptide products from many human genes have not been undertaken.

Accordingly, it is an object of the invention to identify novel polypeptides and nucleic acid molecules encoding the same which have diagnostic or therapeutic benefit.

SUMMARY OF THE INVENTION

The present invention relates to novel FGF-like nucleic acid molecules and encoded polypeptides.

The invention provides for an isolated nucleic acid molecule comprising a nucleotide sequence selected from the group consisting of:

(a) the nucleotide sequence as set forth in SEQ ID NO: 1 or SEQ ID NO: 3;

(b) a nucleotide sequence encoding the polypeptide as set forth in SEQ ID NO: 2 or SEQ ID NO: 4;

(c) a nucleotide sequence encoding a polypeptide that is at least about 80, 85, 90, 95, 96, 97, 98, or 99 percent identical to the polypeptide as set forth in SEQ ID NO: 2 or SEQ ID NO: 4 wherein the polypeptide activates one or more FGF receptors, regulates the growth and differentiation of cells within the liver, regulates other cell types following secretion from the liver, plays a role in liver chemotaxis, has an oncogenic activity, or serves as an antigen for generating antibodies;

(d) an allelic variant or splice variant of any of (a), (b) or (c);

(e) the nucleotide sequence of the DNA insert in ATCC Deposit No. PTA-626;

(f) a nucleotide sequence of (b), (c), or (d) encoding a polypeptide fragment of at least about 25 amino acid residues wherein the polypeptide fragment activates one or more FGF receptors, regulates the growth and differentiation of cells within the liver, regulates other cell types following secretion from the liver, plays a role in liver chemotaxis, has an oncogenic activity, or serves as an antigen for generating antibodies;

(g) a nucleotide sequence of (a), (b), or (c) comprising a fragment of at least about 16 to 18 nucleotides;

(h) a nucleotide sequence encoding a polypeptide that has a substitution and/or deletion of 1 to 100 amino acid residues in the amino acid sequence as set forth in either SEQ ID NO: 2 or SEQ ID NO: 4 wherein the polypeptide activates one or more FGF receptors, regulates the growth and differentiation of cells within the liver, regulates other cell types following secretion from the liver, plays a role in liver chemotaxis, has an oncogenic activity, or serves as an antigen for generating antibodies;

(i) a nucleotide sequence which hybridizes under stringent conditions to the complement of any of (a)-(h); and (j) a nucleotide sequence complementary to any of (a), (b), (c), or (i).

The invention also provides for an isolated polypeptide comprising the amino acid sequence selected from the group consisting of:

(a) the amino acid sequence as set forth in SEQ ID NO: 2 or SEQ ID NO: 4;

(b) the mature amino acid sequence as set forth in SEQ ID NO: 5 or SEQ ID NO: 6 comprising a mature amino terminus at residue 29 in the mature human amino acid sequence and at residue 30 in the mature mouse amino acid sequence, optionally further comprising an amino-terminal methionine;

(c) a fragment of the amino acid sequence set forth in SEQ ID NO: 2 or SEQ ID NO: 4 comprising at least about 25 amino acid residues wherein the fragment activates one or more FGF receptors, regulates the growth and differentiation of cells within the liver, regulates other cell types following secretion from the liver, plays a role in liver chemotaxis, has an oncogenic activity, or serves as an antigen for generating antibodies;

(d) the amino acid sequence encoded by the DNA insert of ATCC Deposit No. PTA-626;

(e) an ortholog of SEQ ID NO: 2 or SEQ ID NO: 4; and (f) an allelic variant or splice variant of (a), (b), (d), or (e).

The invention also provides for an expression vector comprising the nucleic acid molecules as set forth above, host cells comprising the expression vectors of the invention, and a method of production of an FGF-like polypeptide comprising culturing the host cells and optionally isolating the polypeptide so produced.

A transgenic non-human animal comprising a nucleic acid molecule encoding an FGF-like polypeptide is also encompassed by the invention. The FGF-like nucleic acid molecules are introduced into the animal in a manner that allows expression and increased levels of an FGF-like polypeptide, which may include increased circulating levels. Alternatively, the FGF-like nucleic acid molecules are introduced into the animal in a manner that prevents expression of endogenous FGF-like polypeptide (i.e., generates a transgenic animal possessing an FGF-like polypeptide gene knockout). The transgenic non-human animal is preferably a mammal, and more preferably a rodent, such as a rat or a mouse. Preferably the FGF-like transgene is expressed in the liver under the control of the apolioprotein E promoter, or ubiquitously under the control of the beta actin promoter. At 6-8 weeks of age, the transgenic mice demonstrate an abnormal phenotype generally characterized as inhibited or delayed maturation. This includes reduced body weight, reduced liver weight as percent of body weight, reduced spleen weight as percent of body weight, increased thymic weight as percent of body weight (possibly due to delayed thymic maturation and involution), and poorly developed ovaries with lack of significant follicular development.

Also provided are derivatives of the FGF-like polypeptides of the invention, fusion polypeptides comprising the FGF-like polypeptides of the invention, and antibodies specifically binding the FGF-like polypeptides of the invention.

Compositions comprising the nucleotides or polypeptides of the invention and a carrier, adjuvant, solubilizer, stabilizer or anti-oxidant, or other pharmaceutically acceptable agent are also encompassed by the invention. The compositions may include pharmaceutical compositions comprising therapeutically effective amounts of the nucleotides or polypeptides of the invention, and methods of using the polypeptides and nucleic acid molecules.

Surprisingly, FGF-like polypeptide appeared to be primarily expressed in the liver, thereby distinguishing it from all other members of the FGF family. The present polypeptide, and its useful nucleic acid intermediates, may have utility, therefore, in differentiating liver cells from background. Further, given the localization of FGF-like polypeptide expression, the structural similarity of FGF-like polypeptide to members of the FGF family, and the likelihood that FGF-like polypeptide is secreted into the bloodstream where it may exert effects on distal sites, the present polypeptides may provide benefits in the stimulation of cells within or near the liver, regulation of intestinal cell activity, stimulation of pancreatic beta islet cells, regulation of neuronal cells, stimulation or inhibition of angiogenesis, stimulation of epithelium or mesenchymal components of granulation tissue, stimulation of corneal epithelium, lens, or retinal tissue, regeneration of renal tubules, hematopoietic cell regulation, regulation of hair follicle growth, or regulation of pulmonary epithelium, particularly as a therapeutic pharmaceutical composition.

FGF-like polypeptides may also be useful as growth or fat deposition inhibitors, and therefore may be useful in the treatment of obesity or diabetes. Inhibitors—such as antibodies, binding proteins or small molecules—that interfere with the interaction of FGF-like polypeptides and their receptor(s) may be useful in stimulating body growth and maturation. Therefore, such inhibitors may be useful in treating short stature, delayed maturation, or other conditions generally associated with impairment of signaling of growth hormone or its mediator, insulin-like growth factor.

The FGF-like polypeptides and nucleic acid molecules of the invention may be used for therapeutic or diagnostic purposes to treat, prevent and/or detect a medical condition such as cirrhosis or other toxic insult of the liver; inflammatory bowel disease, mucositis, Crohn's disease, or other gastrointestinal abnormality; diabetes; neurodegenerative diseases; wounds; damage to the corneal epithelium, lens, or retinal tissue; damage to renal tubules as a result of acute tubular necrosis; hematopoietic cell reconstitution following chemotherapy; multiple sclerosis; alopecia; diseases or abnormalities of androgen target organs; infantile respiratory distress syndrome, bronchopulmonary dysplasia, acute respiratory distress syndrome, or other lung abnormalities; or tumors of the eye or other tissues. The invention provides for treating, preventing or ameliorating a disorder comprising administering to an animal an FGF-like polypeptide. The invention also provides for a method of diagnosing such a disorder or a susceptibility to such a disorder in an animal which includes both determining the presence or amount of expression of an FGF-like polypeptide and diagnosing such a disorder or a susceptibility to such a disorder based on the presence or amount of expression of an FGF-like polypeptide. The animal is preferably a mammal, and more preferably a human. The present invention also relates to methods for the manufacture of a medicament for the treatment of a disorder such as those mentioned above.

The invention also provides for the use of antibodies or other inhibitors of the binding of FGF-like polypeptide to its receptor for the treatment of the same diseases listed above, and for the treatment of tumors.

The invention also provides for a method of identifying a test molecule which binds to an FGF-like polypeptide wherein the method comprises contacting an FGF-like polypeptide with a test molecule and determining the extent of binding of the test molecule to the polypeptide. The method further comprises determining whether such test molecules are agonists or antagonists of an FGF-like polypeptide.

The invention also provides for a method of testing the impact of molecules on the expression of FGF-like polypeptide or on the activity of FGF-like polypeptide.

A method of regulating expression and modulating (i.e., increasing or decreasing) levels of an FGF-like polypeptide are also encompassed by the invention. One method comprises administering to an animal a nucleic acid molecule encoding an FGF-like polypeptide. In another method, a nucleic acid molecule comprising elements that regulate expression of an FGF-like polypeptide may be administered. Examples of these methods include gene therapy and anti-sense therapy.

DESCRIPTION OF THE FIGURES

FIG. 1 illustrates the nucleotide sequence of the murine FGF-like gene (SEQ ID NO: 3) and the deduced amino acid sequence of murine FGF-like protein (SEQ ID NO: 4);

FIGS. 2A-2B illustrate the nucleotide sequence of the human FGF-like gene (SEQ ID NO: 1) and the deduced amino acid sequence of human FGF-like protein (SEQ ID NO: 2);

FIGS. 3A-3D illustrate the amino acid sequence alignment of human FGF-like protein (hAgp-26257; SEQ ID NO: 2), murine FGF-like protein (mAgp-26257; SEQ ID NO: 4), human FGF-14 (Hfgf14; SEQ ID NO: 16), murine FGF-14 (Mfgf14; SEQ ID NO: 26), human FGF-12 (Hfgf12; SEQ ID NO: 15), murine FGF-13 (Mfgf13; SEQ ID NO: 25), human FGF-5 (Hfgf5; SEQ ID NO: 20), murine FGF-5 (Mfgf5; SEQ ID NO: 30), human FGF-6 (Hfgf6; SEQ ID NO: 21), murine FGF-6 (Mfgf6; SEQ ID NO: 31), human FGF-4 (Hfgf4; SEQ ID NO: 19), murine FGF-4 (Mfgf4; SEQ ID NO: 29), human FGF-3 (Hfgf3; SEQ ID NO: 18), murine FGF-3 (Mfgf3; SEQ ID NO: 28), human FGF-7 (Hfgf7; SEQ ID NO: 22), murine FGF-7 (Mfgf7; SEQ ID NO: 32), human FGF-9 (Hfgf9; SEQ ID NO: 23), murine FGF-9 (Mfgf9; SEQ ID NO: 33), human FGF-1 (Hfgf1; SEQ ID NO: 14), murine FGF-1 (Mfgf1; SEQ ID NO: 24), human FGF-2 (Hfgf2; SEQ ID NO: 17), murine FGF-2 (Mfgf2; SEQ ID NO: 27), and the resulting FGF consensus sequence (cons);

FIGS. 4A-4C illustrate the results of (A) a Northern blot analysis of murine FGF-like polypeptide expression, (B) a Northern blot analysis of human FGF-like polypeptide expression, and (C) a dot blot analysis of human FGF-like polypeptide expression.

DETAILED DESCRIPTION OF THE INVENTION

Figure 4A:
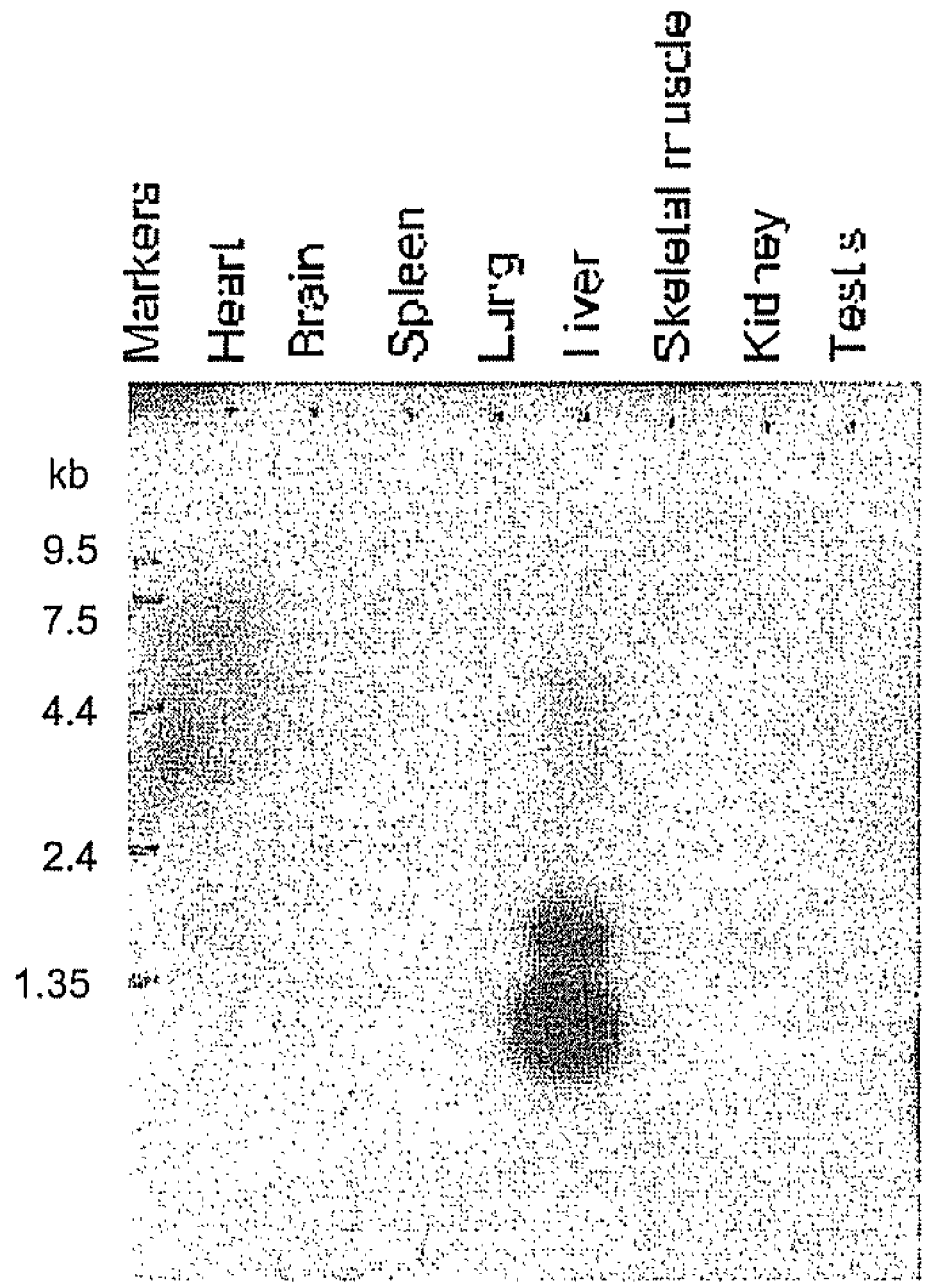

The section headings herein are for organizational purposes only and are not to be construed as limiting the subject matter described therein. All references cited in this application are expressly incorporated by reference herein.

Definitions

The term "FGF-like nucleic acid molecule" refers to a nucleic acid molecule comprising or consisting essentially of a nucleotide sequence as set forth in SEQ ID NO: 1 or SEQ ID NO: 3, comprising or consisting essentially of a nucleotide sequence encoding the polypeptide as set forth in SEQ ID NO: 2 or SEQ ID NO: 4, comprising or consisting essentially of a nucleotide sequence of the DNA insert in ATCC Deposit No. PTA-626, or nucleic acid molecules related thereto.

Related nucleic acid molecules comprise or consist essentially of a nucleotide sequence that is about 80 percent identical to the nucleotide sequence as shown in SEQ ID NO: 1 or SEQ ID NO: 3, or comprise or consist essentially of a nucleotide sequence encoding a polypeptide that is about 80 percent identical to the polypeptide as set forth in SEQ ID NO: 2 or SEQ ID NO: 4. In preferred embodiments, the nucleotide sequences are about 85 percent, or about 90 percent, or about 95 percent, or about 96, 97, 98, or 99 percent identical to the nucleotide sequence as shown in SEQ ID NO: 1 or SEQ ID NO: 3, or the nucleotide sequences encode a polypeptide that is about 85 percent, or about 90 percent, or about 95 percent, or about 96, 97, 98, or 99 percent identical to the polypeptide sequence as set forth in SEQ ID NO: 2 or SEQ ID NO: 4. Related nucleic acid molecules also include fragments of the above FGF-like nucleic acid molecules which are at least about 16 contiguous nucleotides, or about 18, or about 20, or about 25, or about 50, or about 75, or about 100, or greater than about 100 contiguous nucleotides. Related nucleic acid molecules also include fragments of the above FGF-like nucleic acid molecules which encode a polypeptide of at least about 25 amino acid residues, or about 50, or about 75, or about 100, or greater than about 100 amino acid residues. Related nucleic acid molecules also include a nucleotide sequence encoding a polypeptide comprising or consisting essentially of a substitution, modifications and/or a deletion of 1 to 100 amino acid residues compared to the polypeptide in SEQ ID NO: 2 or SEQ ID NO: 4. Related FGF-like nucleic acid molecules include those molecules that comprise nucleotide sequences which hybridize under moderately or highly stringent conditions as defined herein with the complements of any of the above nucleic acid molecules. In preferred embodiments, the related nucleic acid molecules comprise sequences which hybridize under moderately or highly stringent conditions with the sequence as shown in SEQ ID NO: 1 or SEQ ID NO: 3, or with a molecule encoding a polypeptide, which polypeptide comprises the sequence as shown in SEQ ID NO: 2 or SEQ ID NO: 4, or with a nucleic acid fragment as defined above, or with a nucleic acid fragment encoding a polypeptide as defined above. It is also understood that related nucleic acid molecules include allelic or splice variants of any of the above nucleic acids, and include sequences which are complementary to any of the above nucleotide sequences.

The term "isolated nucleic acid molecule" refers to a nucleic acid molecule of the invention that is free from at least one contaminating nucleic acid molecule with which it is naturally associated, and preferably substantially free from any other contaminating mammalian nucleic acid molecules which would interfere with its use in protein production or its therapeutic or diagnostic use.

The term "allelic variant" refers to one of several possible naturally occurring alternate forms of a gene occupying a given locus on a chromosome of an organism or a population of organisms.

The term "splice variant" refers to a nucleic acid molecule, usually RNA, which is generated by alternative processing of intron sequences in an RNA transcript.

The term "expression vector" refers to a vector that is suitable for propagation in a host cell and contains nucleic acid sequences that direct and/or control the expression of inserted heterologous nucleic acid sequences. Expression includes, but is not limited to, processes such as transcription, translation, and RNA splicing, if introns are present.

The term "highly stringency conditions" refers to those conditions that (1) employ low ionic strength reagents and high temperature for washing, for example, 0.015 M NaCl/ 0.0015 M sodium citrate/0.1% NaDodSO$_4$ (SDS) at 50° C., or (2) employ during hybridization a denaturing agent such as formamide, for example, 50% (vol/vol) formamide with 0.1% bovine serum albumin, 0.2% Ficoll, 0.1% polyvinylpyrrolidone, 50 mM sodium phosphate buffer (pH 6.5), 750 mM NaCl, and 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

The term "moderately stringency conditions" refers to conditions which generally include the use of a washing solution and hybridization conditions (e.g., temperature, ionic strength, and percentage of SDS) less stringent than described above. An example of moderately stringent conditions are conditions such as overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate, and 20 μl/ml denatured sheared salmon sperm DNA, followed by washing in 1×SSC at about 37-50° C. The skilled artisan will recognize how to adjust the temperature, ionic strength, etc. as necessary to accommodate factors such as probe length and the like.

In certain preferred embodiments, where oligonucleotide probes are used to screen cDNA or genomic libraries, high stringency conditions are used which depend upon the melting temperature ($T_m$) of oligonucleotide probes to target sequences. The $T_m$ may be estimated using the following formula (Bolton et al., *Proc. Natl. Acad. Sci. U.S.A.* 48:1390 (1962)):

$$T_m = 81.5 - 16.6(\log [Na+]) + 0.41(\%G+C) - (600/N)$$

wherein [Na+] is the sodium ion concentration in the hybridization (or washing) solution;

% G+C is guanine and cytosine content in the oligonucleotide probe; and

N is the probe length in nucleotides.

An example of a high stringency solution is 6×SSC and 0.05% sodium pyrophosphate at a temperature of 35-63° C., depending on the length of the oligonucleotide probe. For example, according to certain embodiments, 14 base pair probes are washed at 35-40° C., 17 base pair probes are washed at 45-50° C., 20 base pair probes are washed at 52-57° C., and 23 base pair probes are washed at 57-63° C. The temperature can be increased 2-3° C. where the background non-specific binding appears high. A second high stringency solution utilizes tetramethylammonium chloride (TMAC) for washing oligonucleotide probes. One stringent washing solution is 3 M TMAC, 50 mM Tris-HCl, pH 8.0, and 0.2% SDS. The washing temperature using this solution is a function of the length of the probe. For example, 14 base pair probes are washed at 35-40° C., 17 base pair probes are washed at about 45-50° C., 20 base pair probes are washed at 52-57° C., and 23 base pair probes are washed at 57-63° C.

The term "FGF-like polypeptides" refers to a polypeptide comprising the amino acid sequence of SEQ ID NO: 2 or SEQ ID NO: 4, and related polypeptides described herein. Related polypeptides include: allelic variants; splice variants; fragments; derivatives; substitution, deletion, and insertion variants; fusion polypeptides; and orthologs. FGF-like polypeptides may be mature polypeptides, as defined herein, and may or may not have an amino terminal methionine residue, depending on the method by which they are prepared.

The term "FGF-like polypeptide fragment" refers to a peptide or polypeptide that comprises less than the full length amino acid sequence of an FGF-like polypeptide as set forth in SEQ ID NO: 2 or SEQ ID NO: 4. Such a fragment may arise, for example, from a truncation at the amino terminus, a truncation at the carboxyl terminus, and/or an internal deletion of a residue(s) from the amino acid sequence. FGF-like fragments may result from alternative RNA splicing or from in vivo protease activity.

The term "FGF-like polypeptide variants" refers to FGF-like polypeptides comprising amino acid sequences which contain one or more amino acid sequence substitutions, deletions, and/or additions as compared to the FGF-like polypeptide amino acid sequence set forth in SEQ ID NO: 2 or SEQ ID NO: 4. Variants may be naturally occurring or artificially constructed. Such FGF-like polypeptide variants may be prepared from the corresponding nucleic acid molecules encoding said variants, which have a DNA sequence that varies accordingly from the DNA sequences for wild type FGF-like polypeptides as set forth in SEQ ID NO: 1 or SEQ ID NO: 3.

The term "FGF-like fusion polypeptide" refers to a fusion of an FGF-like polypeptide, fragment, variant, or derivative thereof, with a heterologous peptide or polypeptide.

The term "FGF-like polypeptide derivatives" refers to FGF-like polypeptides, variants, or fragments thereof, that have been chemically modified, as for example, by covalent attachment of one or more polymers, including, but not limited to, water soluble polymers, N-linked or O-linked carbohydrates, sugars, phosphates, and/or other such molecules. The derivatives are modified in a manner that is different from naturally occurring FGF-like polypeptide, either in the type or location of the molecules attached to the polypeptide. Derivatives further include the deletion of one or more chemical groups naturally attached to the FGF-like polypeptide.

The terms "biologically active FGF-like polypeptides," "biologically active FGF-like polypeptide fragments," "biologically active FGF-like polypeptide variants," and "biologically active FGF-like polypeptide derivatives" refer to FGF-like polypeptides having at least one activity characteristic of an FGF-like polypeptide, such as regulation of intestinal cell activity, stimulation of pancreatic beta islet cells, regulation of neuronal cells, stimulation or inhibition of angiogenesis, stimulation of epithelium or mesenchymal components of granulation tissue, stimulation of corneal epithelium, lens, or retinal tissue, regeneration of renal tubules, hematopoietic cell regulation, regulation of hair follicle growth, regulation of pulmonary epithelium, or stimulation of either epithelial, mesenchymal, hematopoietic, or neuronal cells or tissues. In general, FGF-like polypeptides, and variants, fragments and derivatives thereof, will have at least one activity characteristic of an FGF-like polypeptide such as those activities listed above. In addition, an FGF-like polypeptide may be active as an immunogen (i.e., the polypeptide contains at least one epitope to which antibodies may be raised).

"Naturally occurring" when used in connection with biological materials such as nucleic acid molecules, polypeptides, host cells, and the like, refers to that which are found in nature and not manipulated by a human being.

The term "isolated polypeptide" refers to a polypeptide of the invention that is free from at least one contaminating polypeptide that is found in its natural environment, and preferably substantially free from any other contaminating mammalian polypeptides which would interfere with its therapeutic or diagnostic use.

The term "ortholog" refers to a polypeptide that corresponds to a polypeptide identified from a different species. For example, murine and human FGF-like polypeptides are considered orthologs of one another.

The term "mature FGF-like polypeptide" refers to a polypeptide lacking a leader sequence and may also include other modifications of a polypeptide such as proteolytic processing of the amino terminus (with or without a leader sequence) and/or the carboxyl terminus, cleavage of a smaller polypeptide from a larger precursor, N-linked and/or O-linked glycosylation, and other post-translational modifications understood by those with skill in the art.

The terms "effective amount" and "therapeutically effective amount" refer to the amount of a FGF-like polypeptide that is useful or necessary to support an observable level of one or more biological activities of the FGF-like polypeptides as set forth above.

Relatedness of Nucleic Acid Molecules and/or Polypeptides

The term "identity," as known in the art, refers to a relationship between the sequences of two or more polypeptide molecules or two or more nucleic acid molecules, as determined by comparing the sequences. In the art, "identity" also means the degree of sequence relatedness between polypeptide or nucleic acid molecule sequences, as the case may be, as determined by the match between strings of nucleotide or amino acid sequences. "Identity" measures the percent of identical matches between two or more sequences with gap alignments addressed by a particular mathematical model of computer programs (i.e., "algorithms").

The term "similarity" is a related concept, but in contrast to "identity," refers to a measure of similarity which includes both identical matches and conservative substitution matches. Since conservative substitutions apply to polypeptides and not nucleic acid molecules, similarity only deals with polypeptide sequence comparisons. If two polypeptide sequences have, for example, 10 out of 20 identical amino acids, and the remainder are all non-conservative substitutions, then the percent identity and similarity would both be 50%. If in the same example, there are 5 more positions where there are conservative substitutions, then the percent identity remains 50%, but the percent similarity would be 75% (15 out of 20). Therefore, in cases where there are conservative substitutions, the degree of similarity between two polypeptide sequences will be higher than the percent identity between those two sequences.

The term "conservative amino acid substitution" refers to a substitution of a native amino acid residue with a normative residue such that there is little or no effect on the polarity or charge of the amino acid residue at that position. For example, a conservative substitution results from the replacement of a non-polar residue in a polypeptide with any other non-polar residue. Furthermore, any native residue in the polypeptide may also be substituted with alanine, as has been previously described for "alanine scanning mutagenesis" (Cunnigham et al., *Science* 244:1081-85 (1989)). General rules for conservative amino acid substitutions are set forth in Table I.

TABLE I

Conservative Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn | Arg |
| Met | Leu, Phe, Ile | Leu |
| Phe | Leu, Val, Ile, Ala, Tyr | Leu |
| Pro | Ala | Ala |
| Ser | Thr | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Conservative modifications to the amino acid sequence (and the corresponding modifications to the encoding nucleotides) are expected to produce FGF-like polypeptide having functional and chemical characteristics similar to those of naturally occurring FGF-like polypeptide. In contrast, substantial modifications in the functional and/or chemical characteristics of FGF-like polypeptide may be accomplished by selecting substitutions that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain. Naturally occurring residues may be divided into groups based on common side chain properties:

1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class. Such substituted residues may be introduced into regions of the human FGF-like molecule that are homologous with non-human FGF-like polypeptide, or into the non-homologous regions of the molecule.

Identity and similarity of related nucleic acid molecules and polypeptides can be readily calculated by known methods, including but not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of sequence Data* (Part 1, A. M. Griffin and H. G. Griffin, eds., Humana Press 1994); G. von Heinle, *Sequence Analysis in Molecular Biology* (Academic Press 1987); Sequence Analysis Primer (M. Gribskov and J. Devereux, eds., M. Stockton Press 1991); and Carillo et al., *SIAM J. Applied Math.* 48:1073 (1988).

Preferred methods to determine identity and/or similarity are designed to give the largest match between the sequences tested. Methods to determine identity and similarity are codified in publicly available computer programs. Preferred computer program methods to determine identity and similarity between two sequences include, but are not limited to, the GCG program package, including GAP (Devereux et al., *Nuc. Acids Res.* 12:387 (1984); Genetics Computer Group, University of Wisconsin, Madison, Wis.), BLASTP, BLASTN, and FASTA (Atschul et al., *J. Mol. Biol.* 215:403-10 (1990)). The BLAST X program is publicly available from the National Center for Biotechnology Information (NCBD and other sources (Altschul et al., *BLAST Manual* (NCB NLM NIH, Bethesda, Md.); Altschul et al., 1990, supra). The well-known Smith Waterman algorithm may also be used to determine identity.

By way of example, using the computer algorithm GAP (Genetics Computer Group), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix (see Dayhoff et al., 5 *Atlas of Protein Sequence and Structure* (Supp. 3 1978) for the PAM250 comparison matrix; see Henikoff et al., *Proc. Natl. Acad. Sci USA* 89:10915-19 (1992) for the BLOSUM 62 comparison matrix) is also used by the algorithm.

Preferred parameters for polypeptide sequence comparison include the following:

Algorithm: Needleman and Wunsch, *J. Mol. Biol.* 48:443-53 (1970)

Comparison matrix: BLOSUM 62 from Henikoff et al., *Proc. Natl. Acad. Sci. U.S.A.* 89:10915-19 (1992)
Gap Penalty: 12
Gap Length Penalty: 4
Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
Algorithm: Needleman et al., *J. Mol. Biol.* 48:443-53 (1970)
Comparison matrix: matches=+10, mismatch=0
Gap Penalty: 50
Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used by those of skill in the art, including those set forth in the Program Manual, Wisconsin Package, Version 9, September, 1997. The particular choices to be made will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

Sequence analysis of an isolated mouse cDNA (murine FGF-like protein; SEQ ID NO: 3) indicated that it encoded a novel member of the FGF family of proteins. The murine FGF-like gene comprises a 630 bp open reading frame encoding a protein of 210 amino acids (FIG. 1). The murine sequence was used to identify the human FGF-like ortholog. Sequence analysis of four human FGF-like polypeptide cDNA clones indicated that the human FGF-like gene comprises a 627 bp open reading frame encoding a protein of 209 amino acids (FIGS. 2A-2B).

FIGS. 3A-3D illustrate the amino acid sequence alignment of human FGF-like protein, murine FGF-like protein, and other members of the FGF family. Computer analysis of the predicted murine FGF-like polypeptide, using the FASTA program of the Swissprot database, indicated that the protein was most closely related to murine FGF-6, FGF-15, and FGF-4. Using the GAP program, murine FGF-like polypeptide was found to be 32% identical to murine FGF-6 and 28% identical to murine FGF-4. Computer analysis also indicated that the murine FGF-like polypeptide, similar to FGF-6, FGF-4, and FGF-15 but in contrast to FGF-1 and FGF-2, possessed a potential signal peptide at its amino terminus. The murine FGF-like polypeptide is 79% identical to the human FGF-like protein.

Nucleic Acid Molecules

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994).

The invention provides for nucleic acid molecules as described herein and methods for obtaining the molecules. A gene or cDNA encoding an FGF-like polypeptide or fragment thereof may be obtained by hybridization screening of a genomic or cDNA library, or by PCR amplification. Probes or primers useful for screening a library by hybridization can be generated based on sequence information for other known genes or gene fragments from the same or a related family of genes, such as, for example, conserved motifs. In addition, where a gene encoding FGF-like polypeptide has been identified from one species, all or a portion of that gene may be used as a probe to identify corresponding genes from other species (orthologs) or related genes from the same species (homologs). The probes or primers may be used to screen cDNA libraries from various tissue sources believed to express the FGF-like gene. In addition, part or all of a nucleic acid molecule having the sequence as set forth in SEQ ID NO: 1 or SEQ ID NO: 3 may be used to screen a genomic library to identify and isolate a gene encoding FGF-like polypeptide. Typically, conditions of moderate or high stringency will be employed for screening to minimize the number of false positives obtained from the screen.

Nucleic acid molecules encoding FGF-like polypeptides may also be identified by expression cloning which employs detection of positive clones based upon a property of the expressed protein. Typically, nucleic acid libraries are screened by binding an antibody or other binding partner (e.g., receptor or ligand) to cloned proteins which are expressed and displayed on the host cell surface. The antibody or binding partner is modified with a detectable label to identify those cells expressing the desired clone.

Another means of preparing a nucleic acid molecule encoding an FGF-like polypeptide or fragment thereof is chemical synthesis using methods well known to the skilled artisan such as those described by Engels et al., *Angew. Chem. Intl. Ed.* 28:716-34 (1989). These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the FGF-like polypeptide will be several hundred nucleotides in length. Nucleic acids larger than about 100 nucleotides can be synthesized as several fragments using these methods. The fragments can then be ligated together to form the full-length FGF-like polypeptide. Usually, the DNA fragment encoding the amino terminus of the polypeptide will have an ATG, which encodes a methionine residue. This methionine may or may not be present on the mature form of the FGF-like polypeptide, depending on whether the polypeptide produced in the host cell is designed to be secreted from that cell.

In some cases, it may be desirable to prepare nucleic acid molecules encoding FGF-like polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

In certain embodiments, nucleic acid variants contain codons which have been altered for optimal expression of an FGF-like polypeptide in a given host cell. Particular codon alterations will depend upon the FGF-like polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Ecohigh._Cod" for codon preference of highly expressed bacterial genes may be used and are provided by the University of Wisconsin Package Version 9.0, Genetics Computer Group, Madison, Wis. Other useful codon frequency tables include "Celegans_high.cod," "Celegans_low.cod," "*Drosophila_* high.cod," "Human_high.cod," "Maize_high.cod," and "Yeast_high.cod."

In other embodiments, nucleic acid molecules encode FGF-like variants with conservative amino acid substitutions as defined above, FGF-like variants comprising an addition and/or a deletion of one or more N-linked or O-linked glycosylation sites, FGF-like variants having deletions and/or substitutions of one or more cysteine residues, or FGF-like polypeptide fragments as described above. In addition, nucleic acid molecules may encode any combination of FGF-like variants, fragments, and fusion polypeptides described herein.

Vectors and Host Cells

A nucleic acid molecule encoding an FGF-like polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding an FGF-like polypeptide may be amplified/expressed in prokaryotic, yeast, insect (baculovirus systems) and/or eukaryotic host cells. Selection of the host cell will depend in part on whether an FGF-like polypeptide is to be post-translationally modified (e.g., glycosylated and/or phosphorylated). If so, yeast, insect, or mammalian host cells are preferable. For a review of expression vectors, see 185 *Meth. Enz.* (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotides: a promoter, one or more enhancer sequences, an origin of replication, a transcriptional termination sequence, a complete intron sequence containing a donor and acceptor splice site, a leader sequence for secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag" sequence, i.e., an oligonucleotide molecule located at the 5' or 3' end of the FGF-like polypeptide coding sequence; the oligonucleotide molecule encodes polyHis (such as hexaHis), or other "tag" such as FLAG, HA (hemaglutinin Influenza virus) or myc for which commercially available antibodies exist. This tag is typically fused to the polypeptide upon expression of the polypeptide, and can serve as a means for affinity purification of the FGF-like polypeptide from the host cell. Affinity purification can be accomplished, for example, by column chromatography using antibodies against the tag as an affinity matrix. Optionally, the tag can subsequently be removed from the purified FGF-like polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or native sequences which normally function to regulate FGF-like expression. As such, the source of flanking sequences may be any prokaryotic or eukaryotic organism, any vertebrate or invertebrate organism, or any plant, provided that the flanking sequences is functional in, and can be activated by, the host cell machinery.

The flanking sequences useful in the vectors of this invention may be obtained by any of several methods well known in the art. Typically, flanking sequences useful herein other than the FGF-like gene flanking sequences will have been previously identified by mapping and/or by restriction endonuclease digestion and can thus be isolated from the proper tissue source using the appropriate restriction endonucleases. In some cases, the full nucleotide sequence of one or more flanking sequence may be known. Here, the flanking sequence may be synthesized using the methods described above for nucleic acid synthesis or cloning.

Where all or only a portion of the flanking sequence is known, it may be obtained using PCR and/or by screening a genomic library with suitable oligonucleotide and/or flanking sequence fragments from the same or another species.

Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® (Valencia, Calif.) column chromatography, or other methods known to the skilled artisan. Selection of suitable enzymes to accomplish this purpose will be readily apparent to one of ordinary skill in the art.

An origin of replication is typically a part of prokaryotic expression vectors purchased commercially, and aids in the amplification of the vector in a host cell. Amplification of the vector to a certain copy number can, in some cases, be important for optimal expression of the FGF-like polypeptide. If the vector of choice does not contain an origin of replication site, one may be chemically synthesized based on a known sequence, and ligated into the vector. The origin of replication from the plasmid pBR322 (Product No. 303-3s, New England Biolabs, Beverly, Mass.) is suitable for most Gram-negative bacteria and various origins (e.g., SV40, polyoma, adenovirus, vesicular stomatitus virus (VSV) or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding regions and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described above.

A selectable marker gene element encodes a protein necessary for the survival and growth of a host cell grown in a selective culture medium. Typical selection marker genes encode proteins that (a) confer resistance to antibiotics or other toxins, for example, ampicillin, tetracycline, or kanamycin for prokaryotic host cells, (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure that only the transformants are uniquely adapted to survive by virtue of the marker present in the vector. Selection pressure is imposed by culturing the transformed cells under conditions in which the concentration of selection agent in the medium is successively changed, thereby leading to amplification of both the selection gene and the DNA that encodes FGF-like polypeptide. As a result, increased quantities of FGF-like polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of the FGF-like polypeptide to be expressed. The Shine-Dalgarno sequence is varied but is typically a polypurine (i.e., having a high A-G content). Many Shine-Dalgarno sequences have been identified, each of which can be readily synthesized using methods set forth above and used in a prokaryotic vector.

A leader, or signal, sequence may be used to direct an FGF-like polypeptide out of the host cell. Typically, the signal sequence is positioned in the coding region of the FGF-like nucleic acid molecule, or directly at the 5' end of the FGF-like polypeptide coding region. Many signal sequences have been identified, and any of them that are functional in the selected host cell may be used in conjunction with the FGF-like gene or cDNA. Therefore, a signal sequence may be homologous (naturally occurring) or heterologous to the FGF-like gene or cDNA, Additionally, a signal sequence may be chemically synthesized using methods set forth above. In most cases, secretion of an FGF-like polypeptide from the host cell via the presence of a signal peptide will result in the removal of the signal peptide from the FGF-like polypeptide. The signal sequence may be a component of the vector, or it may be a part of FGF-like DNA that is inserted into the vector.

Included within the scope of this invention is the native FGF-like signal sequence joined to an FGF-like coding region and a heterologous signal sequence joined to an FGF-like coding region. The heterologous signal sequence selected should be one that is recognized and processed, i.e., cleaved by a signal peptidase, by the host cell. For prokaryotic host cells that do not recognize and process the native FGF-like signal sequence, the signal sequence is substituted by a prokaryotic signal sequence selected, for example, from the group of the alkaline phosphatase, penicillinase, or heat-stable enterotoxin II leaders. For yeast secretion, the native FGF-like signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add prosequences, which also may affect glycosylation. The final protein product may have, in the −1 position (relative to the first amino acid of the mature protein) one or more additional amino acids incident to expression, which may not have been totally removed. For example, the final protein product may have one or two amino acid found in the peptidase cleavage site, attached to the N-terminus. Alternatively, use of some enzyme cleavage sites may result in a slightly truncated form of the desired FGF-like polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the FGF-like gene especially where the gene used is a full-length genomic sequence or a fragment thereof. Where the intron is not naturally occurring within the gene (as for most cDNAs), the intron may be obtained from another source. The position of the intron with respect to flanking sequences and the FGF-like gene is generally important, as the intron must be transcribed to be effective. Thus, when an FGF-like cDNA molecule is being expressed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including any viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the FGF-like protein. Promoters are untranslated sequences located upstream (i.e., 5') to the start codon of a structural gene (generally within about 100 to 1000 bp) that control the transcription and translation of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. A large number of promoters, recognized by a variety of potential host cells, are well known. These promoters are operably linked to the DNA encoding FGF-like polypeptide by removing the promoter from the source DNA by restriction enzyme digestion and inserting the desired promoter sequence into the vector. The native FGF-like promoter sequence may be used to direct amplification and/or expression of FGF-like DNA. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase, a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any required restriction sites.

Suitable promoters for use with yeast hosts are also well known in the art. Yeast enhancers are advantageously used with yeast promoters. Suitable promoters for use with mammalian host cells are well known and include those obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling FGF-like gene expression include, but are not limited to: the SV40 early promoter region (Bernoist and Chambon, *Nature* 290:304-10 (1981)); the CMV promoter; the promoter contained in the 3' long terminal repeat of Rous sarcoma virus (Yamamoto, et al., *Cell* 22:787-97 (1980)); the herpes thymidine kinase promoter (Wagner et al., *Proc. Natl. Acad. Sci. U.S.A.* 78:1444-45 (1981)); the regulatory sequences of the metallothionine gene (Brinster et al., *Nature* 296:39-42 (1982)); prokaryotic expression vectors such as the beta-lactamase promoter (Villa-Kamaroff et al., *Proc. Natl. Acad. Sci. U.S.A.*, 75:3727-31 (1978)); or the tac promoter (DeBoer et al., *Proc. Natl. Acad. Sci. U.S.A.*, 80:21-25 (1983)). Also of interest are the following animal transcriptional control regions, which exhibit tissue specificity and have been utilized in transgenic animals: the elastase I gene control region which is active in pancreatic acinar cells (Swift et al., *Cell* 38:639-46 (1984); Ornitz et al., *Cold Spring Harbor Symp. Quant. Biol.* 50:399-409 (1986); MacDonald, *Hepatology* 7:425-515 (1987)); the insulin gene control region which is active in pancreatic beta cells (Hanahan, *Nature* 315:115-22 (1985)); the immunoglobulin gene control region which is active in lymphoid cells (Grosschedl et al., *Cell* 38:647-58 (1984); Adames et al., *Nature* 318:533-38 (1985); Alexander et al., *Mol. Cell. Biol.*, 7:1436-44 (1987)); the mouse mammary tumor virus control region which is active in testicular, breast, lymphoid and mast cells (Leder et al., *Cell* 45:485-95 (1986)); the albumin gene control region which is active in liver (Pinkert et al., *Genes and Devel.* 1:268-76 (1987)); the alpha-feto-protein gene control region which is active in liver (Krumlauf et al., *Mol. Cell. Biol.*, 5:1639-48 (1985); Hammer et al., *Science* 235:53-58 (1987)); the alpha 1-antitrypsin gene control region which is active in the liver (Kelsey et al., *Genes and Devel.* 1:161-71, 1987)); the beta-globin gene control region which is active in myeloid cells (Mogram et al., *Nature* 315:338-40 (1985); Kollias et al., *Cell* 46:89-94 (1986)); the myelin basic protein gene control region which is active in oligodendrocyte cells in the brain (Readhead et al., *Cell* 48:703-12 (1987)); the myosin light chain-2 gene control region which is active in skeletal muscle (Sani, *Nature* 314:283-86 (1985)); and the gonadotropic releasing hormone gene control region which is active in the hypothalamus (Mason et al., *Science* 234:1372-78 (1986)).

An enhancer sequence may be inserted into the vector to increase the transcription of a DNA encoding an FGF-like protein of the present invention by higher eukaryotes. Enhancers are cis-acting elements of DNA, usually about 10-300 bp in length, that act on the promoter to increase its transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to FGF-like DNA, it is typically located at a site 5' from the promoter.

Expression vectors of the invention may be constructed from starting vectors such as a commercially available vector. Such vectors may or may not contain all of the desired flanking sequences. Where one or more of the flanking sequences set forth above are not already present in the vector to be used, they may be individually obtained and ligated into the vector. Methods used for obtaining each of the flanking sequences are well known to one skilled in the art.

Preferred vectors for practicing this invention are those which are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET 15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (PCT Pub. No. WO 90/14363) and pFastBacDual (Gibco-BRL, Grand Island, N.Y.).

Additional possible vectors include, but are not limited to, cosmids, plasmids, or modified viruses, but the vector system must be compatible with the selected host cell. Such vectors include, but are not limited to plasmids such as Bluescript® plasmid derivatives (a high copy number ColE1-based phagemid, Stratagene Cloning Systems, La Jolla Calif.), PCR cloning plasmids designed for cloning Taq-amplified PCR products (e.g., TOPO™ TA Cloning® Kit, PCR2.1® plasmid derivatives, Invitrogen, Carlsbad, Calif.), and mammalian, yeast or virus vectors such as a baculovirus expression system (pBacPAK plasmid derivatives, Clontech, Palo Alto, Calif.). The recombinant molecules can be introduced into host cells via transformation, transfection, infection, electroporation, or other known techniques.

After the vector has been constructed and a nucleic acid molecule encoding an FGF-like polypeptide has been inserted into the proper site of the vector, the completed vector may be inserted into a suitable host cell for amplification and/or polypeptide expression.

Host cells may be prokaryotic host cells (such as *E. coli*) or eukaryotic host cells (such as a yeast cell, an insect cell, or a vertebrate cell). The host cell, when cultured under appropriate conditions, synthesizes an FGF-like polypeptide which can subsequently be collected from the culture medium (if the host cell secretes it into the medium) or directly from the host cell producing it (if it is not secreted). Selection of an appropriate host cell will depend upon various factors, such as desired expression levels, polypeptide modifications that are desirable or necessary for activity, such as glycosylation or phosphorylation, and ease of folding into a biologically active molecule.

A number of suitable host cells are known in the art and many are available from the American Type Culture Collection (ATCC), Manassas, Va. Examples include mammalian cells, such as Chinese hamster ovary cells (CHO), CHO DHFR-cells (Urlaub et al., *Proc. Natl. Acad. Sci. U.S.A.* 97:4216-20 (1980)), human embryonic kidney (HEK) 293 or 293T cells, or 3T3 cells. The selection of suitable mammalian host cells and methods for transformation, culture, amplification, screening, product production and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5, DH10, and MC1061) are well known as host cells in the field of biotechnology. Various strains of *B. subtilis, Pseudomonas* spp., other *Bacillus* spp., *Streptomyces* spp., and the like may also be employed in this method.

Many strains of yeast cells known to those skilled in the art are also available as host cells for expression of the polypeptides of the present invention. Preferred yeast cells include, for example, *Saccharomyces cerivisae.*

Additionally, where desired, insect cell systems may be utilized in the methods of the present invention. Such systems are described, for example, in Kitts et al., *Biotechniques,* 14:810-17 (1993); Lucklow, *Curr. Opin. Biotechnol.* 4:564-72 (1993); and Lucklow et al., *J. Virol.,* 67:4566-79 (1993). Preferred insect cells are Sf-9 and Hi5 (Invitrogen).

Transformation or transfection of an expression vector for an FGF-like polypeptide into a selected host cell may be accomplished by well known methods including methods such as calcium chloride, electroporation, microinjection, lipofection or the DEAE-dextran method. The method selected will in part be a function of the type of host cell to be used. These methods and other suitable methods are well known to the skilled artisan, and are set forth, for example, in Sambrook et al., supra.

One may also use transgenic animals to express glycosylated FGF-like polypeptides. For example, one may use a transgenic milk-producing animal (a cow or goat, for example) and obtain the present glycosylated polypeptide in the animal milk. One may also use plants to produce FGF-like polypeptides, however, in general, the glycosylation occurring in plants is different from that produced in mammalian cells, and may result in a glycosylated product which is not suitable for human therapeutic use.

Polypeptide Production

Host cells comprising an FGF-like polypeptide expression vector (i.e., transformed or transfected) may be cultured using standard media well known to the skilled artisan. The media will usually contain all nutrients necessary for the growth and survival of the cells. Suitable media for culturing *E. coli* cells are for example, Luria Broth (LB) and/or Terrific Broth (TB). Suitable media for culturing eukaryotic cells are RPMI 1640, MEM, DMEM, all of which may be supplemented with serum and/or growth factors as required by the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of an FGF-like polypeptide produced by a host cell can be evaluated using standard methods known in the art. Such methods include, without limitation, Western blot analysis, SDS-polyacrylamide gel electrophoresis, non-denaturing gel electrophoresis, HPLC separation, immunoprecipitation, and/or activity assays such as DNA binding gel shift assays.

If an FGF-like polypeptide has been designed to be secreted from the host cells, the majority of polypeptide may be found in the cell culture medium. If however, the FGF-like polypeptide is not secreted from the host cells, it will be present in the cytoplasm and/or the nucleus (for eukaryotic host cells) or in the cytosol (for gram-negative bacteria host cells).

For an FGF-like polypeptide situated in the host cell cytoplasm and/or nucleus, the host cells are typically first disrupted mechanically or with detergent to release the intracellular contents into a buffered solution. FGF-like polypeptide can then be isolated from this solution.

Purification of an FGF-like polypeptide from solution can be accomplished using a variety of techniques. If the polypeptide has been synthesized such that it contains a tag such as Hexahistidine (FGF-like polypeptide/hexaHis) or other small peptide such as FLAG (Eastman Kodak Co., New Haven, Conn.) or myc (Invitrogen) at either its carboxyl or amino terminus, it may essentially be purified in a one-step process by passing the solution through an affinity column where the column matrix has a high affinity for the tag or for the polypeptide directly (i.e., a monoclonal antibody specifically recognizing FGF-like polypeptide). For example, polyhistidine binds with great affinity and specificity to nickel and thus an affinity column of nickel (such as the Qiagen® nickel columns) can be used for purification of FGF-like polypeptide/polyHis. See, e.g., *Current Protocols in Molecular Biology* §10.11.8 (Ausubel et al., eds., John Wiley & Sons 1993).

Where an FGF-like polypeptide is prepared without a tag attached, and no antibodies are available, other well-known procedures for purification can be used. Such procedures include, without limitation, ion exchange chromatography, molecular sieve chromatography, HPLC, native gel electrophoresis in combination with gel elution, and preparative isoelectric focusing ("Isoprime" machine/technique, Hoefer Scientific). In some cases, two or more of these techniques may be combined to achieve increased purity.

If an FGF-like polypeptide is produced intracellularly, the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If an FGF-like polypeptide has formed inclusion bodies in the cytosol, the inclusion bodies can often bind to the inner and/or outer cellular membranes and thus will be found primarily in the pellet material after centrifugation. The pellet material can then be treated at pH extremes or with chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The FGF-like polypeptide in its now soluble form can then be analyzed using gel electrophoresis, immunoprecipitation, or the like. If it is desired to isolate the FGF-like polypeptide, isolation may be accomplished using standard methods such as those set forth below and in Marston et al., *Meth. Enz.,* 182:264-75 (1990).

In some cases, an FGF-like polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-mercaptoethanol(bME)/dithio-b(ME). In many instances, a cosolvent may be used or may be needed to increase the efficiency of the refolding and the more common reagents used for this purpose include glycerol, polyethylene glycol of various molecular weights, arginine and the like.

If inclusion bodies are not formed to a significant degree upon expression of an FGF-like polypeptide, the polypeptide will be found primarily in the supernatant after centrifugation of the cell homogenate and may be further isolated from the supernatant using methods such as those set forth below.

In situations where it is preferable to partially or completely purify an FGF-like polypeptide such that it is partially or substantially free of contaminants, standard methods known to the one skilled in the art may be used. Such methods include, without limitation, separation by electrophoresis followed by electroelution, various types of chromatography (affinity, immunoaffinity, molecular sieve, and/or ion exchange), and/or high pressure liquid chromatography. In some cases, it may be preferable to use more than one of these methods for complete purification.

FGF-like polypeptides, fragments, and/or derivatives thereof may also be prepared by chemical synthesis methods (such as solid phase peptide synthesis) using techniques known in the art such as those set forth by Merrifield et al., *J. Am. Chem. Soc.* 85:2149 (1963); Houghten et al., *Proc Natl Acad. Sci. USA* 82:5132 (1985); and Stewart and Young, *Solid Phase Peptide Synthesis* (Pierce Chemical Co. 1984). Such polypeptides may be synthesized with or without a methionine on the amino terminus. Chemically synthesized FGF-like polypeptides or fragments may be oxidized using methods set forth in these references to form disulfide bridges. FGF-like polypeptides, fragments or derivatives are expected to have comparable biological activity to the corresponding FGF-like polypeptides, fragments or derivatives produced recombinantly or purified from natural sources, and thus may be used interchangeably with recombinant or natural FGF-like polypeptide.

Another means of obtaining FGF-like polypeptide is via purification from biological samples such as source tissues and/or fluids in which the FGF-like polypeptide is naturally found. Such purification can be conducted using methods for protein purification as described above. The presence of the FGF-like polypeptide during purification may be monitored using, for example, an antibody prepared against recombinantly produced FGF-like polypeptide or peptide fragments thereof.

Polypeptides

Polypeptides of the invention include isolated FGF-like polypeptides and polypeptides related thereto including fragments, variants, fusion polypeptides, and derivatives as defined hereinabove.

FGF-like polypeptide fragments of the invention may result from truncations at the amino terminus (with or without a leader sequence), truncations at the carboxyl terminus, and/or deletions internal to the polypeptide. In preferred embodiments, truncations and/or deletions comprise about 10 amino acids, or about 20 amino acid, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such FGF-like polypeptide fragments may optionally comprise an amino terminal methionine residue.

FGF-like polypeptide variants of the invention include one or more amino acid substitutions, additions and/or deletions as compared to SEQ ID NO: 2 or SEQ ID NO: 4. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, as defined above, non-conservative, or any combination thereof, and wherein the FGF-like polypeptide variant retains an FGF-like activity. The variants may have additions of amino acid residues either at the carboxyl terminus or at the amino terminus (with or without a leader sequence). Preferred FGF-like polypeptide variants include glycosylation variants wherein the number and/or type of glycosylation sites has been altered compared to native FGF-like polypeptide. In one embodiment, FGF-like variants comprise a greater or a lesser number of N-linked glycosylation sites. An N-linked glycosylation site is characterized by the sequence: Asn-X-Ser or Thr, where the amino acid residue designated as "X" may be any type of amino acid except proline. Substitution(s) of amino acid residues to create this sequence provides a potential new site for addition of an N-linked carbohydrate chain. Alternatively, substitutions to eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred FGF-like variants include cysteine variants, wherein one or more cysteine residues are deleted or substituted with another amino acid (e.g., serine). Cysteine variants are useful when FGF-like polypeptide must be refolded into a biologically active conformation such as after isolation of insoluble inclusive bodies. Cysteine variants generally have fewer cysteine residues than the native protein, and typically have an even number to minimize interactions resulting from unpaired cysteines.

One skilled in the art will be able to determine suitable variants of the native FGF-like polypeptide using well-known techniques. For example, one may be able to predict suitable areas of the molecule that may be changed without destroying biological activity. Also, one skilled in the art will realize that even areas that may be important for biological activity or for structure may be subject to conservative amino acid substitutions without destroying the biological activity or without adversely affecting the polypeptide structure.

For predicting suitable areas of the molecule that may be changed without destroying activity, one skilled in the art may target areas not believed to be important for activity. For example, when similar polypeptides with similar activities from the same species or from other species are known, one skilled in the art may compare the amino acid sequence of FGF-like polypeptide to such similar polypeptides. After making such a comparison, one skilled in the art would be able to determine residues and portions of the molecules that are conserved among similar polypeptides. One skilled in the art would know that changes in areas of the FGF-like molecule that are not conserved would be less likely to adversely affect biological activity and/or structure. One skilled in the art would also know that, even in relatively conserved regions, one could have likely substituted chemically similar amino acids for the naturally occurring residues while retaining activity (conservative amino acid residue substitutions).

Also, one skilled in the art may review structure-function studies identifying residues in similar polypeptides that are important for activity or structure. In view of such a comparison, one skilled in the art can predict the importance of amino acid residues in FGF-like polypeptide that correspond to amino acid residues that are important for activity or structure in similar polypeptides. One skilled in the art may opt for chemically similar amino acid substitutions for such predicted important amino acid residues of FGF-like polypeptide.

If available, one skilled in the art can also analyze the three-dimensional structure and amino acid sequence in relation to that structure in similar polypeptides. In view of that information, one skilled in the art may be able to predict the alignment of amino acid residues of FGF-like polypeptide with respect to its three dimensional structure. One skilled in the art may choose not to make radical changes to amino acid residues predicted to be on the surface of the protein, since such residues may be involved in important interactions with other molecules.

Moreover, one skilled in the art could generate test variants containing a single amino acid substitution at each amino acid residue. The variants could be screened using activity assays disclosed in this application. Such variants could be used to gather information about suitable variants. For example, if one discovered that a change to a particular amino acid residue resulted in destroyed activity, variants with such a change would be avoided. In other words, based on information gathered from such experiments, when attempting to find additional acceptable variants, one skilled in the art would have known the amino acids where further substitutions should be avoided either alone or in combination with other mutations.

FGF-like fusion polypeptides of the invention comprise FGF-like polypeptides, fragments, variants, or derivatives fused to a heterologous peptide or protein. Heterologous peptides and proteins include, but are not limited to: an epitope to allow for detection and/or isolation of an FGF-like fusion polypeptide; a transmembrane receptor protein or a portion thereof, such as an extracellular domain, or a transmembrane and intracellular domain; a ligand or a portion thereof which binds to a transmembrane receptor protein; an enzyme or portion thereof which is catalytically active; a protein or peptide which promotes oligomerization, such as leucine zipper domain; and a protein or peptide which increases stability, such as an immunoglobulin constant region. An FGF-like polypeptide may be fused to itself or to a fragment, variant, or derivative thereof. Fusions may be made either at the amino terminus or at the carboxyl terminus of an FGF-like polypeptide, and may be direct with no linker or adapter molecule or may be through a linker or adapter molecule, such as one or more amino acid residues up to about 20 amino acids residues, or up to about 50 amino acid residues. A linker or adapter molecule may also be designed with a cleavage site for a DNA restriction endonuclease or for a protease to allow for separation of the fused moieties.

In a further embodiment of the invention, an FGF-like polypeptide, fragment, variant and/or derivative is fused to an Fc region of human IgG. In one example, a human IgG hinge, CH2 and CH3 region may be fused at either the N-terminus or C-terminus of the FGF-like polypeptides using methods known to the skilled artisan. In another example, a portion of a hinge regions and CH2 and CH3 regions may be fused. The FGF-like Fc-fusion polypeptide so produced may be purified by use of a Protein A affinity column. In addition, peptides and proteins fused to an Fc region have been found to exhibit a substantially greater half-life in vivo than the unfused counterpart. Also, a fusion to an Fc region allows for dimerization/multimerization of the fusion polypeptide. The Fc region may be a naturally occurring Fc region, or may be altered to improve certain qualities, such as therapeutic qualities, circulation time, reduced aggregation, etc.

FGF-like polypeptide derivatives are included in the scope of the present invention. Such derivatives are chemically modified FGF-like polypeptide compositions in which FGF-like polypeptide is linked to a polymer. The polymer selected is typically water-soluble so that the protein to which it is attached does not precipitate in an aqueous environment, such as a physiological environment. The polymer may be of any molecular weight, and may be branched or unbranched. Included within the scope of FGF-like polypeptide polymers is a mixture of polymers. Preferably, for therapeutic use of the end-product preparation, the polymer will be pharmaceutically acceptable.

The water soluble polymer or mixture thereof may be selected from the group consisting of, for example, polyethylene glycol (PEG), monomethoxy-polyethylene glycol, dextran (such as low molecular weight dextran, of, for example about 6 kD), cellulose, or other carbohydrate based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the invention are bifunctional PEG cross-linking molecules that may be used to prepare covalently attached FGF-like polypeptide multimers For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono C1-C10 alkoxy or aryloxy derivatives thereof (see U.S. Pat. No. 5,252,714).

Pegylation of FGF-like polypeptides may be carried out by any of the pegylation reactions known in the art, as described for example in the following references: Francis et al., Focus on Growth Factors 3, 4-10 (1992); EP 0 154 316; EP 0 401 384 and U.S. Pat. No. 4,179,337. Pegylation may be carried out via an acylation reaction or an alkylation reaction with a reactive polyethylene glycol molecule (or an analogous reactive water-soluble polymer) as described below.

One water-soluble polymer for use herein is polyethylene glycol, abbreviated PEG. As used herein, polyethylene glycol is meant to encompass any of the forms of PEG that have been used to derivatize other proteins, such as mono-(C1-C10) alkoxy- or aryloxy-polyethylene glycol.

In general, chemical derivatization may be performed under any suitable conditions used to react a biologically active substance with an activated polymer molecule. Methods for preparing pegylated FGF-like polypeptides will generally comprise the steps of (a) reacting the polypeptide with polyethylene glycol (such as a reactive ester or aldehyde derivative of PEG) under conditions whereby FGF-like polypeptide becomes attached to one or more PEG groups, and (b) obtaining the reaction product(s). In general, the optimal reaction conditions for the acylation reactions will be determined based on known parameters and the desired result. For example, the larger the ratio of PEG: protein, the greater the percentage of poly-pegylated product.

In a preferred embodiment, the FGF-like polypeptide derivative will have a single PEG moiety at the amino terminus. See U.S. Pat. No. 5,234,784, herein incorporated by reference.

Generally, conditions that may be alleviated or modulated by administration of the present FGF-like polypeptide derivative include those described herein for FGF-like polypeptides. However, the FGF-like polypeptide derivative disclosed herein may have additional activities, enhanced or reduced biological activity, or other characteristics, such as increased or decreased half-life, as compared to the non-derivatized molecules.

Antibodies

FGF-like polypeptides, fragments, variants, and derivatives may be used to prepare antibodies using methods known in the art. Thus, antibodies and antibody fragments that bind FGF-like polypeptides are within the scope of the present invention. Antibodies may be polyclonal, monospecific polyclonal, monoclonal, recombinant, chimeric, humanized, fully human, single chain and/or bispecific.

Polyclonal antibodies directed toward an FGF-like polypeptide generally are raised in animals (e.g., rabbits or mice) by multiple subcutaneous or intraperitoneal injections of FGF-like polypeptide and an adjuvant. It may be useful to conjugate an FGF-like polypeptide, or a variant, fragment or derivative thereof to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-FGF-like antibody titer.

Monoclonal antibodies directed toward FGF-like polypeptide are produced using any method that provides for the production of antibody molecules by continuous cell lines in culture. Examples of suitable methods for preparing monoclonal antibodies include hybridoma methods of Kohler, et al., *Nature* 256:495-97 (1975), and the human B-cell hybridoma method, Kozbor, *J. Immunol.* 133:3001 (1984); Brodeur et al., *Monoclonal Antibody Production Techniques and Applications* 51-63 (Marcel Dekker 1987).

Also provided by the invention are hybridoma cell lines that produce monoclonal antibodies reactive with FGF-like polypeptides.

Monoclonal antibodies of the invention may be modified for use as therapeutics. One embodiment is a "chimeric" antibody in which a portion of the heavy and/or light chain is identical with or homologous to corresponding sequence in antibodies derived from a particular species or belonging to a particular antibody class or subclass, while the remainder of the chain(s) is identical with or homologous to corresponding sequence in antibodies derived from another species or belonging to another antibody class or subclass, as well as fragments of such antibodies, so long as they exhibit the desired biological activity (see U.S. Pat. No. 4,816,567; Morrison, et al., *Proc. Natl. Acad. Sci. U.S.A.* 81: 6851-55 (1985).

In another embodiment, a monoclonal antibody of the invention is a "humanized" antibody. Methods for humanizing non-human antibodies are well known in the art. Generally, a humanized antibody has one or more amino acid residues introduced into it from a source that is non-human. Humanization can be performed following methods known in the art (Jones, et al., *Nature* 321: 522-25 (1986); Riechmann, et al., *Nature* 332:323-27 (1988); Verhoeyen et al., *Science* 239:1534-36 (1988)), by substituting rodent complementarily-determining regions (CDRs) for the corresponding regions of a human antibody.

Also encompassed by the invention are fully human antibodies that bind FGF-like polypeptides, fragments, variants, and/or derivatives. Such antibodies are produced by immunization with an FGF-like antigen (optionally conjugated to a carrier) of transgenic animals (e.g., mice) that are capable of producing a repertoire of human antibodies in the absence of endogenous immunoglobulin production. See, e.g., Jakobovits, et al., *Proc. Natl. Acad. Sci. U.S.A.* 90: 2551-55 (1993); Jakobovits, et al., *Nature* 362:255-58 (1993); Bruggermann et al., *Year in Immuno.* 7:33 (1993). Human antibodies can also be produced in phage-display libraries (Hoogenboom et al., *J. Mol. Biol.* 227:381 (1991); Marks, et al., *J. Mol. Biol.* 222:581 (1991)).

Chimeric, CDR grafted and humanized antibodies are typically produced by recombinant methods. Nucleic acids encoding the antibodies are introduced into host cells and expressed using materials and procedures described herein above. In a preferred embodiment, the antibodies are produced in mammalian host cells, such as CHO cells. Fully human antibodies may be produced by expression of recombinant DNA transfected into host cells or by expression in hybridoma cells as described above.

For diagnostic applications, in certain embodiments, anti-FGF-like antibodies typically will be labeled with a detectable moiety. The detectable moiety can be any one that is capable of producing, either directly or indirectly, a detectable signal. For example, the detectable moiety may be a radioisotope, such as $^3H$, $^{14}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, β-galactosidase or horseradish peroxidase. Bayer, et al., *Meth. Enz.* 184: 138-63 (1990).

The anti-FGF-like antibodies of the invention may be employed in any known assay method, such as competitive binding assays, direct and indirect sandwich assays, and immunoprecipitation assays (Sola, *Monoclonal Antibodies: A Manual of Techniques* 147-58 (CRC Press 1987)) for detection and quantitation of FGF-like polypeptides. The antibodies will bind FGF-like polypeptides with an affinity that is appropriate for the assay method being employed.

Competitive binding assays rely on the ability of a labeled standard (e.g., an FGF-like polypeptide, or an immunologically reactive portion thereof) to compete with the test sample analyte (an FGF-like polypeptide) for binding with a limited amount of anti FGF-like antibody. The amount of an FGF-like polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an ELISA assay, in which case the detectable moiety is an enzyme.

The anti-FGF-like antibodies of the invention also are useful for in vivo imaging, wherein an antibody labeled with a detectable moiety is administered to an animal, preferably into the bloodstream, and the presence and location of the labeled antibody in the host is assayed. The antibody may be labeled with any moiety that is detectable in an animal, whether by nuclear magnetic resonance, radiology, or other detection means known in the art.

The invention also relates to a kit comprising anti-FGF-like antibodies and other reagents useful for detecting FGF-like polypeptide levels in biological samples. Such reagents may include a secondary activity, a detectable label, blocking serum, positive and negative control samples and detection reagents.

Antibodies of the invention may be used as therapeutics. Therapeutic antibodies are generally agonists or antagonists, in that they either enhance or reduce, respectively, at least one of the biological activities of an FGF-like polypeptide. In one embodiment, antagonist antibodies of the invention are antibodies or binding fragments thereof which are capable of specifically binding to an FGF-like polypeptide, fragment, variant, and/or derivative, and which are capable of inhibiting or eliminating the functional activity of an FGF-like polypeptide in vivo or in vitro. In preferred embodiments, an antagonist antibody will inhibit the functional activity of an FGF-like polypeptide at least about 50%, and preferably at least about 80%. In another embodiment antagonist antibodies are capable of interacting with an FGF-like binding partner thereby inhibiting or eliminating FGF-like activity in vitro or in vivo. Agonist and antagonist anti-FGF-like antibodies are identified by screening assays described below.

Genetically Engineered Non-Human Animals

Additionally included within the scope of the present invention are non-human animals such as mice, rats, or other rodents, rabbits, goats, sheep, or other farm animals, in which the genes encoding native FGF-like polypeptide have been disrupted (i.e., "knocked out") such that the level of expression of FGF-like polypeptide is significantly decreased or completely abolished. Such animals may be prepared using techniques and methods such as those described in U.S. Pat. No. 5,557,032.

The present invention further includes non-human animals such as mice, rats, or other rodents, rabbits, goats, sheep, or other farm animals, in which a gene encoding a native form of FGF-like polypeptide for that animal or a heterologous FGF-like polypeptide gene is overexpressed by the animal, thereby creating a "transgenic" animal. Such transgenic animals may be prepared using well known methods such as those described in U.S. Pat. No. 5,489,743 and PCT Pub. No. WO 94/28122.

The present invention further includes non-human animals in which the promoter for one or more of the FGF-like polypeptides of the present invention is either activated or inactivated (e.g., by using homologous recombination methods as described below) to alter the level of expression of one or more of the native FGF-like polypeptides.

Such non-human animals may be used for drug candidate screening. The impact of a drug candidate on the animal may be measured. For example, drug candidates may decrease or increase expression of the FGF-like polypeptide gene. In certain embodiments, the amount of FGF-like polypeptide or an FGF-like polypeptide fragment that is produced may be measured after exposure of the animal to the drug candidate. In certain embodiments, one may detect the actual impact of the drug candidate on the animal. For example, overexpression of a particular gene may result in, or be associated with, a disease or pathological condition. In such cases, one may test a drug candidate's ability to decrease expression of the gene or its ability to prevent or inhibit a pathological condition. In other examples, production of a particular metabolic product such as a fragment of a polypeptide, may result in, or be associated with, a disease or pathological condition. In such cases, one may test a drug candidate's ability to decrease production of such a metabolic product or its ability to prevent or inhibit a pathological condition.

Modulators of FGF-like Polypeptide Activity

In some situations, it may be desirable to identify molecules that are modulators, i.e., agonists or antagonists, of the activity of FGF-like polypeptide.

Natural or synthetic molecules that modulate FGF-like polypeptide can be identified using one or more screening assays, such as those described below. Such molecules may be administered either in an ex vivo manner or in an in vivo manner by local or intravenous injection or by oral delivery, implantation device, or the like.

The following definition is used herein for describing the assays:

"Test molecule" refers to a molecule that is under evaluation for the ability to modulate (i.e., increase or decrease) the activity of an FGF-like polypeptide. Most commonly, a test molecule will interact directly with an FGF-like polypeptide. However, it is also contemplated that a test molecule may also modulate FGF-like polypeptide activity indirectly, such as by affecting FGF-like gene expression, or by binding to an FGF-like binding partner (e.g., receptor or ligand). In one embodiment, a test molecule will bind to an FGF-like polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with FGF-like polypeptides are encompassed by the invention. In certain embodiments, an FGF-like polypeptide is incubated with a test molecule under conditions that permit interaction of the test molecule with an FGF-like polypeptide, and the extent of the interaction can be measured. The test molecule may be screened in a substantially purified form or in a crude mixture. Test molecules may be nucleic acid molecules, proteins, peptides, carbohydrates, lipids, or small molecular weight organic or inorganic compounds. Once a set of test molecules has been identified as interacting with an FGF-like polypeptide, the molecules may be further evaluated for their ability to increase or decrease FGF-like polypeptide activity.

Measurement of the interaction of test molecules with FGF-like polypeptides may be carried out in several formats, including cell-based binding assays, membrane binding assays, solution-phase assays and immunoassays. In general, test molecules are incubated with an FGF-like polypeptide for a specified period of time and FGF-like polypeptide activity is determined by one or more assays described herein for measuring biological activity.

Interaction of test molecules with FGF-like polypeptides may also be assayed directly using polyclonal or monoclonal antibodies in an immunoassay. Alternatively, modified forms of FGF-like polypeptides containing epitope tags as described above may be used in solution and immunoassays.

In certain embodiments, an FGF-like polypeptide agonist or antagonist may be a protein, peptide, carbohydrate, lipid, or small molecular weight molecule that interacts with FGF-like polypeptide to regulate its activity. Potential protein antagonists of FGF-like polypeptide include antibodies that interest with active regions of the polypeptide and inhibit or eliminate at least one activity of FGF-like polypeptide. Molecules which regulate FGF-like polypeptide expression may include nucleic acids which are complementary to nucleic acids encoding an FGF-like polypeptide, or are complementary to nucleic acids sequences which direct or control expression of FGF-like polypeptide, and which act as anti-sense regulators of expression.

In the event that FGF-like polypeptides display biological activity through interaction with a binding partner (e.g., a receptor or a ligand), a variety of in vitro assays may be used to measure binding of an FGF-like polypeptide to a corresponding binding partner. These assays may be used to screen test molecules for their ability to increase or decrease the rate and/or the extent of binding of an FGF-like polypeptide to its binding partner. In one assay, an FGF-like polypeptide is immobilized by attachment to the bottom of the wells of a microtiter plate. Radiolabeled FGF-like binding partner (for example, iodinated FGF-like binding partner) and the test molecules can then be added either one at a time (in either order) or simultaneously to the wells. After incubation, the wells can be washed and counted using a scintillation counter for radioactivity to determine the extent of binding to FGF-like protein by its binding partner. Typically, the molecules will be tested over a range of concentrations and a series of control wells lacking one or more elements of the test assays can be used for accuracy in evaluation of the results. An alternative to this method involves reversing the "positions" of the proteins, i.e., immobilizing FGF-like binding partner to the microtiter plate wells, incubating with the test molecule and radiolabeled FGF-like polypeptide, and determining the extent of FGF-like binding (see, e.g., *Current Protocols in Molecular Biology*, chap. 18 (Ausubel et al., eds., John Wiley & Sons 1995)).

As an alternative to radiolabeling, an FGF-like polypeptide or its binding partner may be conjugated to biotin and the presence of biotinylated protein can then be detected using streptavidin linked to an enzyme, such as horse radish peroxidase (HRP) or alkaline phosphatase (AP), that can be detected colorometrically, or by fluorescent tagging of streptavidin. An antibody directed to an FGF-like polypeptide or to an FGF-like binding partner and that is conjugated to biotin may also be used and can be detected after incubation with enzyme-linked streptavidin linked to AP or HRP An FGF-like polypeptide and an FGF-like binding partner may also be immobilized by attachment to agarose beads, acrylic beads, or other types of such inert substrates. The substrate-protein complex can be placed in a solution containing the complementary protein and the test compound; after incubation, the beads can be precipitated by centrifugation, and the amount of binding between an FGF-like polypeptide and its binding partner can be assessed using the methods described above. Alternatively, the substrate-protein complex can be immobilized in a column and the test molecule and complementary protein passed over the column. Formation of a complex between an FGF-like polypeptide and its binding partner can then be assessed using any of the techniques set forth above, i.e., radiolabeling, antibody binding, or the like.

Another in vitro assay that is useful for identifying a test molecule which increases or decreases formation of a complex between an FGF-like binding protein and an FGF-like binding partner is a surface plasmon resonance detector system such as the Biacore assay system (Pharmacia, Piscataway, N.J.). The Biacore system may be carried out using the manufacturer's protocol. This assay essentially involves covalent binding of either FGF-like polypeptide or an FGF-like binding partner to a dextran-coated sensor chip that is located in a detector. The test compound and the other complementary protein can then be injected into the chamber containing the sensor chip either simultaneously or sequentially and the amount of complementary protein that binds can be assessed based on the change in molecular mass which is physically associated with the dextran-coated side of the sensor chip; the change in molecular mass can be measured by the detector system.

In some cases, it may be desirable to evaluate two or more test compounds together for their ability to increase or decrease formation of a complex between an FGF-like polypeptide and an FGF-like binding partner complex. In these cases, the assays set forth above can be readily modified by adding such additional test compounds either simultaneous with, or subsequent to, the first test compound. The remaining steps in the assay are as set forth above.

In vitro assays such as those described above may be used advantageously to screen rapidly large numbers of compounds for effects on complex formation by FGF-like polypeptide and FGF-like binding partner. The assays may be automated to screen compounds generated in phage display, synthetic peptide, and chemical synthesis libraries.

Compounds which increase or decrease formation of a complex between an FGF-like polypeptide and an FGF-like binding partner may also be screened in cell culture using cells and cell lines expressing either FGF-like polypeptide or FGF-like binding partner. Cells and cell lines may be obtained from any mammal, but preferably will be from human or other primate, canine, or rodent sources. The binding of an FGF-like polypeptide to cells expressing FGF-like binding partner at the surface is evaluated in the presence or absence of test molecules and the extent of binding may be determined by, for example, flow cytometry using a biotinylated antibody to an FGF-like binding partner. Cell culture assays may be used advantageously to further evaluate compounds that score positive in protein binding assays described above.

Cell cultures can also be used to screen the impact of a drug candidate. For example, drug candidates may decrease or increase expression of the FGF-like polypeptide gene. In certain embodiments, the amount of FGF-like polypeptide or an FGF-like polypeptide fragment that is produced may be measured after exposure of the cell culture to the drug candidate. In certain embodiments, one may detect the actual impact of the drug candidate on the cell culture. For example, overexpression of a particular gene may have a particular impact on the cell culture. In such cases, one may test a drug candidate's ability to increase or decrease expression of the gene or its ability to prevent or inhibit a particular impact on the cell culture. In other examples, production of a particular metabolic product such as a fragment of a polypeptide, may result in, or be associated with, a disease or pathological condition. In such cases, one may test a drug candidate's ability to decrease production of such a metabolic product in a cell culture.

Cell Source Identification Using FGF-Like Polypeptide

According to certain embodiments, it may be useful to be able to determine the source of a certain cell type. For example, it may be useful to determine the origin of a disease or pathological condition that may aid in selecting appropriate therapy. FGF-like polypeptide is specifically expressed in the liver (and weakly expressed in the lung). In certain embodiments, nucleic acid encoding an FGF-like polypeptide can be used as a probe to identify liver-derived cells by screening the nucleic acids of the cells with such a probe. In other embodiments, one may use the FGF-like polypeptide to make antibodies that are specific for FGF-like polypeptide. Such antibodies can be used to test for the presence of FGF-like polypeptide in cells, and thus, as a means for determining whether such cells were derived from the liver.

FGF-Like Polypeptide Compositions and Administration

Therapeutic compositions of FGF-like polypeptides are within the scope of the present invention. Such compositions may comprise a therapeutically effective amount of an FGF-like polypeptide, fragment, variant, or derivative in admixture with a pharmaceutically acceptable agent such as a pharmaceutically acceptable carrier. The carrier material may be water for injection, preferably supplemented with other materials common in solutions for administration to mammals. Typically, an FGF-like polypeptide therapeutic compound will be administered in the form of a composition comprising purified polypeptide, fragment, variant, or derivative in conjunction with one or more physiologically acceptable agents. Neutral buffered saline or saline mixed with serum albumin are exemplary appropriate carriers. Preferably, the product is formulated as a lyophilizate using appropriate excipients (e.g., sucrose). Other standard pharmaceutically acceptable agents such as carriers, diluents, and excipients may be included as desired. Other exemplary compositions comprise Tris buffer of about pH 7.0-8.5, or acetate buffer of about pH 4.0-5.5, which may further include sorbitol or a suitable substitute therefor.

FGF-like polypeptide pharmaceutical compositions typically include a therapeutically or prophylactically effective amount of FGF-like protein in admixture with one or more pharmaceutically and physiologically acceptable formulation agents selected for suitability with the mode of administration. Suitable formulation materials or pharmaceutically acceptable agents include, but are not limited to, antioxidants, preservatives, coloring, flavoring and diluting agents, emulsifying agents, suspending agents, solvents, fillers, bulking agents, buffers, delivery vehicles, diluents, excipients and/or pharmaceutical adjuvants. For example, a suitable vehicle may be water for injection, physiological saline solution, or artificial cerebrospinal fluid, possibly supplemented with other materials common in compositions for parenteral administration. Neutral buffered saline or saline mixed with serum albumin are further exemplary vehicles. The term "pharmaceutically acceptable carrier" or "physiologically acceptable carrier" as used herein refers to a formulation agent(s) suitable for accomplishing or enhancing the delivery of the FGF-like protein as a pharmaceutical composition.

The primary solvent in a composition may be either aqueous or non-aqueous in nature. In addition, the vehicle may contain other formulation materials for modifying or maintaining the pH, osmolarity, viscosity, clarity, color, sterility, stability, rate of dissolution, or odor of the formulation. Similarly, the composition may contain additional formulation materials for modifying or maintaining the rate of release of FGF-like protein, or for promoting the absorption or penetration of FGF-like protein.

The FGF-like polypeptide compositions can be administered parentally. Alternatively, the compositions may be administered intravenously or subcutaneously. When systemically administered, the therapeutic compositions for use in this invention may be in the form of a pyrogen-free, parentally acceptable aqueous solution. The preparation of such pharmaceutically acceptable protein solutions, with due regard to pH, isotonicity, stability and the like, is within the skill of the art.

Therapeutic formulations of FGF-like polypeptide compositions useful for practicing the present invention may be prepared for storage by mixing the selected composition having the desired degree of purity with optional physiologically acceptable carriers, excipients, or stabilizers (*Remington's Pharmaceutical Sciences* (18th Ed., A.R. Gennaro, ed., Mack Publishing Company 1990) in the form of a lyophilized cake or an aqueous solution.

Acceptable carriers, excipients or stabilizers preferably are nontoxic to recipients and are preferably inert at the dosages and concentrations employed, and preferably include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

The optimal pharmaceutical formulation will be determined by one skilled in the art depending upon the intended route of administration, delivery format and desired dosage. See, e.g., *Remington's Pharmaceutical Sciences,* 1435-1712 (18th Ed., A.R. Gennaro, ed., Mack Publishing Company 1990). Such compositions may influence the physical state, stability, rate of in vivo release, and rate of in vivo clearance of the present FGF-like protein.

An effective amount of an FGF-like polypeptide composition to be employed therapeutically will depend, for example, upon the therapeutic objectives such as the indication for which the FGF-like polypeptide is being used, the route of administration, and the condition of the patient. Accordingly, it may be necessary for the therapist to titer the dosage and modify the route of administration as required to obtain the optimal therapeutic effect. A typical dosage may range from about 0.1 µg/kg to up to about 100 mg/kg or more, depending on the factors mentioned above. In other embodiments, the dosage may range from 1 µg/kg up to about 100 mg/kg; or 5 µg/kg up to about 100 mg/kg; or 0.1 µg/kg up to about 100 mg/kg; or 1 µg/kg up to about 100 mg/kg. Typically, a clinician will administer the composition until a dosage is reached that achieves the desired effect. The composition may therefore be administered as a single dose or as two or more doses (which may or may not contain the same amount of FGF-like polypeptide) over time, or as a continuous infusion via implantation device or catheter.

As further studies are conducted, information will emerge regarding appropriate dosage levels for treatment of various conditions in various patients, and the ordinary skilled worker, considering the therapeutic context, the type of disorder under treatment, the age and general health of the recipient, will be able to ascertain proper dosing.

The FGF-like polypeptide composition to be used for in vivo parenteral administration typically must be sterile. This is readily accomplished by filtration through sterile filtration membranes. Where the composition is lyophilized, sterilization using these methods may be conducted either prior to, or following, lyophilization and reconstitution. The composition for parenteral administration ordinarily will be stored in lyophilized form or in solution.

Therapeutic compositions generally are placed into a container having a sterile access port, for example, an intravenous solution bag or vial having a stopper pierceable by a hypodermic injection needle.

Effective administration forms, such as (1) slow-release formulations, (2) inhalant mists, or (3) orally active formulations are also envisioned. The FGF-like polypeptide pharmaceutical composition also may be formulated for parenteral administration. Such parenterally administered therapeutic compositions are typically in the form of a pyrogen-free, parenterally acceptable aqueous solution comprising FGF-like polypeptide in a pharmaceutically acceptable vehicle. The FGF-like polypeptide pharmaceutical compositions also may include particulate preparations of polymeric compounds such as polylactic acid, polyglycolic acid, etc., or the introduction of FGF-like polypeptide into liposomes. Hyaluronic acid may also be used, and this may have the effect of promoting sustained duration in the circulation.

A particularly suitable vehicle for parenteral injection is sterile distilled water in which FGF-like polypeptide is formulated as a sterile, isotonic solution, properly preserved. Yet another preparation may involve the formulation of FGF-like polypeptide with an agent, such as injectable microspheres, bio-erodible particles or beads, or liposomes, that provides for the controlled or sustained release of the protein product which may then be delivered as a depot injection. Other suitable means for the introduction of FGF-like polypeptide include implantable drug delivery devices that contain the FGF-like polypeptide.

The preparations of the present invention may include other components, for example parenterally acceptable preservatives, tonicity agents, cosolvents, wetting agents, complexing agents, buffering agents, antimicrobials, antioxidants and surfactants, as are well known in the art. For example, suitable tonicity enhancing agents include alkali metal halides (preferably sodium or potassium chloride), mannitol, sorbitol and the like. Suitable preservatives include, but are not limited to, benzalkonium chloride, thimerosal, phenethyl alcohol, methylparaben, propylparaben, chlorhexidine, sorbic acid and the like. Hydrogen peroxide may also be used as preservative. Suitable cosolvents are for example glycerin, propylene glycol, and polyethylene glycol. Suitable complexing agents are for example caffeine, polyvinylpyrrolidone, beta-cyclodextrin, or hydroxypropyl-beta-cyclodextrin. Suitable surfactants or wetting agents include sorbitan esters, polysorbates such as polysorbate 80, tromethamine, lecithin, cholesterol, tyloxapal and the like. The buffers can be conventional buffers such as borate, citrate, phosphate, bicarbonate, or Tris-HCl.

The formulation components are present in concentrations that are acceptable to the site of administration. For example, buffers are used to maintain the composition at physiological pH or at slightly lower pH, typically within a pH range of from about 5 to about 8.

A pharmaceutical composition may be formulated for inhalation. For example, FGF-like polypeptide may be formulated as a dry powder for inhalation. FGF-like polypeptide inhalation solutions may also be formulated in a liquefied propellant for aerosol delivery. In yet another formulation, solutions may be nebulized.

It is also contemplated that certain formulations containing FGF-like polypeptide may be administered orally. FGF-like polypeptide that is administered in this fashion may be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents may be included to facilitate absorption of FGF-like polypeptide. Diluents, flavorings, low melting point waxes, vegetable oils, lubricants, suspending agents, tablet disintegrating agents, and binders may also be employed.

Another preparation may involve an effective quantity of FGF-like polypeptide in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional FGF-like polypeptide formulations will be evident to those skilled in the art, including formulations involving FGF-like polypeptide in combination with one or more other therapeutic agents. Techniques for formulating a variety of other sustained- or controlled-delivery means, such as liposome carriers, bio-erodible microparticles or porous beads and depot injections, are also known to those skilled in the art. See, for example, the Supersaxo et al. description of controlled release porous polymeric microparticles for the delivery of pharmaceutical compositions (See PCT Pub. No. WO 93/15722) the disclosure of which is hereby incorporated by reference.

Regardless of the manner of administration, the specific dose may be calculated according to body weight, body surface area, or organ size. Further refinement of the calculations necessary to determine the appropriate dosage for treatment involving each of the above mentioned formulations is routinely made by those of ordinary skill in the art and is within the ambit of tasks routinely performed by them. Appropriate dosages may be ascertained through use of appropriate dose-response data.

The route of administration of the composition is in accord with known methods, for example, oral, injection or infusion by intravenous, intraperitoneal, intracerebral (intraparenchymal), intracerebroventricular, intramuscular, intraocular, intraarterial, or intralesional routes, or by sustained release systems or implantation device which may optionally involve the use of a catheter. Where desired, the compositions may be administered continuously by infusion, bolus injection or by implantation device.

One may further administer the present pharmaceutical compositions by pulmonary administration, see, e.g., PCT Pub. WO 94/20069, which discloses pulmonary delivery of chemically modified proteins, herein incorporated by reference. For pulmonary delivery, the particle size should be suitable for delivery to the distal lung. For example, the particle size may be from 1 μm to 5 μm. However, larger particles may be used, for example, if each particle is fairly porous.

Alternatively or additionally, the composition may be administered locally via implantation into the affected area of a membrane, sponge, or other appropriate material on to which FGF-like polypeptide has been absorbed or encapsulated.

Where an implantation device is used, the device may be implanted into any suitable tissue or organ, and delivery of FGF-like polypeptide may be directly through the device via bolus, or via continuous administration, or via catheter using continuous infusion.

FGF-like polypeptide may be administered in a sustained release formulation or preparation. Suitable examples of sustained-release preparations include semipermeable polymer matrices in the form of shaped articles, for example, films, or microcapsules. Sustained release matrices include polyesters, hydrogels, polylactides (U.S. Pat. No. 3,773,919, EP Patent No. 58,481), copolymers of L-glutamic acid and gamma ethyl-L-glutamate (Sidman et al, *Biopolymers* 22: 547-56 (1983)), poly (2-hydroxyethyl-methacrylate) (Langer et al., *J. Biomed. Mater. Res.* 15: 167-277 (1981) and Langer, *Chem. Tech.* 12: 98-105 (1982)), ethylene vinyl acetate (Langer et al., supra) or poly-D(−)-3-hydroxybutyric acid (EP Patent No. 133,988). Sustained-release compositions also may include liposomes, which can be prepared by any of several methods known in the art (see, e.g., Epstein et al., *Proc. Natl. Acad. Sci. U.S.A.* 82:3688-92 (1985); EP Patent Nos. 36,676; 88,046; and 143,949).

The FGF-like polypeptides, fragments thereof, variants, and derivatives, may be employed alone, together, or in combination with other pharmaceutical compositions. The FGF-like polypeptides, fragments, variants, and derivatives may be used in combination with cytokines, growth factors, antibiotics, anti-inflammatories, and/or chemotherapeutic agents as is appropriate for the indication being treated.

In some cases, it may be desirable to use FGF-like polypeptide compositions in an ex vivo manner. Here, cells, tissues, or organs that have been removed from the patient are exposed to FGF-like polypeptide compositions after which the cells, tissues and/or organs are subsequently implanted back into the patient.

In other cases, an FGF-like polypeptide may be delivered through implanting into patients certain cells that have been genetically engineered, using methods such as those described herein, to express and secrete the polypeptides, fragments, variants, or derivatives. Such cells may be animal or human cells, and may be derived from the patient's own tissue or from another source, either human or non-human. Optionally, the cells may be immortalized. However, in order to decrease the chance of an immunological response, it is preferred that the cells be encapsulated to avoid infiltration of surrounding tissues. The encapsulation materials are typically biocompatible, semi-permeable polymeric enclosures or membranes that allow release of the protein product(s) but prevent destruction of the cells by the patient's immune system or by other detrimental factors from the surrounding tissues.

Methods used for membrane encapsulation of cells are familiar to the skilled artisan, and preparation of encapsulated cells and their implantation in patients may be accomplished without undue experimentation. See, e.g., U.S. Pat. Nos. 4,892,538; 5,011,472; and 5,106,627. A system for encapsulating living cells is described in PCT Pub. No. WO 91/10425 (Aebischer et al.). Techniques for formulating a variety of other sustained or controlled delivery means, such as liposome carriers, bio-erodible particles or beads, are also known to those in the art, and are described. The cells, with or without encapsulation, may be implanted into suitable body tissues or organs of the patient.

As discussed above, it may be desirable to treat isolated cell populations such as stem cells, leukocytes, red blood cells, bone marrow, chondrocytes, neurons, pancreatic islets, liver cells and the like with one or more FGF-like polypeptides, variants, derivatives and/or fragments. This can be accomplished by exposing the isolated cells to the polypeptide, variant, derivative, or fragment directly, where it is in a form that is permeable to or acts upon the cell membrane.

Additional objects of the present invention relate to methods for both the in vitro production of therapeutic proteins by means of homologous recombination and for the production and delivery of therapeutic proteins by gene therapy.

It is further envisioned that FGF-like protein may be produced by homologous recombination, or with recombinant production methods utilizing control elements introduced into cells already containing DNA encoding FGF-like polypeptide. For example, homologous recombination methods may be used to modify a cell that contains a normally transcriptionally silent FGF-like gene, or under expressed gene, and thereby produce a cell that expresses therapeutically efficacious amounts of FGF-like polypeptide. Homologous recombination is a technique originally developed for targeting genes to induce or correct mutations in transcriptionally active genes (Kucherlapati, *Prog. in Nucl. Acid Res. and Mol. Biol.* 36:301 (1989)). The basic technique was developed as a method for introducing specific mutations into specific regions of the mammalian genome (Thomas et al., *Cell* 44:419-28 (1986); Thomas and Capecchi, *Cell* 51:503-12, (1987); Doetschman et al., *Proc. Natl. Acad. Sci. U.S.A.* 85:8583-87 (1988)) or to correct specific mutations within defective genes (Doetschman et al., *Nature* 330:576-78 (1987)). Exemplary homologous recombination techniques are described in U.S. Pat. No. 5,272,071 (EP Patent No. 91 90 3051, EP Publication No. 505 500; PCT/US90/07642, PCT Pub. No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with the expression of a FGF-like protein. For example, a promoter/enhancer element, a suppresser, or an exogenous transcription modulatory element is inserted in the genome of the intended host cell in proximity and orientation sufficient to influence the transcription of DNA encoding the desired FGF-like protein. The control element controls a portion of the DNA present in the host cell genome. Thus, the expression of FGF-like protein may be achieved not by transfection of DNA that encodes the FGF-like gene itself, but rather by the use of targeting DNA (containing regions of homology with the endogenous gene of interest) coupled with DNA regulatory segments that provide the endogenous gene sequence with recognizable signals for transcription of a FGF-like protein.

In an exemplary method, expression of a desired targeted gene in a cell (i.e., a desired endogenous cellular gene) is altered by the introduction, by homologous recombination into the cellular genome at a preselected site, of DNA which includes at least a regulatory sequence, an exon and a splice donor site. These components are introduced into the chromosomal (genomic) DNA in such a manner that this, in effect, results in production of a new transcription unit (in which the regulatory sequence, the exon, and the splice donor site present in the DNA construct are operatively linked to the endogenous gene). As a result of introduction of these components into the chromosomal DNA, the expression of the desired endogenous gene is altered.

Altered gene expression, as used herein, encompasses activating (or causing to be expressed) a gene which is normally silent (unexpressed) in the cell as obtained, increasing expression of a gene which may include expressing a gene that is not expressed at physiologically significant levels in the cell as obtained, changing the pattern of regulation or induction such that it is different than occurs in the cell as obtained, and reducing (including eliminating) expression of a gene which is expressed in the cell as obtained.

The present invention further relates to DNA constructs useful in the method of altering expression of a target gene. In certain embodiments, the exemplary DNA constructs comprise: (a) a targeting sequence, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) a targeting sequence, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of FGF-like polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be backstitched into the newly synthesized daughter strand of DNA. The present invention, therefore, includes nucleotides encoding a FGF-like molecule, which nucleotides may be used as targeting sequences.

FGF-like polypeptide cell therapy—for example, implantation of cells producing FGF-like polypeptide—is also contemplated. This embodiment would involve implanting into the cells of a patient a construct capable of synthesizing and secreting a biologically active form of FGF-like polypeptide. Such FGF-like polypeptide-producing cells may be cells that are natural producers of FGF-like polypeptide or may be recombinant cells whose ability to produce FGF-like polypeptide has been augmented by transformation with a gene encoding the desired FGF-like molecule or with a gene augmenting the expression of FGF-like polypeptide. Such a modification may be accomplished by means of a vector suitable for delivering the gene as well as promoting its expression and secretion. In order to minimize a potential immunological reaction in a patient that is being administered an FGF-like protein or polypeptide of a foreign species, it is preferred that the natural cells producing FGF-like polypeptide be of human origin and produce human FGF-like polypeptide. Likewise, it is preferred that the recombinant cells producing FGF-like polypeptide are transformed with an expression vector containing a gene encoding a human FGF-like molecule.

Implanted cells may be encapsulated to avoid infiltration of surrounding tissue. Human or non-human animal cells may be implanted in patients in biocompatible, semipermeable polymeric enclosures or membranes that allow release of FGF-like polypeptide, but that prevent destruction of the cells by the patient's immune system or by other detrimental factors from the surrounding tissue. Alternatively, the patient's own cells, transformed to produce FGF-like polypeptide ex vivo, could be implanted directly into the patient without such encapsulation.

Techniques for the encapsulation of living cells are known in the art, and the preparation of the encapsulated cells and their implantation in a patient may be accomplished without undue experimentation. For example, Baetge et al. (PCT Pub. No. WO 95/05452, the disclosure of which is hereby incorporated by reference) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., *Exper. Neurol.* 113:322-29 (1991); Aebischer et al., *Exper. Neurol.*, 111:269-75 (1991); and Tresco et al., *ASAIO* 38:17-23 (1992).

In vivo and in vitro gene therapy delivery of FGF-like polypeptide is also envisioned. In vivo gene therapy may be accomplished by introducing the gene encoding FGF-like polypeptide into cells via local injection of a polynucleotide molecule or other appropriate delivery vectors (Hefti, *J. Neurobiology* 25:1418-35 (1994)). For example, a polynucleotide molecule encoding FGF-like protein may be contained in an adeno-associated virus vector for delivery to the targeted cells (see, e.g., Johnson, PCT Pub. No. WO 95/34670; PCT App. No. PCT/US95/07178). The recombinant adeno-associated virus (AAV) genome typically contains AAV inverted terminal repeats flanking a DNA sequence encoding FGF-like polypeptide operably linked to functional promoter and polyadenylation sequences.

Alternative viral vectors include, but are not limited to, retrovirus, adenovirus, herpes simplex virus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells which have been treated in vitro to insert a DNA segment encoding a therapeutic protein. Additional methods and materials for the practice of gene therapy techniques are described in U.S. Pat. No. 5,631,236 (involving adenoviral vectors); U.S. Pat. No. 5,672,510 (involving retroviral vectors); and U.S. Pat. No. 5,635,399 (involving retroviral vectors expressing cytokines).

Nonviral delivery methods include liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, transcription factors to enhance expression by a vector as well as methods of vector manufacture. Such additional methods and materials for the practice of gene therapy techniques are described in U.S. Pat. No. 4,970,154 (electroporation techniques); PCT Pub. No. WO 96/40958 (nuclear ligands); U.S. Pat. No. 5,679,559 (concerning a lipoprotein-containing system for gene delivery); U.S. Pat. No. 5,676,954 (involving liposome carriers); U.S. Pat. No. 5,593,875 (concerning methods for calcium phosphate transfection); and U.S. Pat. No. 4,945,050 (wherein biologically active particles are propelled at cells at a speed whereby the particles penetrate the surface of the cells and become incorporated into the interior of the cells). Expression control techniques include chemical induced regulation (see, e.g., PCT Pub. Nos. WO 96/41865 and WO 97/31899), the use of a progesterone antagonist in a modified steroid hormone receptor system (see, e.g., U.S. Pat. No. 5,364,791), ecdysone control systems (see, e.g., PCT Pub. No. WO 96/37609), and positive tetracycline-controllable transactivators (see, e.g., U.S. Pat. No. 5,589,362; U.S. Pat. No. 5,650,298; and U.S. Pat. No. 5,654,168).

It is also contemplated that FGF-like polypeptide gene therapy or cell therapy can further include the delivery of a second protein. For example, the host cell may be modified to express and release both FGF-like polypeptide and a second protein, for example insulin-like growth factor 1 (IGF-1). Alternatively, both FGF-like polypeptide and a second protein may be expressed in and released from separate cells. Such cells may be separately introduced into the patient or the cells may be contained in a single implantable device, such as the encapsulating membrane described above.

One manner in which gene therapy can be applied is to use the FGF-like gene (either genomic DNA, cDNA, and/or synthetic DNA encoding a FGF-like polypeptide, or a fragment, variant, or derivative thereof) which may be operably linked to a constitutive or inducible promoter to form a "gene therapy DNA construct." The promoter may be homologous or heterologous to the endogenous FGF-like gene, provided that it is active in the cell or tissue type into which the construct will be inserted. Other components of the gene therapy DNA construct may optionally include: DNA molecules designed for site-specific integration (e.g., endogenous flanking sequences useful for homologous recombination), a tissue-specific promoter, enhancers, silencers, DNA molecules capable of providing a selective advantage over the parent cell, DNA molecules useful as labels to identify transformed cells, negative selection systems, cell specific binding agents (as, for example, for cell targeting), cell-specific internalization factors, and transcription factors to enhance expression by a vector as well as factors to enable vector manufacture.

This gene therapy DNA construct can then be introduced into the patient's cells (either ex vivo or in vivo). One means for introducing the gene therapy DNA construct is via viral vectors. Suitable viral vectors typically used in gene therapy for delivery of gene therapy DNA constructs include, without limitation, adenovirus, adeno-associated virus, herpes simplex virus, lentivirus, papilloma virus, and retrovirus vectors. Some of these vectors, such as retroviral vectors, will deliver the gene therapy DNA construct to the chromosomal DNA of the patient's cells, and the gene therapy DNA construct can integrate into the chromosomal DNA; other vectors will function as episomes and the gene therapy DNA construct will remain in the cytoplasm.

Another means to increase endogenous FGF-like polypeptide expression in a cell via gene therapy is to insert one or more enhancer elements into the FGF-like polypeptide promoter, where the enhancer elements can serve to increase transcriptional activity of the FGF-like polypeptide gene. The enhancer elements used will be selected based on the tissue in which one desires to activate the gene enhancer elements known to confer promoter activation in that tissue will be selected. For example, if a gene encoding an FGF-like polypeptide is to be "turned on" in T-cells, the lck promoter enhancer element may be used. Here, the functional portion of the transcriptional element to be added may be inserted into a fragment of DNA containing the FGF-like polypeptide promoter (and optionally, inserted into a vector and/or 5' and/or 3' flanking sequences, etc.) using standard cloning techniques. This construct, known as a "homologous recombination construct," can then be introduced into the desired cells either ex vivo or in vivo.

Gene therapy can be used to decrease FGF-like polypeptide expression by modifying the nucleotide sequence of the endogenous promoter. Such modification is typically accomplished via homologous recombination methods. For example, a DNA molecule containing all or a portion of the promoter of the FGF-like gene selected for inactivation can be engineered to remove and/or replace pieces of the promoter that regulate transcription. Here, for example, the TATA box and/or the binding site of a transcriptional activator of the promoter may be deleted using standard molecular biology techniques; such deletion can inhibit promoter activity thereby repressing transcription of the corresponding FGF-like gene. Deletion of the TATA box or transcription activator binding site in the promoter may be accomplished by generating a DNA construct comprising all or the relevant portion of the FGF-like polypeptide promoter (from the same or a related species as the FGF-like gene to be regulated) in which one or more of the TATA box and/or transcriptional activator binding site nucleotides are mutated via substitution, deletion and/or insertion of one or more nucleotides such that the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described above. Typically, integration of the construct into the genomic DNA of the cells will be via homologous recombination, where the 5' and 3' DNA sequences in the promoter construct can serve to help integrate the modified promoter region via hybridization to the endogenous chromosomal DNA.

Other gene therapy methods may also be employed where it is desirable to inhibit the activity of one or more FGF-like polypeptides. For example, antisense DNA or RNA molecules, which have a sequence that is complementary to at least a portion of the selected FGF-like polypeptide gene can be introduced into the cell. Typically, each such antisense molecule will be complementary to the start site (5' end) of each selected FGF-like gene. When the antisense molecule then hybridizes to the corresponding FGF-like mRNA, translation of this mRNA is prevented.

Alternatively, gene therapy may be employed to create a dominant-negative inhibitor of one or more FGF-like polypeptides. In this situation, the DNA encoding a mutant full length or truncated polypeptide of each selected FGF-like polypeptide can be prepared and introduced into the cells of a patient using either viral or non-viral methods as described above. Each such mutant is typically designed to compete with endogenous polypeptide in its biological role.

Uses of FGF-Like Nucleic Acids and Polypeptides

Nucleic acid molecules of the invention may be used to map the locations of the FGF-like gene and related genes on chromosomes. Mapping may be done by techniques known in the art, such as PCR amplification and in situ hybridization.

The nucleic acid molecules are also used as anti-sense inhibitors of FGF-like polypeptide expression. Such inhibition may be effected by nucleic acid molecules that are complementary to and hybridize to expression control sequences (triple helix formation) or to FGF-like mRNA. Anti-sense probes may be designed by available techniques using the sequence of the FGF-like genes disclosed herein. Anti-sense inhibitors provide information relating to the decrease or absence of an FGF-like polypeptide in a cell or organism.

Hybridization probes may be prepared using an FGF-like gene sequence as provided herein to screen cDNA, genomic or synthetic DNA libraries for related sequences. Regions of the DNA and/or amino acid sequence of FGF-like polypeptide that exhibit significant identity to known sequences are readily determined using sequence alignment algorithms disclosed above and those regions may be used to design probes for screening.

The nucleic acid molecules of the invention may be used for gene therapy. Nucleic acid molecules that express FGF-like polypeptide in vivo provide information relating to the effects of the polypeptide in cells or organisms.

FGF-like nucleic acid molecules, fragments, variants, and/or derivatives that do not themselves encode biologically active polypeptides may be useful as hybridization probes in diagnostic assays to test, either qualitatively or quantitatively, for the presence of FGF-like DNA or corresponding RNA in mammalian tissue or bodily fluid samples.

FGF-like polypeptides, fragments, variants, and/or derivatives may be used to prevent or treat cirrhosis or other toxic insult of the liver; inflammatory bowel disease, mucositis, Crohn's disease, or other gastrointestinal abnormality; diabetes; neurodegenerative diseases; wounds; damage to the corneal epithelium, lens, or retinal tissue; damage to the renal tubules as a result of acute tubular necrosis; hematopoietic cell reconstitution following chemotherapy; multiple sclerosis; alopecia; diseases or abnormalities of androgen target organs; infantile respiratory distress syndrome, bronchopulmonary dysplasia, acute respiratory distress syndrome, or other lung abnormalities; or tumors of the eye or other tissues.

FGF-like polypeptide fragments, variants, and/or derivatives, whether biologically active or not, are useful for preparing antibodies that bind to an FGF-like polypeptide. The antibodies may be used for in vivo and in vitro diagnostic purposes, including, but not limited to, use in labeled form to detect the presence of FGF-like polypeptide in a body fluid or cell sample. The antibodies may also be used to prevent or treat conditions that may be associated with an increase in FGF-like polypeptide expression or activity. The antibodies may bind to an FGF-like polypeptide so as to diminish or block at least one activity characteristic of an FGF-like polypeptide, or may bind to a polypeptide to increase an activity.

A deposit of cDNA encoding FGF-like polypeptide in *E. coli* strain DH10B has been made with the American Type Culture Collection, 10801 University Boulevard, Manassas, Va. 20110-2209 on Sep. 3, 1999 and having accession No. PTA-626.

The following examples are intended for illustration purposes only, and should not be construed as limiting the scope of the invention in any way.

EXAMPLE 1

Cloning of the Murine FGF-like Polypeptide Gene

Generally, materials and methods as described in Sambrook et al. supra were used to clone and analyze the gene encoding rat FGF-like polypeptide.

Sequences encoding the murine FGF-like polypeptide were isolated from a mouse regenerating liver cDNA library by screening the library in a kFGF signal trap system (U.S. patent application Ser. No. 09/026,958). This primary screening technique enriched for clones encoding signal peptide-containing secreted proteins.

A primary library (Tmrl1) was constructed in the kFGF vector as follows. Regenerating mouse liver was removed 24 hours after partial hepatectomy, and poly A+ RNA prepared using a commercially available RNA extraction kit and mRNA purification kit (Pharmacia Biotech). A cDNA library was prepared using the SuperScript™ Plasmid System for cDNA Synthesis and Plasmid Cloning (Gibco BRL) with some modifications. First strand reactions were performed using 3 µg of poly A+ RNA and 500 µg of the primer 5'-GGAAGGAAAAAAG CGGCCGCAA-CANNNNNNNNN-3 (SEQ ID NO: 34). Following second strand synthesis, the cDNA was ligated to a Sal I adapter, digested with Not I, and then size fractionated by agarose gel electrophoresis. Fractionated cDNA, ranging from 0.2 to 0.8 kb in size, was purified using a Qiagen gel extraction kit and then ligated to the kFGF vector as follows. In a 20 µl reaction, 50 µg of vector DNA (previously digested with Sal I and Not I) was mixed with 20 µg of the purified cDNA, 1× ligase buffer, and 1 ml of T4 DNA ligase at 16° C. for 20 hours.

The product of this ligation was precipitated and introduced into *E. coli* by electroporation, after which transformed bacterial cells were grown in 5 ml SOC medium at 37° C. for 1 hour and then frozen at −80° C. in 10% glycerol. This constituted the primary Tmrl1 library. Plasmid DNA from the primary Tmrl1 cDNA library was prepared from pools of 50,000 colonies grown on LB/agar plates using standard procedures. Ten pools were prepared and plasmid DNA was isolated from the pools using Qiagen maxi prep kits.

The plasmid DNA that was recovered was subsequently introduced into NIH 3T3 cells by calcium phosphate transfection. In each reaction 100 ng of plasmid DNA from each pool was used to transfect approximately $2\times10^5$ cells in one 35 mm plate. After 24 hours, the cells were then split into five 100 mm plates, grown in normal medium for one day, and then grown in low serum medium for 13 days. Approximately 4000 total colonies were obtained following growth in the low serum media.

Signal peptide-enriched regenerating cDNA molecules were recovered from the transfected cells as follows. Cells were released from the plates by the addition of 2 ml trypsin-EDTA and incubation at 37° C. for 5 minutes, followed by gentle swirling. Released cells were transferred to 50 ml conical tubes with 2 ml of fetal calf serum and centrifuged at 1000 rpm for 5 minutes to pellet the cells. Cell pellets of no more than 1 gram were lysed with 20 ml of TRIZOL reagent (BRL), homogenized for 30 seconds, and then extracted with 4 ml of chloroform. The tubes were centrifuged at 4000 rpm for 30 minutes and the aqueous phase was transferred to a new tube. RNA was precipitated by adding 10 ml isopropanol, mixing, and then centrifuging for 30 minutes at 4200 rpm. The RNA pellet was washed with 10 ml of 70% ethanol, briefly dried, and then the pellet was resuspended in 0.5 ml TE buffer. Poly A+ RNA was prepared by using a commercially available mRNA purification kit (Pharmacia). After eluting poly A+ RNA from the column in 750 µl of TE buffer, the sample was then ethanol precipitated in two 1.5 ml microcentrifuge tubes by adding 40 µl of sample buffer and 1 ml of ethanol and incubating overnight at −70° C.

The cDNA inserts of positive clones were rescued by RT-PCR as follows. First strand synthesis was performed using the SuperScript™ preamplification system (BRL). A mixture containing 15 µg of poly A+ RNA from selected 3T3 colonies and 15 µl (2 µM) of vector primer (5'-AATCCGATGC-CCACGTTGCA GTA-3'; SEQ ID NO: 35) was prepared and then incubated at 70° C. for 10 minutes followed by equilibration at 50° C. A premixture containing 2.5 µl 10× buffer, 2.5 µl 25 mM $MgCl_2$, 1.3 µl 10 mM dNTPs, and 2.5 µl 0.1 M dithiothreitol was then added to the poly A+ RNA/primer mixture, after which 1.2 µl of reverse transcriptase was added and the reaction incubated at 50° C. for 1 hour. The reaction was stopped by heating at 70° C. for 15 minutes.

Following first strand synthesis, RNA was digested with 1 µl RNase H at 37° C. for 20 minutes. PCR was performed using Pfu polymerase (Perkin Elmer) as follows. In a total volume of 100 µl, 2 µl of the first strand reaction was added to 1×Pfu buffer, 0.5 µM each of the amplification primers (5'-AAAATCTTAG ACCGACGACTGTGTTT-3'; SEQ ID NO: 36; and 5'-GAGTCTCCGCAGCC TTTTGAGG-3'; SEQ ID NO: 37), 0.2 mM dNTPs, 5% DMS, and 2.5 units of Pfu polymerase. The amplification reaction was performed at 95° C. for 1 minute for 1 cycle; 95° C. for 30 seconds, 66° C. for 45 seconds, and 72° C. for 30 cycles; and 72° C. for 10 minutes for 1 cycle. PCR products were purified by phenol/chloroform extraction followed by ethanol precipitation, and then were digested with Not I and Sal I. Small digestion products and PCR primers were removed from the reaction using SizeSep 400 Spun columns.

Clones identified in the primary screen were subsequently analyzed in a secondary secretion assay. This secondary screening technique utilized a vector containing a truncated placental alkaline phosphatase (PLAP), in which the native signal peptide had been removed, as a secretion reporter gene. Heterologous cDNA fragments were tested for the presence of signal peptide secretion sequences by inserting individual sequences immediately upstream of the truncated PLAP gene and then transfecting COS7 cells with the test constructs. Inserted cDNA sequences encoding a signal peptide, when inserted in frame with the PLAP reporter sequence, lead to the formation of a fusion protein that can be secreted from the transfected cells.

The PLAP reporter construct was generated as follows. Human placenta RNA was subjected to RT/PCR amplification under standard conditions to generate a DNA fragment encoding a truncated human PLAP protein. The RNA was transcribed by reverse transcriptase using oligo d(T) as primer, and then PCR amplified with PLAP specific primers to produce a DNA product which encodes a PLAP sequence corresponding to amino acids 22 to 536 (Millan, *J. Biol. Chem.* 261(7):3112-15 (1986)). The PLAP amplification primers (5'-ACTGGCGGCCG CAGGCATCATCCCAGT-TGAGGAG-3'; SEQ ID NO: 38; and 5'-ACTGGT CACTC-GAGGGTACCTTAGCTAGCCCCCGGG-3'; SEQ ID NO: 39) were designed to contain Not I and Kpn I restriction sites, respectively, in order to facilitate the ligation of the PLAP fragment into the pcDNA3.1 vector (generating the vector pcDNA3.1/PLAP).

The Tmrl1 secondary library was constructed in pcDNA3.1/PLAP as follows. The cDNA inserts from clones in the primary Tmrl1 library were recovered from 3T3 cell colonies using the PCR amplification primers and conditions noted above. Recovered PCR products were then ligated into the pcDNA3.1/PLAP vector which had been digested with the Xho I and Not I restriction enzymes. Ligation products were then transformed into the *E. Coli* strain DH10B to generate the secondary Tmrl1 library.

To assay heterologous cDNA fragments for the presence of signal peptide secretion sequences individual colonies were first selected from a low density plating of the secondary Tmrl1 library on agar plates and placed into the wells of a standard 96-well plate containing bacterial growth medium. The cultures were then grown to saturation and plasmid DNA was prepared from each culture by standard procedures. Plasmid DNA prepared as such was used to transfect COS7 cells as described below.

COS7 cells were seeded in 96-well flat-bottom plates at a concentration of 6000 cells per well in 200 µl of a growth medium consisting of DMEM-HG, 10% fetal bovine serum and 1×PSG (penicillin, streptomycin and gentamycin). Following seeding with COS7 cells, the plates were incubated for 24 hours at 37° C. in a $CO_2$ incubator. The cells in each well were subsequently transfected with 500 ng of plasmid DNA recovered from selected secondary Tmrl1 library clones using Superfect reagent (Qiagen). Transfection reactions were allowed to proceed for two hours, after which the transfected cells were washed with 200 µl of phenol red-free, serum-free DMEM and then incubated with 100 µl of phenol red-free, serum-free DMEM and glutamate for 24 hours at 37° C. in a $CO_2$ incubator. Following incubation, 100 µl of a solution containing 200 µM 4-methylumbelli-feryl phosphate (Molecular Probes) in IM diethanolamine, 10 mM homo-arginine, 1 mM $MgCl_2$, and 1 mg/ml BSA was added to each well, and incubation continued for 1 hour at 37° C. The product of the alkaline phosphatase reaction was then read in a fluorometer at 360/460 nm.

A single clone (tmrl1-00001-e9), yielding an increased fluorescence readout in the PLAP assay and possessing a computer-predicted signal peptide sequence and homology to the FGF family, was identified in the secondary Tmrl1 library screen. This clone was subsequently used as a probe to isolate a full-length cDNA for murine FGF-like polypeptide from a mouse liver cDNA library. A mouse liver full-length cDNA library was constructed using standard techniques. Essentially, oligo d(T) was used to prime first strand synthesis from mRNA isolated from regenerating mouse liver and full-length cDNA sequences were then cloned into the pSPORT (Gibco BRL) vector using the Superscript Plasmid System for cDNA Synthesis and Plasmid Cloning (Gibco BRL).

In a primary screen of the mouse liver cDNA library, 50,000 colonies were plated on LB/Ampicillin plates and then transferred to nitrocellulose filters. The filters were screened with a mixture of probes derived from clones identified in the kFGF signal trap and secretion assay screenings. This pool of probes included a 339 bp Not I-Xba I fragment isolated from the tmrl1-00001-e9 clone. The filters were first prehybridized for 2 hours at 42° C. in a hybridization solution consisting of 50% formamide, 5×Denhardt's, 5×SSC, 0.5% SDS, and 100 µg/ml salmon sperm DNA. Following prehybridization, the filters were incubated with the $^{32}$P-dCTP labeled probes overnight at 42° C. in fresh hybridization solution. The filters were then washed with 0.1×SSC/0.1% SDS at 65° C. and were subsequently analyzed by autoradiography overnight at −80° C. From this initial screen, 92 positive clones were identified.

The positive clones isolated in the primary screen were pooled and rescreened with the 339 bp tmrl1-00001-e9 fragment alone. In this secondary screening, 6000 colonies derived from the clone pool were plated on LB/Ampicillin plates and then transferred to nitrocellulose filters. The hybridization conditions used in the secondary screen were the same as those used for the primary screen. Three individual clones (1E, 1E-4, and 1E-6) were identified in the secondary screen.

Restriction digestion of the three individual clones identified in the secondary screen indicated that each contained a 1.6 kb insert. Primers corresponding to the 5' (5'-TGGAATG-GATGAGATCTAGAG-3'; SEQ ID NO: 7) and 3' (5'-CTA-GATTCAGGAAGAGTCA-3'; SEQ ID NO: 8) ends of the coding sequence encoded by this insert were designed following partial sequence analysis of clone 1E. These primers were used in a polymerase chain reaction (PCR) amplification of clone 1E plasmid DNA. The amplification reaction was performed at 94° C. for 1 minute for 1 cycle; 94° C. for 15 seconds and 65° C. for 1.5 minutes for 35 cycles; and 72° C. for 10 minutes for 1 cycle. A PCR product of approximately 650 bp was obtained following amplification.

Following purification from a 1% agarose gel using a Qiagen gel extraction kit, the PCR product was sequenced. Sequence analysis of this amplification product indicated that the cDNA clones from which the PCR primers were derived contained a gene comprising a 630 bp open reading frame encoding a protein of 210 amino acids. FIG. 1 illustrates the nucleotide sequence of the murine FGF-like gene (SEQ ID NO: 3) and the deduced amino acid sequence of murine FGF-like protein (SEQ ID NO: 4). Subsequent sequence analysis of clone 1E also established that the open reading frame of the cDNA clones identified in the secondary screening was interrupted by two intron sequences. Computer analysis using the FASTA program of the Swissprot database indicated that this open reading frame encoded a polypeptide that is most closely related (39% identical) to FGF-6 (FIGS. 3A-3D).

Computer analysis, using the SIGNALP program (Center for Biological Sequence Analysis, The Technical University of Denmark), also indicated that the murine FGF-like polypeptide possessed a potential signal peptide at its amino terminus (MEWMRSRVGTLGLWVRLLLAV-FLLGVYQA; SEQ ID NO: 40; as underlined in FIG. 1). The initial translation product of murine FGF-like polypeptide has a calculated molecular weight of 23,237, not including possible post-translational modifications. After removal of the predicted 29 amino acid signal peptide sequence, the remaining predicted mature protein of 181 amino acids has a calculated molecular weight of 19,876. No predicted N-linked glycosylation sites were identified in the protein and the protein does not possess any dibasic protease processing sites.

EXAMPLE 2

Cloning of the Human FGF-Like Polypeptide Gene

Generally, materials and methods as described in Sambrook et al. supra were used to clone and analyze the gene encoding human FGF-like polypeptide.

Sequences encoding the human FGF-like polypeptide were isolated by screening a human cDNA library with a probe derived from the murine FGF-like polypeptide gene. A 460 bp probe was generated by PCR amplification of murine FGF-like polypeptide cDNA using the following primers: 5'-TGGAATG GATGAGATCTAGAG-3'; SEQ ID NO: 7) and 3' (5'-CATTGCGGCCGCTC AAGATGCAAAACG-CAGTG-3'; SEQ ID NO: 9) in reactions containing $^{32}$P-dCTP. The amplification reaction was performed at 94° C. for 1 minute for 1 cycle; 94° C. for 15 seconds and 65° C. for 1.5 minutes for 35 cycles; and 72° C. for 10 minutes for 1 cycle.

The 460 bp murine probe was used to isolate a full-length cDNA for human FGF-like polypeptide from a human liver cDNA library. A human liver full-length cDNA library was constructed using standard techniques. Essentially, oligo d(T) was used to prime first strand synthesis from mRNA obtained from Clontech (Palo Alto, Calif.) and full-length cDNA sequences were then cloned into the pSPORT (Gibco BRL) vector using the Superscript Plasmid System for cDNA Synthesis and Plasmid Cloning (Gibco BRL).

In a primary screen of the human liver cDNA library, 550,000 colonies were plated on LB/Ampicillin plates and then transferred to nitrocellulose filters. The filters were first prehybridized for 30 minutes at 60° C. in ExpressHyb solution (Clontech), and then were incubated with the $^{32}$P-dCTP labeled murine FGF-like probe overnight at 60° C. in fresh ExpressHyb solution. Following hybridization, the filters were washed twice for 30 minutes at room temperature in 2×SSC/0.1% SDS, twice for 30 minutes at 60° C. in 1×SSC/0.1% SDS, twice for 30 minutes at 65° C. in 0.1×SSC/0.1% SDS, and then the filters were analyzed by autoradiography overnight at –80° C. Positive clones identified in the primary screen were then rescreened, and four independent clones were recovered following the secondary screen. Plasmid DNA for these four clones was prepared and sequenced.

Sequence analysis indicated that the four clones contained inserts of either 1.2 kb or 1.8 kb. The 1.2 kb cDNA insert contained a gene comprising a 627 bp open reading frame encoding a protein of 209 amino acids. FIGS. 2A-2B illustrate the nucleotide sequence of the human FGF-like gene (SEQ ID NO: 1) and the deduced amino acid sequence of human FGF-like protein (SEQ ID NO: 2). While the 1.8 kb cDNA insert contained the same open reading frame as encoded by the 1.2 kb insert, the open reading frame of this insert was additionally interrupted by an intron corresponding in location to the second intron found in some of the murine cDNA clones isolated in Example 1.

FIGS. 3A-3D illustrate the amino acid sequence alignment of human FGF-like protein, murine FGF-like protein, and other members of the FGF family. The human FGF-like polypeptide is 76% identical to the murine FGF-like protein. Computer analysis, using the SIGNALP program (Center for Biological Sequence Analysis, The Technical University of Denmark), indicated that the human FGF-like polypeptide also possessed a potential signal peptide at its amino terminus (MDSDETGFEHSGLWVSVLAGLLLGACQA; SEQ ID NO: 41; as underlined in FIGS. 2A-2B). The initial translation product of human FGF-like polypeptide has a calculated molecular weight of 22,284, not including possible post-translational modifications. After removal of the predicted 28 amino acid signal peptide sequence, the remaining predicted mature protein of 181 amino acids has a calculated molecular weight of 19,395. No predicted N-linked glycosylation sites were identified in the protein and the protein does not possess any dibasic protease processing sites.

EXAMPLE 3

FGF-Like mRNA Expression

Expression of murine FGF-like mRNA was examined on a murine multiple tissue Northern blot (Clontech) using a $^{32}$P-dCTP labeled murine FGF-like probe. The probe consisted of a 391 bp fragment isolated from the tmrl1-00001-e9 clone by restriction digestion with Xba I and Not I. The blot was first prehybridized for 2 hours at 42° C. in a hybridization solution consisting of 50% formamide, 5×Denhardt's, 6×SSC, 0.5% SDS, and 100 µg/ml salmon sperm DNA. Following prehybridization, the filters were incubated with the $^{32}$P-dCTP labeled murine FGF-like probe overnight at 42° C. in fresh hybridization solution. The filters were then washed with 0.1×SSC/0.1% SDS at 65° C. and were subsequently analyzed by autoradiography overnight at −80° C. Two transcripts, of approximately 1.35 kb and 1.8 kb, were detected in murine liver (FIG. 4A). The 1.35 kb transcript showed the predominant expression.

Figure 4B:
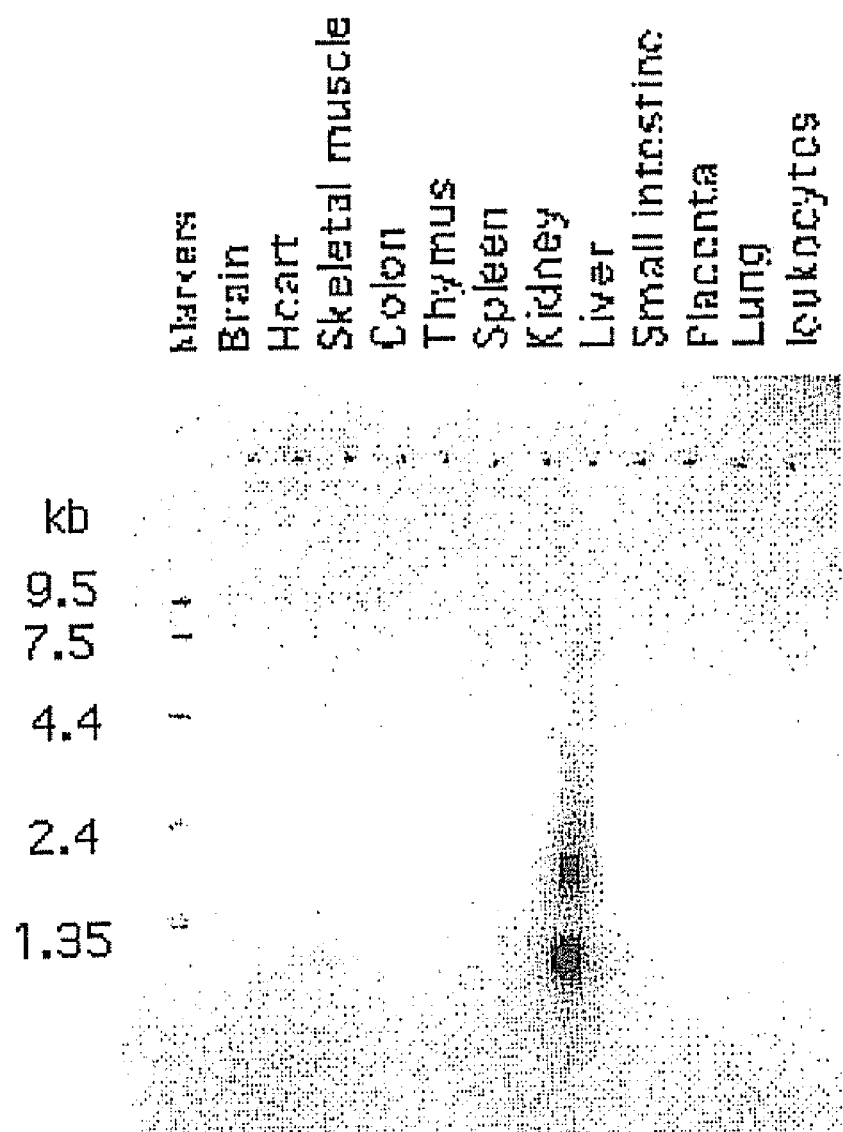

Expression of human FGF-like mRNA was examined on a Human RNA Master Blot™ (Clontech) and a human multiple tissue Northern blot (Clontech) using a $^{32}$P-dCTP labeled human FGF-like probe. The probe consisted of a 660 bp PCR product derived from the human FGF-like protein coding region using the primers: 5'-CTACTAAAGCTTCCAC-CATGGACTCGGACGAGACCG-3'; SEQ ID NO: 12; and 5'ATTCATGCGGCCGCGGAAGCGTAGCTGGGGCT TC-3'; SEQ ID NO: 13, and the human cDNA clone described above as a template. The amplification reaction was performed at 94° C. for 1 minute for 1 cycle; 94° C. for 15 seconds, 60° C. for 15 seconds, and 72° C. for 1 minute for 35 cycles; and 72° C. for 10 minutes for 1 cycle. The blots were first prehybridized for 1 hour at 65° C. in ExpressHyb solution (Clontech), and then were incubated with the $^{32}$P-dCTP labeled human FGF-like probe overnight at 65° C. in fresh ExpressHyb solution. Following hybridization, the filters were washed twice for 30 minutes at room temperature in 2×SSC/0.1% SDS, twice for 30 minutes at 65° C. in 0.1×SSC/ 0.1% SDS, and then the filters were analyzed by autoradiography overnight at −80° C. Two transcripts, of approximately 1.2 kb and 2 kb, were detected in human liver on the multiple tissue Northern blot 9 (FIG. 4B). Strong expression in adult liver and weak expression in lung and fetal liver was detected on the Human RNA Master Blot™ (FIG. 4C).

EXAMPLE 4

Production of FGF-Like Polypeptides in Mammalian Cells

Both the human and murine FGF-like polypeptides were expressed as fusion proteins with a human immunoglobulin IgG heavy chain Fc region at their carboxyl terminus. Template DNA sequences encoding human or murine FGF-like polypeptide were amplified by PCR using primers corresponding to the 5' and 3' ends of the sequence (Table II). The resulting PCR products corresponded to the coding region of either the human or murine FGF-like polypeptide, minus the translation termination codon. In addition, the primers were designed to incorporate a Hind III restriction endonuclease site at the 5' end of the PCR product and a Not I site at the 3' end of the product.

The human and murine FGF-like protein-Fc fusion constructs were generated by first cleaving the PCR products with Hind III and Not I and then ligating the fragments in frame to a DNA fragment encoding the HFc chain of human immunoglobulin IgG. The FGF-like protein-Fc insert was then ligated into the pCEP4 mammalian expression vector (Invitrogen). These ligations were transformed into the *E. coli* strain DH10 by electroporation and transformants selected for ampicillin resistance. Following sequence analysis of selected transformants, large-scale plasmid stocks were prepared for tissue culture transfection. Plasmid DNA for selected ampicillin resistant colonies was prepared and sequenced to confirm that the clone contained the desired insert.

To conduct functional studies on FGF-like protein, human or murine FGF-like/Fc fusion expression constructs were introduced into 293-EBNA (Invitrogen) cells using Super-Fect™ transfection reagent (Qiagen). The conditioned medium was harvested 48 hours after transient transfection. Western blot analysis, using an anti-human Fc antibody, confirmed that the conditioned media contained human or murine FGF-like protein-Fc fusion polypeptides.

Conditioned medium was purified by affinity chromatography as described below. The medium was first passed through a 0.2 µm filter. Protein A columns (Pharmacia) were equilibrated with ImmunoPure Gentle Binding Buffer (Pierce, Rockford, L), and then loaded with the filtered medium. The column was washed with ImmunoPure Gentle Binding Buffer until the absorbance at 280 nm reached a baseline. FGF-like/Fc protein was eluted from the column with ImmunoPure Gentle Binding Buffer. Fractions containing FGF-like/Fc protein were pooled, dialyzed in Tris-buffered saline (TBS) followed by Phosphate-buffered saline (PBS), and stored at 4° C. Gel electrophoretic analysis confirmed that the pooled fractions contained a purified protein of the expected molecular weight of about 60 kD.

While the present invention has been described in terms of the preferred embodiments, it is understood that variations and modifications will occur to those skilled in the art. Therefore, it is intended that the appended claims cover all such equivalent variations that come within the scope of the invention as claimed.

TABLE II

Primers Used in Recombinant Protein Expression

| | | |
|---|---|---|
| Murine 5' | 5'-CTACTAAAGCTTCCACCATGGAATGGATGAGATCTAG-3' | (SEQ ID NO: 10) |
| Murine 3' | 5'ATTCATGCGGCCGCGGACGCATAGCTGGGGCTT-3' | (SEQ ID NO: 11) |
| Human 5' | 5'-CTACTAAAGCTTCCACCATGGACTCGGACGAGACCG-3' | (SEQ ID NO: 12) |
| Human 3' | 5'-ATTCATGCGGCCGCGGAAGCGTAGCTGGGGCTTC-3' | (SEQ ID NO: 13) |

What is claimed is:

1. An isolated nucleic acid molecule comprising:
   (a) a nucleotide sequence that is at least 95% identical to the nucleotide sequence of either SEQ ID NO: 1 or the DNA insert in ATCC Deposit No. PTA-626;
   (b) a nucleotide sequence encoding a polypeptide that is at least 95% identical to the polypeptide of either SEQ ID NO: 2 or SEQ ID NO: 5;
   (c) a region of the nucleotide sequence of either SEQ ID NO: 1 or the DNA insert in ATCC Deposit No. PTA-626, encoding a polypeptide fragment of at least 150 amino acid residues;
   (d) a nucleotide sequence encoding an amino acid sequence of SEQ ID NO: 2 or SEQ ID NO: 5 having a C- and/or N-terminal truncation, wherein the polypeptide comprises at least 150 amino acid residues; or
   (e) a nucleotide sequence that is complementary to the nucleotide sequence of any of (a)-(d).

2. A vector comprising the nucleic acid molecule of claim 1.

3. An isolated host cell comprising the vector of claim 2.

4. The isolated host cell of claim 3 that is a eukaryotic cell.

5. The isolated host cell of claim 3 that is a prokaryotic cell.

6. A process of producing a polypeptide encoded by the vector of claim 2 comprising culturing an isolated host cell comprising said vector under suitable conditions to express the polypeptide, and optionally isolating the polypeptide.

7. An isolated host cell comprising the nucleic acid molecule of claim 1.

8. The isolated host cell of claim 7 that is a eukaryotic cell.

9. The isolated host cell of claim 7 that is a prokaryotic cell.

10. A process of producing a polypeptide encoded by the nucleic acid molecule of claim 1 comprising culturing an isolated host cell comprising the nucleic acid molecule of claim 1 under suitable conditions to express the polypeptide, and optionally isolating the polypeptide.

* * * * *

SEQUENCE LISTING

<160> NUMBER OF SEQ ID NOS: 41

<210> SEQ ID NO 1
<211> LENGTH: 1190
<212> TYPE: DNA
<213> ORGANISM: Homo sapiens
<220> FEATURE:
<221> NAME/KEY: CDS
<222> LOCATION: (142)..(771)

<400> SEQUENCE: 1

```
gaggatccag ccgaaagagg agccaggcac tcaggccacc tgagtctact cacctggaca        60
actggaatct ggcaccaatt ctaaaccact cagcttctcc gagctcacac cccggagatc       120
acctgaggac ccgagccatt g atg gac tcg gac gag acc ggg ttc gag cac        171
                        Met Asp Ser Asp Glu Thr Gly Phe Glu His
                         1               5                  10 tca gga ctg tgg gtt tct gtg ctg gct ggt ctt ctg ctg gga gcc tgc        219
Ser Gly Leu Trp Val Ser Val Leu Ala Gly Leu Leu Leu Gly Ala Cys
             15                  20                  25 cag gca cac ccc atc cct gac tcc agt cct ctc ctg caa ttc ggg ggc        267
Gln Ala His Pro Ile Pro Asp Ser Ser Pro Leu Leu Gln Phe Gly Gly
         30                  35                  40 caa gtc cgg cag cgg tac ctc tac aca gat gat gcc cag cag aca gaa        315
Gln Val Arg Gln Arg Tyr Leu Tyr Thr Asp Asp Ala Gln Gln Thr Glu
     45                  50                  55 gcc cac ctg gag atc agg gag gat ggg acg gtg ggg ggc gct gct gac        363
Ala His Leu Glu Ile Arg Glu Asp Gly Thr Val Gly Gly Ala Ala Asp
 60                  65                  70 cag agc ccc gaa agt ctc ctg cag ctg aaa gcc ttg aag ccg gga gtt        411
Gln Ser Pro Glu Ser Leu Leu Gln Leu Lys Ala Leu Lys Pro Gly Val
 75                  80                  85                  90 att caa atc ttg gga gtc aag aca tcc agg ttc ctg tgc cag cgg cca        459
Ile Gln Ile Leu Gly Val Lys Thr Ser Arg Phe Leu Cys Gln Arg Pro
                 95                 100                 105 gat ggg gcc ctg tat gga tcg ctc cac ttt gac cct gag gcc tgc agc        507
Asp Gly Ala Leu Tyr Gly Ser Leu His Phe Asp Pro Glu Ala Cys Ser
            110                 115                 120 ttc cgg gag ctg ctt ctt gag gac gga tac aat gtt tac cag tcc gaa        555
Phe Arg Glu Leu Leu Leu Glu Asp Gly Tyr Asn Val Tyr Gln Ser Glu
        125                 130                 135 gcc cac ggc ctc ccg ctg cac ctg cca ggg aac aag tcc cca cac cgg        603
Ala His Gly Leu Pro Leu His Leu Pro Gly Asn Lys Ser Pro His Arg
    140                 145                 150 gac cct gca ccc cga gga cca gct cgc ttc ctg cca cta cca ggc ctg        651
Asp Pro Ala Pro Arg Gly Pro Ala Arg Phe Leu Pro Leu Pro Gly Leu
155                 160                 165                 170 ccc ccc gca ccc cgg agc cca ccc gga atc ctg gcc ccc cag ccc ccc        699
Pro Pro Ala Pro Pro Glu Pro Pro Gly Ile Leu Ala Pro Gln Pro Pro
                175                 180                 185 gat gtg ggc tcc tcg gac cct ctg agc atg gtg gga cct tcc cag ggc        747
Asp Val Gly Ser Ser Asp Pro Leu Ser Met Val Gly Pro Ser Gln Gly
            190                 195                 200 cga agc ccc agc tac gct tcc tga agccagaggc tgtttactat gacatctcct        801
Arg Ser Pro Ser Tyr Ala Ser
        205                 210 ctttatttat taggttattt atcttattta ttttttttatt ttcttacctt gagataataa       861
agagttccag aggaggataa gaatgagcat gtgtgagtgt ctgagggaag acatggcagc       921
```

```
tgttttgtct cccttggccc ggacaatccc ctctacacct ccctcacgt ggtccgaggg    981 tcctggcttc ccactgggcc tcacttttt cttttcttt cttttctttt tttgagacg     1041 gagtctcgct ctgcactcca gcccaggcca cagagcgaga ttccatctca aaaaataaa   1101 taaataaata aataaataaa tataaaaata aaaaaaaaaa aaaaaaaaaa aaaaaaaaaa  1161
aaaaaaaaaa aaaaaaaaaa aaaaaaaaa                                   1190

<210> SEQ ID NO 2
<211> LENGTH: 209
<212> TYPE: PRT
<213> ORGANISM: Homo sapiens

<400> SEQUENCE: 2

Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala His Pro Ile Pro
                20                  25                  30

Asp Ser Ser Pro Leu Leu Gln Phe Gly Gly Gln Val Arg Gln Arg Tyr
            35                  40                  45

Leu Tyr Thr Asp Ala Gln Gln Thr Glu Ala His Leu Glu Ile Arg
        50                  55                  60

Glu Asp Gly Thr Val Gly Gly Ala Ala Asp Gln Ser Pro Glu Ser Leu
 65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
                100                 105                 110

Ser Leu His Phe Asp Pro Glu Ala Cys Ser Phe Arg Glu Leu Leu Leu
            115                 120                 125

Glu Asp Gly Tyr Asn Val Tyr Gln Ser Glu Ala His Gly Leu Pro Leu
        130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Pro Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

<210> SEQ ID NO 3
<211> LENGTH: 649
<212> TYPE: DNA
<213> ORGANISM: Mus musculus
<220> FEATURE:
<221> NAME/KEY: CDS
<222> LOCATION: (1)..(630)

<400> SEQUENCE: 3 atg gaa tgg atg aga tct aga gtt ggg acc ctg gga ctg tgg gtc cga    48
Met Glu Trp Met Arg Ser Arg Val Gly Thr Leu Gly Leu Trp Val Arg
 1               5                  10                  15 ctg ctg ctg gct gtc ttc ctg ctg ggg gtc tac caa gca tac ccc atc    96
Leu Leu Leu Ala Val Phe Leu Leu Gly Val Tyr Gln Ala Tyr Pro Ile
                20                  25                  30 cct gac tcc agc ccc ctc ctc cag ttt ggg ggt caa gtc cgg cag agg   144
Pro Asp Ser Ser Pro Leu Leu Gln Phe Gly Gly Gln Val Arg Gln Arg
```

-continued

```
Pro Asp Ser Ser Pro Leu Leu Gln Phe Gly Gly Gln Val Arg Gln Arg
        35                  40                  45 tac ctc tac aca gat gac gac caa gac act gaa gcc cac ctg gag atc    192
Tyr Leu Tyr Thr Asp Asp Asp Gln Asp Thr Glu Ala His Leu Glu Ile
    50                  55                  60 agg gag gat gga aca gtg gta ggc gca gca cac cgc agt cca gaa agt    240
Arg Glu Asp Gly Thr Val Val Gly Ala Ala His Arg Ser Pro Glu Ser
65                  70                  75                  80 ctc ctg gag ctc aaa gcc ttg aag cca ggg gtc att caa atc ctg ggt    288
Leu Leu Glu Leu Lys Ala Leu Lys Pro Gly Val Ile Gln Ile Leu Gly
                85                  90                  95 gtc aaa gcc tct agg ttt ctt tgc caa cag cca gat gga gct ctc tat    336
Val Lys Ala Ser Arg Phe Leu Cys Gln Gln Pro Asp Gly Ala Leu Tyr
            100                 105                 110 gga tcg cct cac ttt gat cct gag gcc tgc agc ttc aga gaa ctg ctg    384
Gly Ser Pro His Phe Asp Pro Glu Ala Cys Ser Phe Arg Glu Leu Leu
        115                 120                 125 ctg gag gac ggt tac aat gtg tac cag tct gaa gcc cat ggc ctg ccc    432
Leu Glu Asp Gly Tyr Asn Val Tyr Gln Ser Glu Ala His Gly Leu Pro
    130                 135                 140 ctg cgt ctg cct cag aag gac tcc cca aac cag gat gca aca tcc tgg    480
Leu Arg Leu Pro Gln Lys Asp Ser Pro Asn Gln Asp Ala Thr Ser Trp
145                 150                 155                 160 gga cct gtg cgc ttc ctg ccc atg cca ggc ctg ctc cac gag ccc caa    528
Gly Pro Val Arg Phe Leu Pro Met Pro Gly Leu Leu His Glu Pro Gln
                165                 170                 175 gac caa gca gga ttc ctg ccc cca gag ccc cca gat gtg ggc tcc tct    576
Asp Gln Ala Gly Phe Leu Pro Pro Glu Pro Pro Asp Val Gly Ser Ser
            180                 185                 190 gac ccc ctg agc atg gta gag cct tta cag ggc cga agc ccc agc tat    624
Asp Pro Leu Ser Met Val Glu Pro Leu Gln Gly Arg Ser Pro Ser Tyr
        195                 200                 205 gcg tcc tgactctttc ctgaatcta                                       649
Ala Ser
    210

<210> SEQ ID NO 4
<211> LENGTH: 210
<212> TYPE: PRT
<213> ORGANISM: Mus musculus

<400> SEQUENCE: 4

Met Glu Trp Met Arg Ser Arg Val Gly Thr Leu Gly Leu Trp Val Arg
1               5                   10                  15

Leu Leu Leu Ala Val Phe Leu Leu Gly Val Tyr Gln Ala Tyr Pro Ile
            20                  25                  30

Pro Asp Ser Ser Pro Leu Leu Gln Phe Gly Gly Gln Val Arg Gln Arg
        35                  40                  45

Tyr Leu Tyr Thr Asp Asp Asp Gln Asp Thr Glu Ala His Leu Glu Ile
    50                  55                  60

Arg Glu Asp Gly Thr Val Val Gly Ala Ala His Arg Ser Pro Glu Ser
65                  70                  75                  80

Leu Leu Glu Leu Lys Ala Leu Lys Pro Gly Val Ile Gln Ile Leu Gly
                85                  90                  95

Val Lys Ala Ser Arg Phe Leu Cys Gln Gln Pro Asp Gly Ala Leu Tyr
            100                 105                 110

Gly Ser Pro His Phe Asp Pro Glu Ala Cys Ser Phe Arg Glu Leu Leu
        115                 120                 125
```

```
Leu Glu Asp Gly Tyr Asn Val Tyr Gln Ser Glu Ala His Gly Leu Pro
        130                 135                 140

Leu Arg Leu Pro Gln Lys Asp Ser Pro Asn Gln Asp Ala Thr Ser Trp
145                 150                 155                 160

Gly Pro Val Arg Phe Leu Pro Met Pro Gly Leu Leu His Glu Pro Gln
                165                 170                 175

Asp Gln Ala Gly Phe Leu Pro Pro Glu Pro Pro Asp Val Gly Ser Ser
            180                 185                 190

Asp Pro Leu Ser Met Val Glu Pro Leu Gln Gly Arg Ser Pro Ser Tyr
        195                 200                 205

Ala Ser
    210

<210> SEQ ID NO 5
<211> LENGTH: 181
<212> TYPE: PRT
<213> ORGANISM: Homo sapiens

<400> SEQUENCE: 5

His Pro Ile Pro Asp Ser Ser Pro Leu Leu Gln Phe Gly Gly Gln Val
  1               5                  10                  15

Arg Gln Arg Tyr Leu Tyr Thr Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Pro Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 6
<211> LENGTH: 181
<212> TYPE: PRT
<213> ORGANISM: Mus musculus

<400> SEQUENCE: 6

Tyr Pro Ile Pro Asp Ser Ser Pro Leu Leu Gln Phe Gly Gly Gln Val
  1               5                  10                  15

Arg Gln Arg Tyr Leu Tyr Thr Asp Asp Gln Asp Thr Glu Ala His
            20                  25                  30

Leu Glu Ile Arg Glu Asp Gly Thr Val Val Gly Ala Ala His Arg Ser
        35                  40                  45
```

```
Pro Glu Ser Leu Leu Glu Leu Lys Ala Leu Lys Pro Gly Val Ile Gln
     50                  55                  60

Ile Leu Gly Val Lys Ala Ser Arg Phe Leu Cys Gln Gln Pro Asp Gly
 65                  70                  75                  80

Ala Leu Tyr Gly Ser Pro His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu Arg Leu Pro Gln Lys Asp Ser Pro Asn Gln Asp Ala
        115                 120                 125

Thr Ser Trp Gly Pro Val Arg Phe Leu Pro Met Pro Gly Leu Leu His
130                 135                 140

Glu Pro Gln Asp Gln Ala Gly Phe Leu Pro Pro Glu Pro Pro Asp Val
145                 150                 155                 160

Gly Ser Ser Asp Pro Leu Ser Met Val Glu Pro Leu Gln Gly Arg Ser
                165                 170                 175

Pro Ser Tyr Ala Ser
            180

<210> SEQ ID NO 7
<211> LENGTH: 21
<212> TYPE: DNA
<213> ORGANISM: Mus musculus

<400> SEQUENCE: 7
tggaatggat gagatctaga g                                           21

<210> SEQ ID NO 8
<211> LENGTH: 19
<212> TYPE: DNA
<213> ORGANISM: Mus musculus

<400> SEQUENCE: 8
ctagattcag gaagagtca                                              19

<210> SEQ ID NO 9
<211> LENGTH: 32
<212> TYPE: DNA
<213> ORGANISM: Mus musculus

<400> SEQUENCE: 9
cattgcggcc gctcaagatg caaaacgcag tg                               32

<210> SEQ ID NO 10
<211> LENGTH: 37
<212> TYPE: DNA
<213> ORGANISM: Mus musculus

<400> SEQUENCE: 10
ctactaaagc ttccaccatg gaatggatga gatctag                          37

<210> SEQ ID NO 11
<211> LENGTH: 33
<212> TYPE: DNA
<213> ORGANISM: Mus musculus

<400> SEQUENCE: 11
attcatgcgg ccgcggacgc atagctgggg ctt                              33

<210> SEQ ID NO 12
```

```
<211> LENGTH: 36
<212> TYPE: DNA
<213> ORGANISM: Homo sapiens

<400> SEQUENCE: 12
ctactaaagc ttccaccatg gactcggacg agaccg                                    36

<210> SEQ ID NO 13
<211> LENGTH: 34
<212> TYPE: DNA
<213> ORGANISM: Homo sapiens

<400> SEQUENCE: 13
attcatgcgg ccgcggaagc gtagctgggg cttc                                      34

<210> SEQ ID NO 14
<211> LENGTH: 155
<212> TYPE: PRT
<213> ORGANISM: Homo sapiens

<400> SEQUENCE: 14
```

Met Ala Glu Gly Glu Ile Thr Thr Phe Thr Ala Leu Thr Glu Lys Phe
 1               5                  10                  15

Asn Leu Pro Pro Gly Asn Tyr Lys Lys Pro Lys Leu Leu Tyr Cys Ser
                20                  25                  30

Asn Gly Gly His Phe Leu Arg Ile Leu Pro Asp Gly Thr Val Asp Gly
            35                  40                  45

Thr Arg Asp Arg Ser Asp Gln His Ile Gln Leu Gln Leu Ser Ala Glu
        50                  55                  60

Ser Val Gly Glu Val Tyr Ile Lys Ser Thr Glu Thr Gly Gln Tyr Leu
    65                  70                  75                  80

Ala Met Asp Thr Asp Gly Leu Leu Tyr Gly Ser Gln Thr Pro Asn Glu
                85                  90                  95

Glu Cys Leu Phe Leu Glu Arg Leu Glu Glu Asn His Tyr Asn Thr Tyr
            100                 105                 110

Ile Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
    130                 135                 140

Ile Leu Phe Leu Pro Leu Pro Val Ser Ser Asp
145                 150                 155

```
<210> SEQ ID NO 15
<211> LENGTH: 243
<212> TYPE: PRT
<213> ORGANISM: Homo sapiens

<400> SEQUENCE: 15
```

Met Ala Ala Ala Ile Ala Ser Ser Leu Ile Arg Gln Lys Arg Gln Ala
 1               5                  10                  15

Arg Glu Ser Asn Ser Asp Arg Val Ser Ala Ser Lys Arg Arg Ser Ser
                20                  25                  30

Pro Ser Lys Asp Gly Arg Ser Leu Cys Glu Arg His Val Leu Gly Val
            35                  40                  45

Phe Ser Lys Val Arg Phe Cys Ser Gly Arg Lys Arg Pro Val Arg Arg
        50                  55                  60

Arg Pro Glu Pro Gln Leu Lys Gly Ile Val Thr Arg Leu Phe Ser Gln
    65                  70                  75                  80

```
Gln Gly Tyr Phe Leu Gln Met His Pro Asp Gly Thr Ile Asp Gly Thr
                85                  90                  95

Lys Asp Glu Asn Ser Asp Tyr Thr Leu Phe Asn Leu Ile Pro Val Gly
            100                 105                 110

Leu Arg Val Val Ala Ile Gln Gly Val Lys Ala Ser Leu Tyr Val Ala
        115                 120                 125

Met Asn Gly Glu Gly Tyr Leu Tyr Ser Ser Asp Val Phe Thr Pro Glu
    130                 135                 140

Cys Lys Phe Lys Glu Ser Val Phe Glu Asn Tyr Tyr Val Ile Tyr Ser
145                 150                 155                 160

Ser Thr Leu Tyr Arg Gln Gln Glu Ser Gly Arg Ala Trp Phe Leu Gly
                165                 170                 175

Leu Asn Lys Glu Gly Gln Ile Met Lys Gly Asn Arg Val Lys Lys Thr
            180                 185                 190

Lys Pro Ser Ser His Phe Val Pro Lys Pro Ile Glu Val Cys Met Tyr
        195                 200                 205

Arg Glu Pro Ser Leu His Glu Ile Gly Glu Lys Gln Gly Arg Ser Arg
    210                 215                 220

Lys Ser Ser Gly Thr Pro Thr Met Asn Gly Gly Lys Val Val Asn Gln
225                 230                 235                 240

Asp Ser Thr

<210> SEQ ID NO 16
<211> LENGTH: 247
<212> TYPE: PRT
<213> ORGANISM: Homo sapiens

<400> SEQUENCE: 16

Met Ala Ala Ile Ala Ser Gly Leu Ile Arg Gln Lys Arg Gln Ala
  1               5                  10                  15

Arg Glu Gln His Trp Asp Arg Pro Ser Ala Ser Arg Arg Ser Ser
             20                  25                  30

Pro Ser Lys Asn Arg Gly Leu Cys Asn Gly Asn Leu Val Asp Ile Phe
        35                  40                  45

Ser Lys Val Arg Ile Phe Gly Leu Lys Lys Arg Arg Leu Arg Arg Gln
    50                  55                  60

Asp Pro Gln Leu Lys Gly Ile Val Thr Arg Leu Tyr Cys Arg Gln Gly
 65                  70                  75                  80

Tyr Tyr Leu Gln Met His Pro Asp Gly Ala Leu Asp Gly Thr Lys Asp
                85                  90                  95

Asp Ser Thr Asn Ser Thr Leu Phe Asn Leu Ile Pro Val Gly Leu Arg
            100                 105                 110

Val Val Ala Ile Gln Gly Val Lys Thr Gly Leu Tyr Ile Ala Met Asn
        115                 120                 125

Gly Glu Gly Tyr Leu Tyr Pro Ser Glu Leu Phe Thr Pro Glu Cys Lys
    130                 135                 140

Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
                165                 170                 175

Lys Glu Gly Gln Ala Met Lys Gly Asn Arg Val Lys Lys Thr Lys Pro
            180                 185                 190

Ala Ala His Phe Leu Pro Lys Pro Leu Glu Val Ala Met Tyr Arg Glu
        195                 200                 205
```

```
Pro Ser Leu His Asp Val Gly Glu Thr Val Pro Lys Pro Gly Val Thr
    210                 215                 220
Pro Ser Lys Ser Thr Ser Ala Ser Ala Ile Met Asn Gly Gly Lys Pro
225                 230                 235                 240
Val Asn Lys Ser Lys Thr Thr
                245
```

<210> SEQ ID NO 17
<211> LENGTH: 155
<212> TYPE: PRT
<213> ORGANISM: Homo sapiens

<400> SEQUENCE: 17

```
Met Ala Ala Gly Ser Ile Thr Thr Leu Pro Ala Leu Pro Glu Asp Gly
  1               5                  10                  15
Gly Ser Gly Ala Phe Pro Pro Gly His Phe Lys Asp Pro Lys Arg Leu
             20                  25                  30
Tyr Cys Lys Asn Gly Gly Phe Phe Leu Arg Ile His Pro Asp Gly Arg
         35                  40                  45
Val Asp Gly Val Arg Glu Lys Ser Asp Pro His Ile Lys Leu Gln Leu
     50                  55                  60
Gln Ala Glu Glu Arg Gly Val Val Ser Ile Lys Gly Val Cys Ala Asn
 65                  70                  75                  80
Arg Tyr Leu Ala Met Lys Glu Asp Gly Arg Leu Leu Ala Ser Lys Cys
                 85                  90                  95
Val Thr Asp Glu Cys Phe Phe Phe Glu Arg Leu Glu Ser Asn Asn Tyr
            100                 105                 110
Asn Thr Tyr Arg Ser Arg Lys Tyr Thr Ser Trp Tyr Val Ala Leu Lys
        115                 120                 125
Arg Thr Gly Gln Tyr Lys Leu Gly Ser Lys Thr Gly Pro Gly Gln Lys
    130                 135                 140
Ala Ile Leu Phe Leu Pro Met Ser Ala Lys Ser
145                 150                 155
```

<210> SEQ ID NO 18
<211> LENGTH: 239
<212> TYPE: PRT
<213> ORGANISM: Homo sapiens

<400> SEQUENCE: 18

```
Met Gly Leu Ile Trp Leu Leu Leu Leu Ser Leu Leu Glu Pro Gly Trp
  1               5                  10                  15
Pro Ala Ala Gly Pro Gly Ala Arg Leu Arg Arg Asp Ala Gly Gly Arg
             20                  25                  30
Gly Gly Val Tyr Glu His Leu Gly Gly Ala Pro Arg Arg Arg Lys Leu
         35                  40                  45
Tyr Cys Ala Thr Lys Tyr His Leu Gln Leu His Pro Ser Gly Arg Val
     50                  55                  60
Asn Gly Ser Leu Glu Asn Ser Ala Tyr Ser Ile Leu Glu Ile Thr Ala
 65                  70                  75                  80
Val Glu Val Gly Ile Val Ala Ile Arg Gly Leu Phe Ser Gly Arg Tyr
                 85                  90                  95
Leu Ala Met Asn Lys Arg Gly Arg Leu Tyr Ala Ser Glu His Tyr Ser
            100                 105                 110
Ala Glu Cys Glu Phe Val Glu Arg Ile His Glu Leu Gly Tyr Asn Thr
        115                 120                 125
```

```
Tyr Ala Ser Arg Leu Tyr Arg Thr Val Ser Ser Thr Pro Gly Ala Arg
            130                 135                 140

Arg Gln Pro Ser Ala Glu Arg Leu Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Asp His Arg Asp His Glu Met Val Arg
            180                 185                 190

Gln Leu Gln Ser Gly Leu Pro Arg Pro Gly Lys Gly Val Gln Pro
            195                 200                 205

Arg Arg Arg Arg Gln Lys Gln Ser Pro Asp Asn Leu Glu Pro Ser His
210                 215                 220

Val Gln Ala Ser Arg Leu Gly Ser Gln Leu Glu Ala Ser Ala His
225                 230                 235
```

<210> SEQ ID NO 19
<211> LENGTH: 206
<212> TYPE: PRT
<213> ORGANISM: Homo sapiens

<400> SEQUENCE: 19

```
Met Ser Gly Pro Gly Thr Ala Ala Val Ala Leu Leu Pro Ala Val Leu
  1               5                  10                  15

Leu Ala Leu Leu Ala Pro Trp Ala Gly Arg Gly Ala Ala Ala Pro
             20                  25                  30

Thr Ala Pro Asn Gly Thr Leu Glu Ala Glu Leu Glu Arg Arg Trp Glu
         35                  40                  45

Ser Leu Val Ala Leu Ser Leu Ala Arg Leu Pro Val Ala Ala Gln Pro
     50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                 85                  90                  95

Gln Ala Leu Pro Asp Gly Arg Ile Gly Gly Ala His Ala Asp Thr Arg
            100                 105                 110

Asp Ser Leu Leu Glu Leu Ser Pro Val Glu Arg Gly Val Val Ser Ile
        115                 120                 125

Phe Gly Val Ala Ser Arg Phe Phe Val Ala Met Ser Ser Lys Gly Lys
    130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
            180                 185                 190

Val Ser Pro Thr Met Lys Val Thr His Phe Leu Pro Arg Leu
        195                 200                 205
```

<210> SEQ ID NO 20
<211> LENGTH: 268
<212> TYPE: PRT
<213> ORGANISM: Homo sapiens

<400> SEQUENCE: 20

```
Met Ser Leu Ser Phe Leu Leu Leu Leu Phe Phe Ser His Leu Ile Leu
  1               5                  10                  15
```

-continued

Ser Ala Trp Ala His Gly Glu Lys Arg Leu Ala Pro Lys Gly Gln Pro
            20                  25                  30

Gly Pro Ala Ala Thr Asp Arg Asn Pro Ile Gly Ser Ser Ser Arg Gln
            35                  40                  45

Ser Ser Ser Ser Ala Met Ser Ser Ser Ala Ser Ser Pro Ala
 50                  55                  60

Ala Ser Leu Gly Ser Gln Gly Ser Gly Leu Glu Gln Ser Ser Phe Gln
 65                  70                  75                  80

Trp Ser Pro Ser Gly Arg Arg Thr Gly Ser Leu Tyr Cys Arg Val Gly
                85                  90                  95

Ile Gly Phe His Leu Gln Ile Tyr Pro Asp Gly Lys Val Asn Gly Ser
            100                 105                 110

His Glu Ala Asn Met Leu Ser Val Leu Glu Ile Phe Ala Val Ser Gln
            115                 120                 125

Gly Ile Val Gly Ile Arg Gly Val Phe Ser Asn Lys Phe Leu Ala Met
 130                 135                 140

Ser Lys Lys Gly Lys Leu His Ala Ser Ala Lys Phe Thr Asp Asp Cys
145                 150                 155                 160

Lys Phe Arg Glu Arg Phe Gln Glu Asn Ser Tyr Asn Thr Tyr Ala Ser
                165                 170                 175

Ala Ile His Arg Thr Glu Lys Thr Gly Arg Glu Trp Tyr Val Ala Leu
            180                 185                 190

Asn Lys Arg Gly Lys Ala Lys Arg Gly Cys Ser Pro Arg Val Lys Pro
            195                 200                 205

Gln His Ile Ser Thr His Phe Leu Pro Arg Phe Lys Gln Ser Glu Gln
            210                 215                 220

Pro Glu Leu Ser Phe Thr Val Thr Val Pro Glu Lys Lys Asn Pro Pro
225                 230                 235                 240

Ser Pro Ile Lys Ser Lys Ile Pro Leu Ser Ala Pro Arg Lys Asn Thr
            245                 250                 255

Asn Ser Val Lys Tyr Arg Leu Lys Phe Arg Phe Gly
            260                 265

<210> SEQ ID NO 21
<211> LENGTH: 208
<212> TYPE: PRT
<213> ORGANISM: Homo sapiens

<400> SEQUENCE: 21

Met Ala Leu Gly Gln Lys Leu Phe Ile Thr Met Ser Arg Gly Ala Gly
 1               5                  10                  15

Arg Leu Gln Gly Thr Leu Trp Ala Leu Val Phe Leu Gly Ile Leu Val
            20                  25                  30

Gly Met Val Val Pro Ser Pro Ala Gly Thr Arg Ala Asn Asn Thr Leu
            35                  40                  45

Leu Asp Ser Arg Gly Trp Gly Thr Leu Leu Ser Arg Ser Arg Ala Gly
 50                  55                  60

Leu Ala Gly Glu Ile Ala Gly Val Asn Trp Glu Ser Gly Tyr Leu Val
 65                  70                  75                  80

Gly Ile Lys Arg Gln Arg Arg Leu Tyr Cys Asn Val Gly Ile Gly Phe
                85                  90                  95

His Leu Gln Val Leu Pro Asp Gly Arg Ile Ser Gly Thr His Glu Glu
            100                 105                 110

Asn Pro Tyr Ser Leu Leu Glu Ile Ser Thr Val Glu Arg Gly Val Val
            115                 120                 125

```
Ser Leu Phe Gly Val Arg Ser Ala Leu Phe Val Ala Met Asn Ser Lys
    130                 135                 140

Gly Arg Leu Tyr Ala Thr Pro Ser Phe Gln Glu Cys Lys Phe Arg
145                 150                 155                 160

Glu Thr Leu Leu Pro Asn Asn Tyr Asn Ala Tyr Glu Ser Asp Leu Tyr
                165                 170                 175

Gln Gly Thr Tyr Ile Ala Leu Ser Lys Tyr Gly Arg Val Lys Arg Gly
            180                 185                 190

Ser Lys Val Ser Pro Ile Met Thr Val Thr His Phe Leu Pro Arg Ile
        195                 200                 205

<210> SEQ ID NO 22
<211> LENGTH: 194
<212> TYPE: PRT
<213> ORGANISM: Homo sapiens

<400> SEQUENCE: 22

Met His Lys Trp Ile Leu Thr Trp Ile Leu Pro Thr Leu Leu Tyr Arg
1               5                   10                  15

Ser Cys Phe His Ile Ile Cys Leu Val Gly Thr Ile Ser Leu Ala Cys
                20                  25                  30

Asn Asp Met Thr Pro Glu Gln Met Ala Thr Asn Val Asn Cys Ser Ser
            35                  40                  45

Pro Glu Arg His Thr Arg Ser Tyr Asp Tyr Met Glu Gly Gly Asp Ile
        50                  55                  60

Arg Val Arg Arg Leu Phe Cys Arg Thr Gln Trp Tyr Leu Arg Ile Asp
65                  70                  75                  80

Lys Arg Gly Lys Val Lys Gly Thr Gln Glu Met Lys Asn Asn Tyr Asn
                85                  90                  95

Ile Met Glu Ile Arg Thr Val Ala Val Gly Ile Val Ala Ile Lys Gly
                100                 105                 110

Val Glu Ser Glu Phe Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
        130                 135                 140

Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro Met Ala
            180                 185                 190

Ile Thr

<210> SEQ ID NO 23
<211> LENGTH: 208
<212> TYPE: PRT
<213> ORGANISM: Homo sapiens

<400> SEQUENCE: 23

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45
```

```
Pro Ala Val Thr Asp Leu Asp His Leu Lys Gly Ile Leu Arg Arg Arg
     50                  55                  60

Gln Leu Tyr Cys Arg Thr Gly Phe His Leu Glu Ile Phe Pro Asn Gly
 65                  70                  75                  80

Thr Ile Gln Gly Thr Arg Lys Asp His Ser Arg Phe Gly Ile Leu Glu
                 85                  90                  95

Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
                180                 185                 190

Asp Pro Asp Lys Val Pro Glu Leu Tyr Lys Asp Ile Leu Ser Gln Ser
            195                 200                 205
```

<210> SEQ ID NO 24
<211> LENGTH: 155
<212> TYPE: PRT
<213> ORGANISM: Mus musculus

<400> SEQUENCE: 24

```
Met Ala Glu Gly Glu Ile Thr Thr Phe Ala Ala Leu Thr Glu Arg Phe
 1               5                  10                  15

Asn Leu Pro Leu Gly Asn Tyr Lys Lys Pro Lys Leu Leu Tyr Cys Ser
                 20                  25                  30

Asn Gly Gly His Phe Leu Arg Ile Leu Pro Asp Gly Thr Val Asp Gly
             35                  40                  45

Thr Arg Asp Arg Ser Asp Gln His Ile Gln Leu Gln Leu Ser Ala Glu
 50                  55                  60

Ser Ala Gly Glu Val Tyr Ile Lys Gly Thr Glu Thr Gly Gln Tyr Leu
 65                  70                  75                  80

Ala Met Asp Thr Glu Gly Leu Leu Tyr Gly Ser Gln Thr Pro Asn Glu
                 85                  90                  95

Glu Cys Leu Phe Leu Glu Arg Leu Glu Glu Asn His Tyr Asn Thr Tyr
            100                 105                 110

Thr Ser Lys Lys His Ala Glu Lys Asn Trp Phe Val Gly Leu Lys Lys
        115                 120                 125

Asn Gly Ser Cys Lys Arg Gly Pro Arg Thr His Tyr Gly Gln Lys Ala
130                 135                 140

Ile Leu Phe Leu Pro Leu Pro Val Ser Ser Asp
145                 150                 155
```

<210> SEQ ID NO 25
<211> LENGTH: 245
<212> TYPE: PRT
<213> ORGANISM: Mus musculus

<400> SEQUENCE: 25

```
Met Thr Ala Ala Ile Ala Ser Ser Leu Ile Arg Gln Lys Arg Gln Ala
 1               5                  10                  15
```

```
Arg Glu Arg Glu Lys Ser Asn Ala Cys Lys Cys Val Ser Ser Pro Ser
             20                  25                  30

Lys Gly Lys Thr Ser Cys Asp Lys Asn Lys Leu Asn Val Phe Ser Arg
         35                  40                  45

Val Lys Leu Phe Gly Ser Lys Arg Arg Arg Arg Pro Glu Pro
 50                  55                  60

Gln Leu Lys Gly Ile Val Thr Lys Leu Tyr Ser Arg Gln Gly Tyr His
 65                  70                  75                  80

Leu Gln Leu Gln Ala Asp Gly Thr Ile Asp Gly Thr Lys Asp Glu Asp
                 85                  90                  95

Ser Thr Tyr Thr Leu Phe Asn Leu Ile Pro Val Gly Leu Arg Val Val
             100                 105                 110

Ala Ile Gln Gly Val Gln Thr Lys Leu Tyr Leu Ala Met Asn Ser Glu
             115                 120                 125

Gly Tyr Leu Tyr Thr Ser Glu His Phe Thr Pro Glu Cys Lys Phe Lys
130                 135                 140

Glu Ser Val Phe Glu Asn Tyr Tyr Val Thr Tyr Ser Ser Met Ile Tyr
145                 150                 155                 160

Arg Gln Gln Gln Ser Gly Arg Gly Trp Tyr Leu Gly Leu Asn Lys Glu
                165                 170                 175

Gly Glu Ile Met Lys Gly Asn His Val Lys Lys Asn Lys Pro Ala Ala
            180                 185                 190

His Phe Leu Pro Lys Pro Leu Lys Val Ala Met Tyr Lys Glu Pro Ser
            195                 200                 205

Leu His Asp Leu Thr Glu Phe Ser Arg Ser Gly Ser Gly Thr Pro Thr
            210                 215                 220

Lys Ser Arg Ser Val Ser Gly Val Leu Asn Gly Gly Lys Ser Met Ser
225                 230                 235                 240

His Asn Glu Ser Thr
                245

<210> SEQ ID NO 26
<211> LENGTH: 247
<212> TYPE: PRT
<213> ORGANISM: Mus musculus

<400> SEQUENCE: 26

Met Ala Ala Ala Ile Ala Ser Gly Leu Ile Arg Gln Lys Arg Gln Ala
 1               5                  10                  15

Arg Glu Gln His Trp Asp Arg Pro Ser Ala Ser Arg Arg Arg Ser Ser
             20                  25                  30

Pro Ser Lys Asn Arg Gly Leu Phe Asn Gly Asn Leu Val Asp Ile Phe
         35                  40                  45

Ser Lys Val Arg Ile Phe Gly Leu Lys Lys Arg Arg Leu Arg Arg Gln
 50                  55                  60

Asp Pro Gln Leu Lys Gly Ile Val Thr Arg Leu Tyr Cys Arg Gln Gly
 65                  70                  75                  80

Tyr Tyr Leu Gln Met His Pro Asp Gly Ala Leu Asp Gly Thr Lys Asp
                 85                  90                  95

Asp Ser Thr Asn Ser Thr Leu Phe Asn Leu Ile Pro Val Gly Leu Arg
             100                 105                 110

Val Val Ala Ile Gln Gly Val Lys Thr Gly Leu Tyr Ile Ala Met Asn
             115                 120                 125

Gly Glu Gly Tyr Leu Tyr Pro Ser Glu Leu Phe Thr Pro Glu Cys Lys
130                 135                 140
```

```
Phe Lys Glu Ser Val Phe Glu Asn Tyr Tyr Val Ile Tyr Ser Ser Met
145                 150                 155                 160

Leu Tyr Arg Gln Gln Glu Ser Gly Arg Ala Trp Phe Leu Gly Leu Asn
                165                 170                 175

Lys Glu Gly Gln Val Met Lys Gly Asn Arg Val Lys Lys Thr Lys Pro
                180                 185                 190

Ala Ala His Phe Leu Pro Lys Pro Leu Glu Val Ala Met Tyr Arg Glu
                195                 200                 205

Pro Ser Leu His Asp Val Gly Glu Thr Val Pro Lys Ala Gly Val Thr
                210                 215                 220

Pro Ser Lys Ser Thr Ser Ala Ser Ala Ile Met Asn Gly Lys Pro
225                 230                 235                 240

Val Asn Lys Cys Lys Thr Thr
                245

<210> SEQ ID NO 27
<211> LENGTH: 154
<212> TYPE: PRT
<213> ORGANISM: Mus musculus

<400> SEQUENCE: 27

Met Ala Ala Ser Gly Ile Thr Ser Leu Pro Ala Leu Pro Glu Asp Gly
1                   5                   10                  15

Gly Ala Ala Phe Pro Pro Gly His Phe Lys Asp Pro Lys Arg Leu Tyr
                20                  25                  30

Cys Lys Asn Gly Gly Phe Phe Leu Arg Ile His Pro Asp Gly Arg Val
                35                  40                  45

Asp Gly Val Arg Glu Lys Ser Asp Pro His Val Lys Leu Gln Leu Gln
            50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Glu Glu Cys Phe Phe Phe Glu Arg Leu Glu Ser Asn Asn Tyr Asn
                100                 105                 110

Thr Tyr Arg Ser Arg Lys Tyr Ser Ser Trp Tyr Val Ala Leu Lys Arg
                115                 120                 125

Thr Gly Gln Tyr Lys Leu Gly Ser Lys Thr Gly Pro Gly Gln Lys Ala
            130                 135                 140

Ile Leu Phe Leu Pro Met Ser Ala Lys Ser
145                 150

<210> SEQ ID NO 28
<211> LENGTH: 245
<212> TYPE: PRT
<213> ORGANISM: Mus musculus

<400> SEQUENCE: 28

Met Gly Leu Ile Trp Leu Leu Leu Leu Ser Leu Leu Glu Pro Ser Trp
1                   5                   10                  15

Pro Thr Thr Gly Pro Gly Thr Arg Leu Arg Arg Asp Ala Gly Gly Arg
                20                  25                  30

Gly Gly Val Tyr Glu His Leu Gly Gly Ala Pro Arg Arg Arg Lys Leu
                35                  40                  45

Tyr Cys Ala Thr Lys Tyr His Leu Gln Leu His Pro Ser Gly Arg Val
            50                  55                  60
```

```
Asn Gly Ser Leu Glu Asn Ser Ala Tyr Ser Ile Leu Glu Ile Thr Ala
 65                  70                  75                  80

Val Glu Val Gly Val Ala Ile Lys Gly Leu Phe Ser Gly Arg Tyr
                 85                  90                  95

Leu Ala Met Asn Lys Arg Gly Arg Leu Tyr Ala Ser Asp His Tyr Asn
            100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Gly Ser Ser Gly Pro Gly Ala Gln
130                 135                 140

Arg Gln Pro Gly Ala Gln Arg Pro Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu Gly His Lys Asp His Glu Met Val Arg
            180                 185                 190

Leu Leu Gln Ser Ser Gln Pro Arg Ala Pro Gly Glu Gly Ser Gln Pro
            195                 200                 205

Arg Gln Arg Arg Gln Lys Lys Gln Ser Pro Gly Asp His Gly Lys Met
210                 215                 220

Glu Thr Leu Ser Thr Arg Ala Thr Pro Ser Thr Gln Leu His Thr Gly
225                 230                 235                 240

Gly Leu Ala Val Ala
            245

<210> SEQ ID NO 29
<211> LENGTH: 202
<212> TYPE: PRT
<213> ORGANISM: Mus musculus

<400> SEQUENCE: 29

Met Ala Lys Arg Gly Pro Thr Thr Gly Thr Leu Leu Pro Arg Val Leu
 1               5                  10                  15

Leu Ala Leu Val Val Ala Leu Ala Asp Arg Gly Thr Ala Ala Pro Asn
                20                  25                  30

Gly Thr Arg His Ala Glu Leu Gly His Gly Trp Asp Gly Leu Val Ala
            35                  40                  45

Arg Ser Leu Ala Arg Leu Pro Val Ala Ala Gln Pro Pro Gln Ala Ala
        50                  55                  60

Val Arg Ser Gly Ala Gly Asp Tyr Leu Leu Gly Leu Lys Arg Leu Arg
 65                  70                  75                  80

Arg Leu Tyr Cys Asn Val Gly Ile Gly Phe His Leu Gln Val Leu Pro
                 85                  90                  95

Asp Gly Arg Ile Gly Gly Val His Ala Asp Thr Arg Asp Ser Leu Leu
            100                 105                 110

Glu Leu Ser Pro Val Gln Arg Gly Val Val Ser Ile Phe Gly Val Ala
        115                 120                 125

Ser Arg Phe Phe Val Ala Met Ser Ser Arg Gly Lys Leu Phe Gly Val
130                 135                 140

Pro Phe Phe Thr Asp Glu Cys Lys Phe Lys Glu Ile Leu Leu Pro Asn
145                 150                 155                 160

Asn Tyr Asn Ala Tyr Glu Ala Tyr Ala Tyr Pro Gly Met Phe Met Ala
                165                 170                 175

Leu Ser Lys Asn Gly Arg Thr Lys Lys Gly Asn Arg Val Ser Pro Thr
```

-continued

```
                180                 185                 190
Met Lys Val Thr His Phe Leu Pro Arg Leu
            195                 200

<210> SEQ ID NO 30
<211> LENGTH: 264
<212> TYPE: PRT
<213> ORGANISM: Mus musculus

<400> SEQUENCE: 30

Met Ser Leu Ser Leu Leu Phe Leu Ile Phe Cys Ser His Leu Ile His
  1               5                  10                  15

Ser Ala Trp Ala His Gly Glu Lys Arg Leu Thr Pro Glu Gly Gln Pro
             20                  25                  30

Ala Pro Pro Arg Asn Pro Gly Asp Ser Ser Gly Ser Arg Gly Arg Ser
         35                  40                  45

Ser Ala Thr Phe Ser Ser Ser Ala Ser Ser Pro Val Ala Ala Ser
     50                  55                  60

Pro Gly Ser Gln Gly Ser Gly Ser Glu His Ser Ser Phe Gln Trp Ser
 65                  70                  75                  80

Pro Ser Gly Arg Arg Thr Gly Ser Leu Tyr Cys Arg Val Gly Ile Gly
                 85                  90                  95

Phe His Leu Gln Ile Tyr Pro Asp Gly Lys Val Asn Gly Ser His Glu
            100                 105                 110

Ala Ser Val Leu Ser Ile Leu Glu Ile Phe Ala Val Ser Gln Gly Ile
        115                 120                 125

Val Gly Ile Arg Gly Val Phe Ser Asn Lys Phe Leu Ala Met Ser Lys
    130                 135                 140

Lys Gly Lys Leu His Ala Ser Ala Lys Phe Thr Asp Asp Cys Lys Phe
145                 150                 155                 160

Arg Glu Arg Phe Gln Glu Asn Ser Tyr Asn Thr Tyr Ala Ser Ala Ile
                165                 170                 175

His Arg Thr Glu Lys Thr Gly Arg Glu Trp Tyr Val Ala Leu Asn Lys
            180                 185                 190

Arg Gly Lys Ala Lys Arg Gly Cys Ser Pro Arg Val Lys Pro Gln His
        195                 200                 205

Val Ser Thr His Phe Leu Pro Arg Phe Lys Gln Ser Glu Gln Pro Glu
    210                 215                 220

Leu Ser Phe Thr Val Thr Val Pro Glu Lys Lys Lys Pro Pro Val Lys
225                 230                 235                 240

Pro Lys Val Pro Leu Ser Gln Pro Arg Ser Pro Ser Pro Val Lys
                245                 250                 255

Tyr Arg Leu Lys Phe Arg Phe Gly
            260

<210> SEQ ID NO 31
<211> LENGTH: 208
<212> TYPE: PRT
<213> ORGANISM: Mus musculus

<400> SEQUENCE: 31

Met Ala Leu Gly Gln Arg Leu Phe Ile Thr Met Ser Arg Gly Ala Gly
  1               5                  10                  15

Arg Val Gln Gly Thr Leu Gln Ala Leu Val Phe Leu Gly Val Leu Val
             20                  25                  30

Gly Met Val Val Pro Ser Pro Ala Gly Ala Arg Ala Asn Gly Thr Leu
```

```
              35                  40                  45
Leu Asp Ser Arg Gly Trp Gly Thr Leu Ser Arg Ser Arg Ala Gly
 50                  55                  60

Leu Ala Gly Glu Ile Ser Gly Val Asn Trp Glu Ser Gly Tyr Leu Val
 65                  70                  75                  80

Gly Ile Lys Arg Gln Arg Leu Tyr Cys Asn Val Gly Ile Gly Phe
                 85                  90                  95

His Leu Gln Val Pro Pro Asp Gly Arg Ile Ser Gly Thr His Glu Glu
                100                 105                 110

Asn Pro Tyr Ser Leu Leu Glu Ile Ser Thr Val Glu Arg Gly Val Val
                115                 120                 125

Ser Leu Phe Gly Val Lys Ser Ala Leu Phe Ile Ala Met Asn Ser Lys
    130                 135                 140

Gly Arg Leu Tyr Thr Thr Pro Ser Phe His Asp Glu Cys Lys Phe Arg
145                 150                 155                 160

Glu Thr Leu Leu Pro Asn Asn Tyr Asn Ala Tyr Glu Ser Asp Leu Tyr
                165                 170                 175

Arg Gly Thr Tyr Ile Ala Leu Ser Lys Tyr Gly Arg Val Lys Arg Gly
                180                 185                 190

Ser Lys Val Ser Pro Ile Met Thr Val Thr His Phe Leu Pro Arg Ile
                195                 200                 205

<210> SEQ ID NO 32
<211> LENGTH: 194
<212> TYPE: PRT
<213> ORGANISM: Mus musculus

<400> SEQUENCE: 32

Met Arg Lys Trp Ile Leu Thr Arg Ile Leu Pro Thr Leu Leu Tyr Arg
  1               5                  10                  15

Ser Cys Phe His Leu Val Cys Leu Val Gly Thr Ile Ser Leu Ala Cys
                 20                  25                  30

Asn Asp Met Ser Pro Glu Gln Thr Ala Thr Ser Val Asn Cys Ser Ser
             35                  40                  45

Pro Glu Arg His Thr Arg Ser Tyr Asp Tyr Met Glu Gly Gly Asp Ile
 50                  55                  60

Arg Val Arg Arg Leu Phe Cys Arg Thr Gln Trp Tyr Leu Arg Ile Asp
 65                  70                  75                  80

Lys Arg Gly Lys Val Lys Gly Thr Gln Glu Met Lys Asn Ser Tyr Asn
                 85                  90                  95

Ile Met Glu Ile Arg Thr Val Ala Val Gly Ile Val Ala Ile Lys Gly
                100                 105                 110

Val Glu Ser Glu Tyr Tyr Leu Ala Met Asn Lys Glu Gly Lys Leu Tyr
            115                 120                 125

Ala Lys Lys Glu Cys Asn Glu Asp Cys Asn Phe Lys Glu Leu Ile Leu
    130                 135                 140

Glu Asn His Tyr Asn Thr Tyr Ala Ser Ala Lys Trp Thr His Ser Gly
145                 150                 155                 160

Gly Glu Met Phe Val Ala Leu Asn Gln Lys Gly Ile Pro Val Lys Gly
                165                 170                 175

Lys Lys Thr Lys Lys Glu Gln Lys Thr Ala His Phe Leu Pro Met Ala
                180                 185                 190

Ile Thr
```

<210> SEQ ID NO 33
<211> LENGTH: 208
<212> TYPE: PRT
<213> ORGANISM: Mus musculus

<400> SEQUENCE: 33

Met Ala Pro Leu Gly Glu Val Gly Ser Tyr Phe Gly Val Gln Asp Ala
1               5                   10                  15

Val Pro Phe Gly Asn Val Pro Val Leu Pro Val Asp Ser Pro Val Leu
            20                  25                  30

Leu Asn Asp His Leu Gly Gln Ser Glu Ala Gly Gly Leu Pro Arg Gly
        35                  40                  45

Pro Ala Val Thr Asp Leu Asp His Leu Lys Gly Ile Leu Arg Arg Arg
    50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95

Phe Ile Ser Ile Ala Val Gly Leu Val Ser Ile Arg Gly Val Asp Ser
            100                 105                 110

Gly Leu Tyr Leu Gly Met Asn Glu Lys Gly Glu Leu Tyr Gly Ser Glu
        115                 120                 125

Lys Leu Thr Gln Glu Cys Val Phe Arg Glu Gln Phe Glu Glu Asn Trp
130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg Pro Val
            180                 185                 190

Asp Pro Asp Lys Val Pro Glu Leu Tyr Lys Asp Ile Leu Ser Gln Ser
        195                 200                 205

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: Random
      primer with Not I restriction site for first strand cDNA
      synthesis
<220> FEATURE:
<221> NAME/KEY: misc_feature
<222> LOCATION: (25)..(33)
<223> OTHER INFORMATION: "N" can be A, G, C, or T

<400> SEQUENCE: 34
ggaaggaaaa aagcggccgc aacannnnnn nnn                                33

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Primer for
      first strand cDNA synthesis

<400> SEQUENCE: 35
aatccgatgc ccacgttgca gta                                           23

<210> SEQ ID NO 36

```
<211> LENGTH: 26
<212> TYPE: DNA
<213> ORGANISM: Artificial Sequence
<220> FEATURE:
<223> OTHER INFORMATION: Description of Artificial Sequence: PCR primer
      for amplification of cDNA

<400> SEQUENCE: 36
aaaatcttag accgacgact gtgttt                                           26

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: PCR primer
      for amplification of cDNA

<400> SEQUENCE: 37
gagtctccgc agccttttga gg                                               22

<210> SEQ ID NO 38
<211> LENGTH: 34
<212> TYPE: DNA
<213> ORGANISM: Homo sapiens

<400> SEQUENCE: 38
actggcggcc gcaggcatca tcccagttga ggag                                  34

<210> SEQ ID NO 39
<211> LENGTH: 36
<212> TYPE: DNA
<213> ORGANISM: Homo sapiens

<400> SEQUENCE: 39
actggtcact cgagggtacc ttagctagcc cccggg                                36

<210> SEQ ID NO 40
<211> LENGTH: 29
<212> TYPE: PRT
<213> ORGANISM: Mus musculus

<400> SEQUENCE: 40

Met Glu Trp Met Arg Ser Arg Val Gly Thr Leu Gly Leu Trp Val Arg
 1               5                  10                  15

Leu Leu Leu Ala Val Phe Leu Leu Gly Val Tyr Gln Ala
            20                  25

<210> SEQ ID NO 41
<211> LENGTH: 28
<212> TYPE: PRT
<213> ORGANISM: Homo sapiens

<400> SEQUENCE: 41

Met Asp Ser Asp Glu Thr Gly Phe Glu His Ser Gly Leu Trp Val Ser
 1               5                  10                  15

Val Leu Ala Gly Leu Leu Leu Gly Ala Cys Gln Ala
            20                  25
```